US011345750B2

(12) United States Patent
Raats et al.

(10) Patent No.: US 11,345,750 B2
(45) Date of Patent: May 31, 2022

(54) ANTIBODIES BINDING TO CITRULLINATED HISTONE 2A AND/OR 4

(71) Applicant: CITRYLL B.V., Oss (NL)

(72) Inventors: Jozef Maria Hendrik Raats, Nijmegen (NL); Renato Gerardus Silvano Chirivi, Oosterhout (NL); Johannes Wilhelmus Gerardus Van Rosmalen, Oss (NL)

(73) Assignee: CITRYLL B.V., Oss (NL)

( * ) Notice: Subject to any disclaimer, the term of this patent is extended or adjusted under 35 U.S.C. 154(b) by 0 days.

(21) Appl. No.: 17/368,720

(22) Filed: Jul. 6, 2021

(65) Prior Publication Data

US 2021/0403543 A1   Dec. 30, 2021

Related U.S. Application Data

(63) Continuation of application No. 17/269,509, filed as application No. PCT/EP2019/072302 on Aug. 20, 2019.

(30) Foreign Application Priority Data

Aug. 21, 2018  (GB) ...................................... 1813597
Jan. 24, 2019  (GB) ...................................... 1900983

(51) Int. Cl.
| C07K 16/18 | (2006.01) |
| A61P 29/00 | (2006.01) |
| A61P 37/06 | (2006.01) |
| A61P 19/02 | (2006.01) |
| A61K 39/00 | (2006.01) |

(52) U.S. Cl.
CPC .............. *C07K 16/18* (2013.01); *A61P 19/02* (2018.01); *A61P 29/00* (2018.01); *A61P 37/06* (2018.01); *A61K 2039/505* (2013.01); *C07K 2317/24* (2013.01); *C07K 2317/565* (2013.01); *C07K 2317/622* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| WO | WO 2009/147201 | 12/2009 |
| WO | WO 2011/070172 | 6/2011 |
| WO | WO 2015/189638 | 12/2015 |
| WO | WO 2016/092082 | 6/2016 |

OTHER PUBLICATIONS

Cacia et al., "Isomerization of an Aspartic Acid Residue in the Complementarity-Determining Regions of a Recombinant Antibody to Human IgE: Identification and Effect on Binding Affinity," Biochemistry, 1996, vol. 35, No. 6, 1897-1903.
Chen et al., "Generation and Analysis of Random Point Mutations in an Antibody CDR2 Sequence: Many Mutated Antibodies Lose Their Ability to Bind Antigen," J Exp Med, vol. 176, 1992, 855-866.
Kienhöefer et al., "Experimental lupus is aggravated in mouse strains with impaired induction of neutrophil extracellular traps," JCI Insight 2017 2(10): e92920.
Kraaij et al., "A novel method for high-throughput detection and quantification of neutrophil extracellular traps reveals ROS-independent NET release with immune complexes," 2016, Autoimmun. Rev. 15, 577-584.
Muller et al., "Citrullinated Autoantigens: From Diagnostic Markers to Pathogenetic Mechanisms," Clinical Reviews in Allergy and Immunology, Humana Press, Totowa, NJ, US, vol. 49, No. 2, 2014, pp. 232-239.
Patel et al., "N+1 Engineering of an Aspartate Isomerization Hotspot in the Complementarity-Determining Region of a Monoclonal Antibody," Journal of pharmaceutical sciences, vol. 105, No. 2, Feb. 2016, pp. 512-518.

(Continued)

*Primary Examiner* — Phillip Gambel
(74) *Attorney, Agent, or Firm* — Morrison & Foerster LLP

(57) ABSTRACT

The invention provides antibodies or binding fragments thereof directed against citrulline-containing epitopes. The antibodies or binding fragments thereof of the invention can be used in therapy, for example in the treatment or prevention of Neutrophil Extracellular Trap (NET)-associated pathologies. The antibodies or binding fragments thereof of the invention can be used in the treatment or prevention of NET-associated pathologies such as systemic lupus erythematosus (SLE), lupus, sepsis, vasculitis, inflammatory arthritis, rheumatoid arthritis and osteoarthritis, psoriasis, Alzheimer's disease, autoimmune hepatitis, juvenile idiopathic arthritis, Sjögren's disease, Anti-phospholipid Syndrome, Bechet's disease, spondylitis, spondyloarthropathy, multiple system atrophy, Parkinson's disease, Lewy body dementia asthma, allergic rhinovirus exacerbated asthma, allergic asthma, cystic fibrosis, fibrosis and idiopathic pulmonary fibrosis, dry eye disease, uveitis, nongranulomatous uveitis, granulomatous uveitis, dermatitis, atopic dermatitis, COPD, bronchitis, or other NET-associated pathologies such as wound healing in diabetes, cancer, cancer metastasis, and transplant organ health in vivo or ex vivo. The invention also provides pharmaceutical compositions and methods for treating or preventing NET-associated pathologies such as SLE, lupus, sepsis, vasculitis, inflammatory arthritis, rheumatoid arthritis and osteoarthritis, psoriasis, Alzheimer's disease, autoimmune hepatitis, juvenile idiopathic arthritis, Sjögren's disease, Anti-phospholipid Syndrome, Bechet's disease, spondylitis, spondyloarthropathy, multiple system atrophy, Parkinson's disease, Lewy body dementia asthma, allergic rhinovirus exacerbated asthma, allergic asthma, cystic fibrosis, fibrosis and idiopathic pulmonary fibrosis, dry eye disease, uveitis, nongranulomatous uveitis, granulomatous uveitis, dermatitis, atopic dermatitis, COPD, bronchitis, or other NET-associated pathologies such as wound healing in diabetes, cancer, cancer metastasis, and transplant organ health in vivo or ex vivo.

15 Claims, 16 Drawing Sheets

Specification includes a Sequence Listing.

(56) References Cited

OTHER PUBLICATIONS

Pauthner et al., "Antibody engineering & therapeutics," The Annual Meeting of the Antibody Society, Dec. 7-10, 2015, San Diego, CA, USA, MABS, vol. 8, No. 3, 2016, pp. 617-652.

Winkler et al., "Changing the Antigen Binding Specificity by Single Point Mutations of an Anti-p24 (HIV-1) Antibody," J Immunol, 2000; 165:4505-4514.

Yi et al., "Isomerization of Asp-Asp motif in model peptides and a monoclonal antibody Fab fragment.", Journal of pharmaceutical Sciences, vol. 102, No. 3, Mar. 2013, pp. 947-959.

Fig. 1
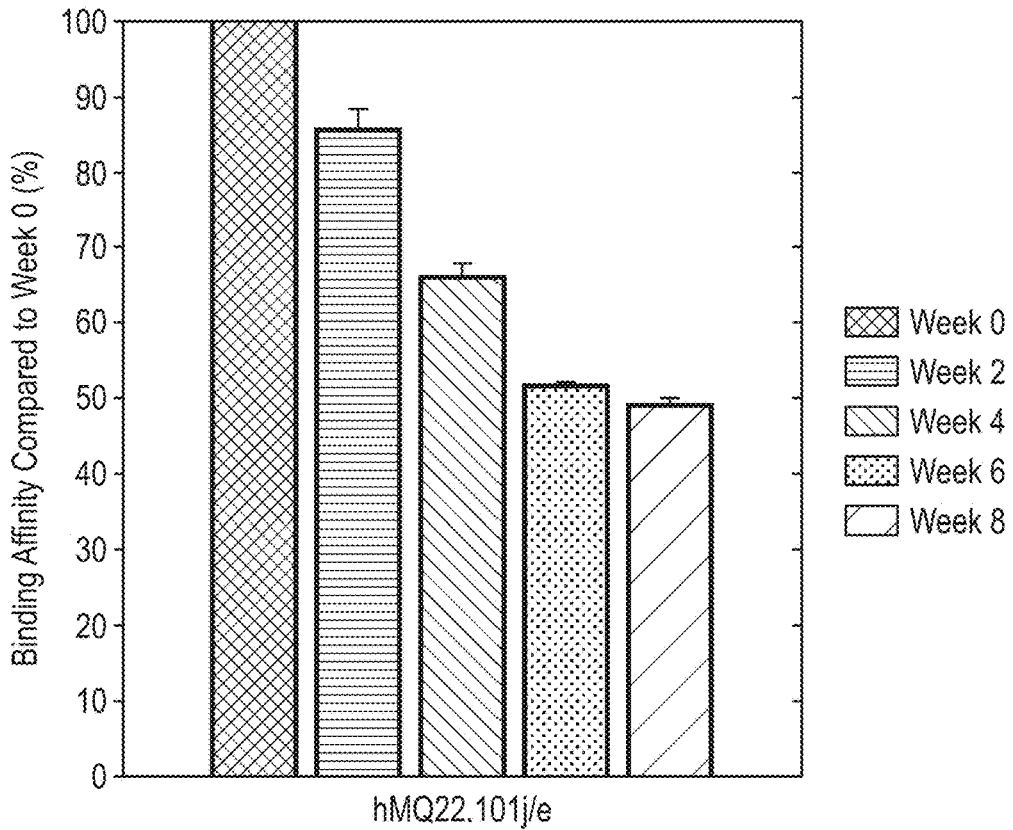
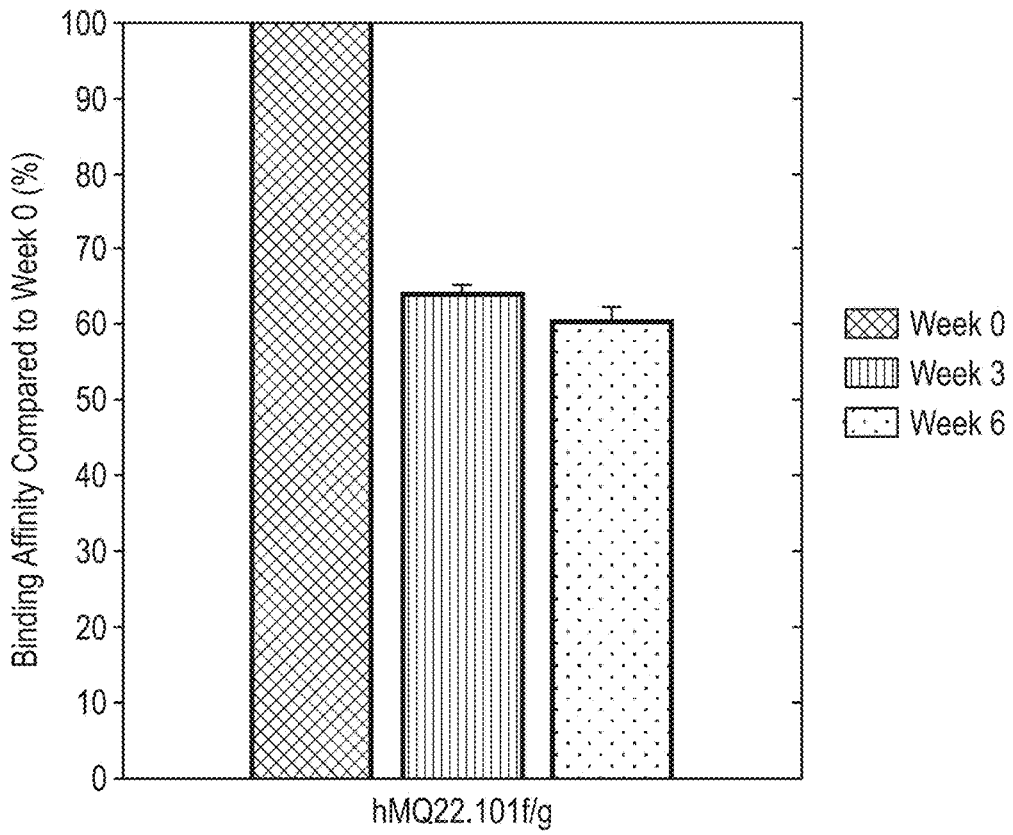

Fig. 3A

| LC Construct | # Residue in the LC | | | | |
|---|---|---|---|---|---|
| | #30 | #31 | #32 | #33 | #34 |
| hVL22.101e | V | D | S | D | G |
| hVL22.101g | L | D | S | D | G |
| hVL22.101LC16 | L | E | S | D | G |
| hVL22.101LC17 | L | D | T | D | G |
| hVL22.101LC19 | L | D | S | E | G |
| hVL22.101LC20 | L | D | S | S | G |
| hVL22.101LC21 | L | D | S | D | A |
| hVL22.101LC22 | L | E | S | E | G |
| hVL22.101LC23 | L | E | S | S | G |
| hVL22.101LC24 | L | E | S | D | A |
| hVL22.101LC25 | L | D | T | E | G |
| hVL22.101LC26 | L | D | T | S | G |
| hVL22.101LC27 | L | D | T | D | A |
| hVL22.101LC37 | L | D | S | A | G |
| hVL22.101LC38 | L | E | S | A | G |
| hVL22.101LC39 | L | D | A | E | G |
| hVL22.101LC40 | L | D | N | E | G |
| hVL22.101LC41 | L | D | A | D | G |
| hVL22.101LC42 | L | D | N | D | G |

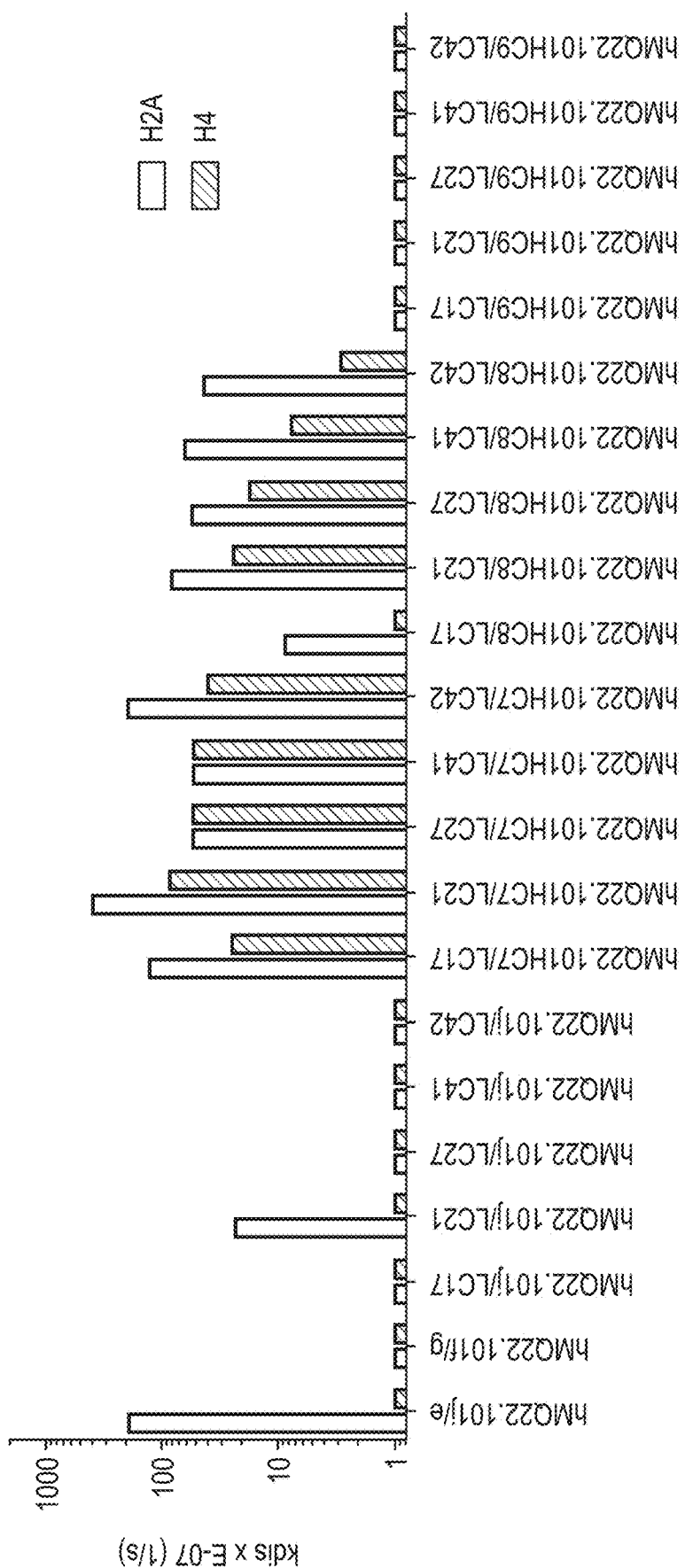

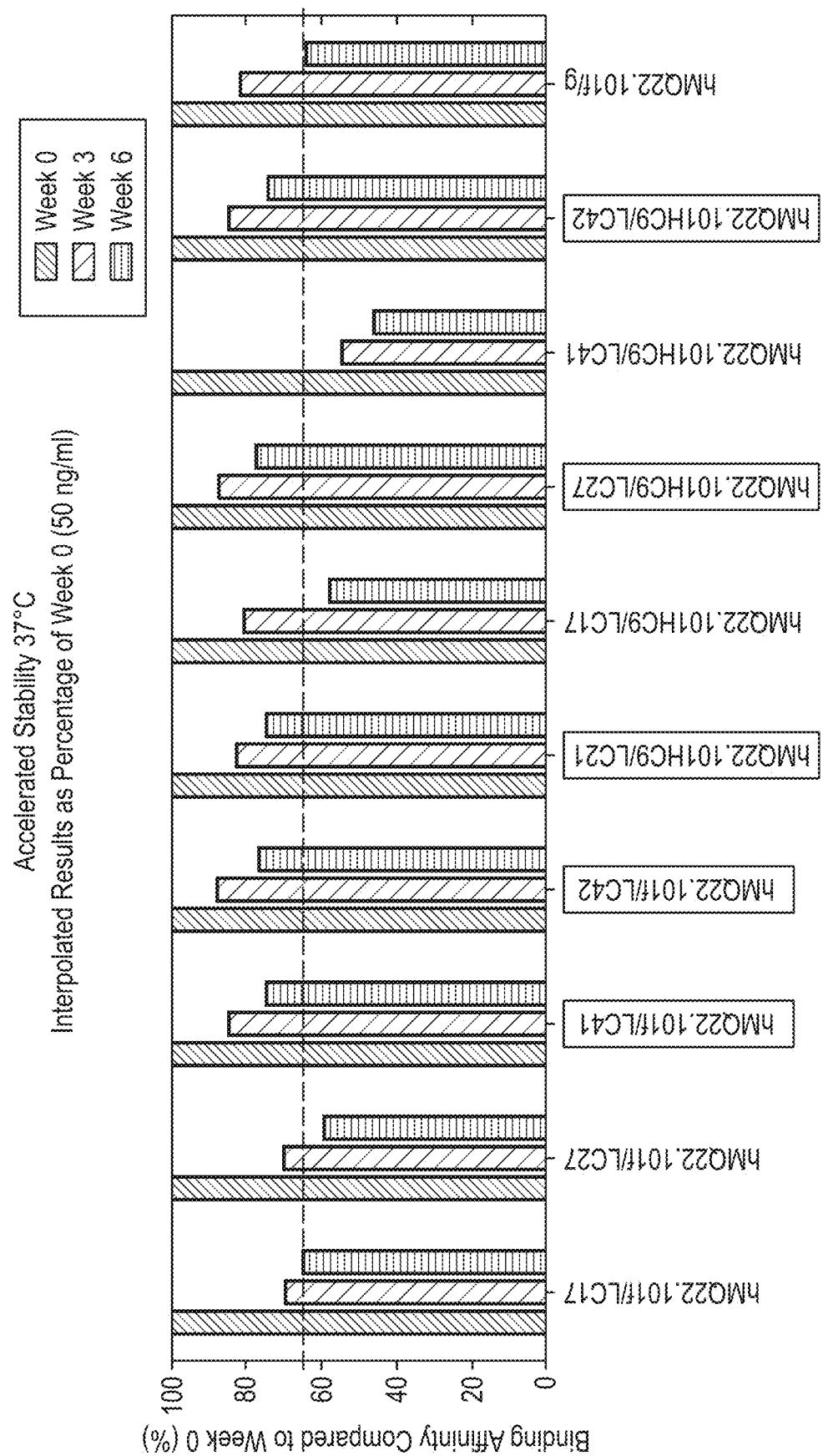

Fig. 5

| Antibody | Lot# | Sequence | Modification | Week 0 | Week 4 | Week 6 | Week 8 |
|---|---|---|---|---|---|---|---|
| hMQ22.101j/e | 16151 | XDSDGX | Isoaspartate | 1.6% | 27.1% | | 39.9% |
| hMQ22.101f/LC41 | 17362 | LDADGK | Isoaspartate | 0.6% | | 1.1% | |
| hMQ22.101f/LC42 | 17363 | LDNDGK | Isoaspartate | 1.2% | | 3.1% | |
| hMQ22.101HC9/LC21 | 17364 | LDSDAK | Isoaspartate | 0.6% | | 10.9% | |
| hMQ22.101HC9/LC27 | 17392 | LDTDAK | Isoaspartate | 0.5% | | 9.7% | |
| hMQ22.101HC9/LC42 | 17394 | LDNDGK | Isoaspartate | 0.5% | | 3.1% | |

Fig. 6

| | | Aggregation | | Degradation | |
|---|---|---|---|---|---|
| Antibody | Lot# | Week 0 | Week 6 | Week 0 | Week 6 |
| hMQ22.101f/LC41 | 17362 | 0.20% | 0.20% | -- | 0.20% |
| hMQ22.101f/LC42 | 17363 | 0.13% | 0.17% | -- | 0.17% |
| hMQ22.101HC9/LC42 | 17394 | 0.11% | 0.13% | -- | 0.17% |

Fig. 7
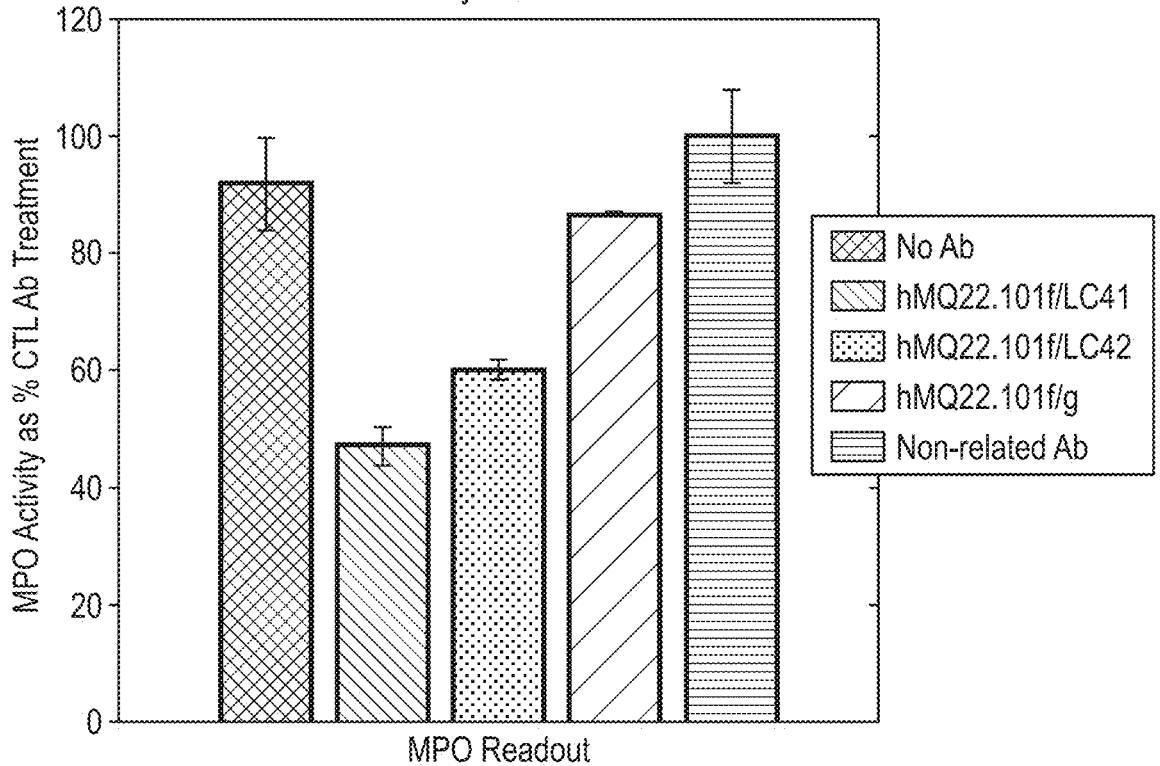
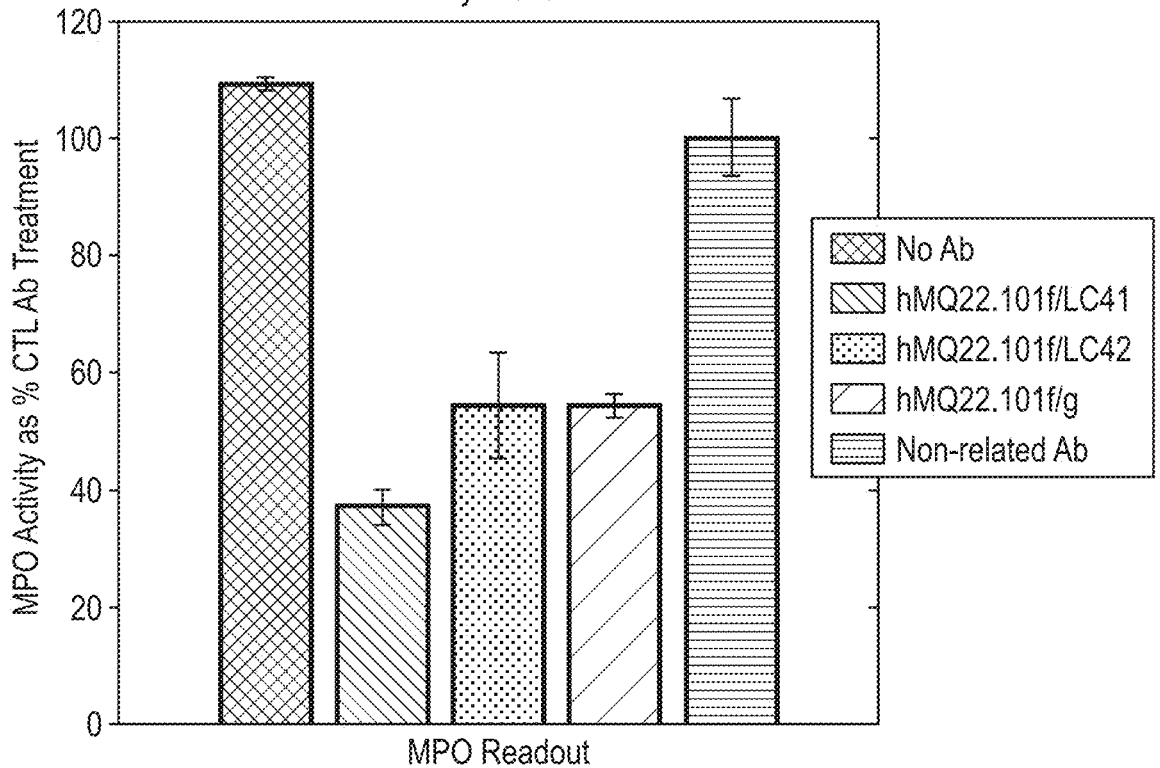

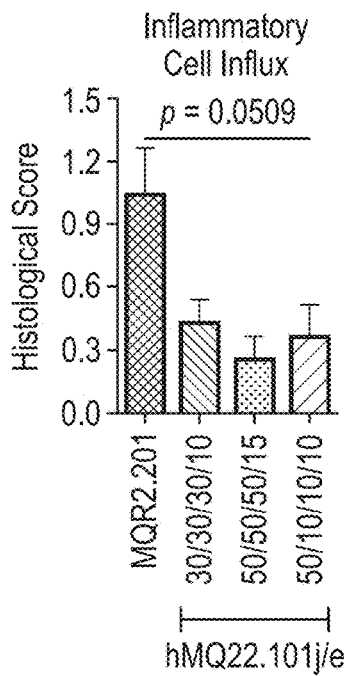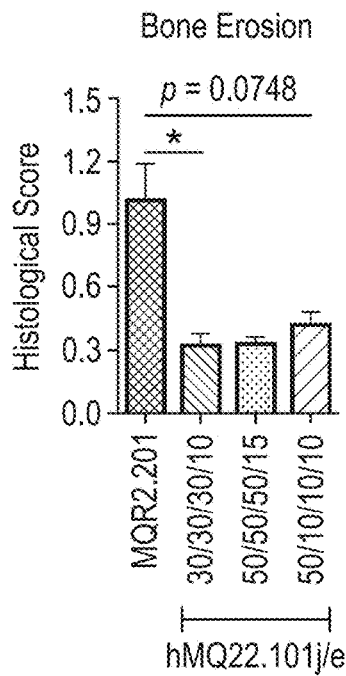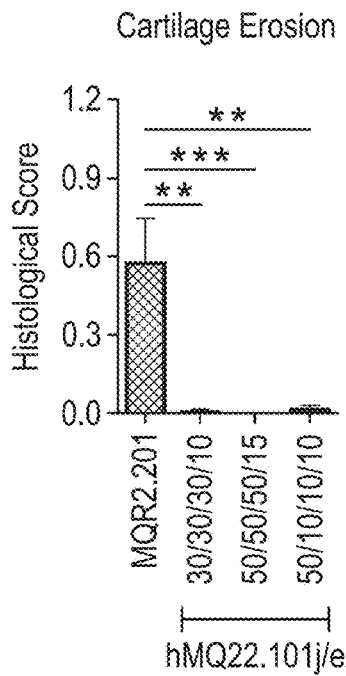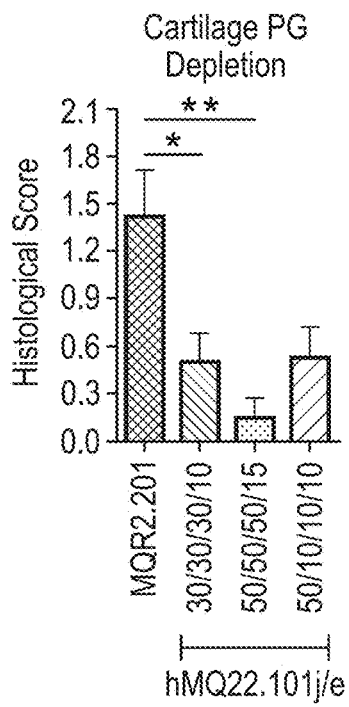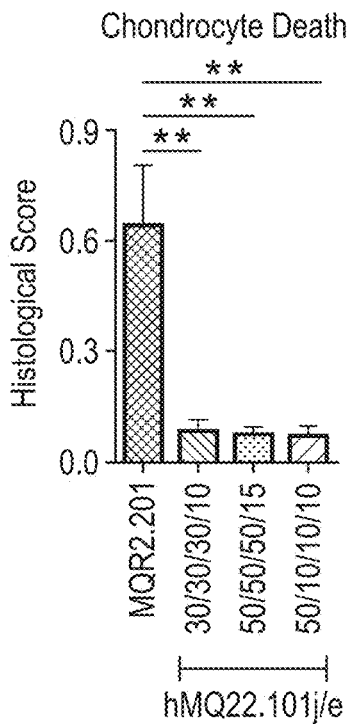

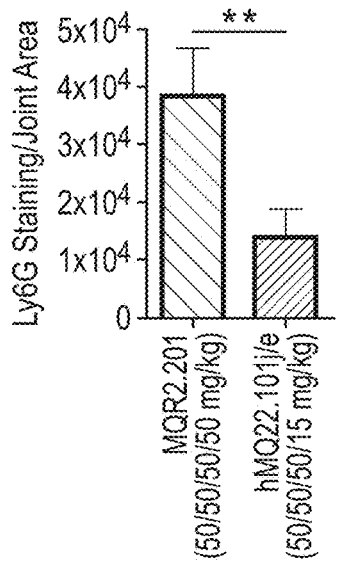
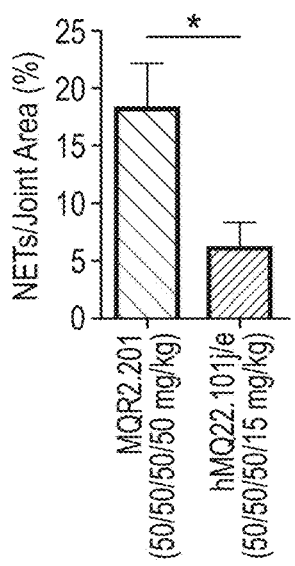
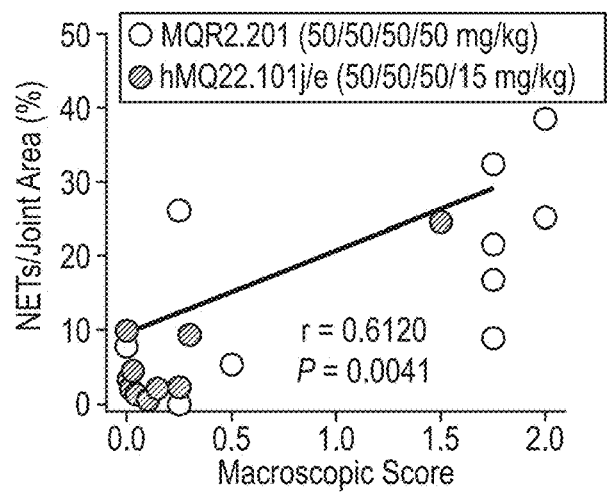
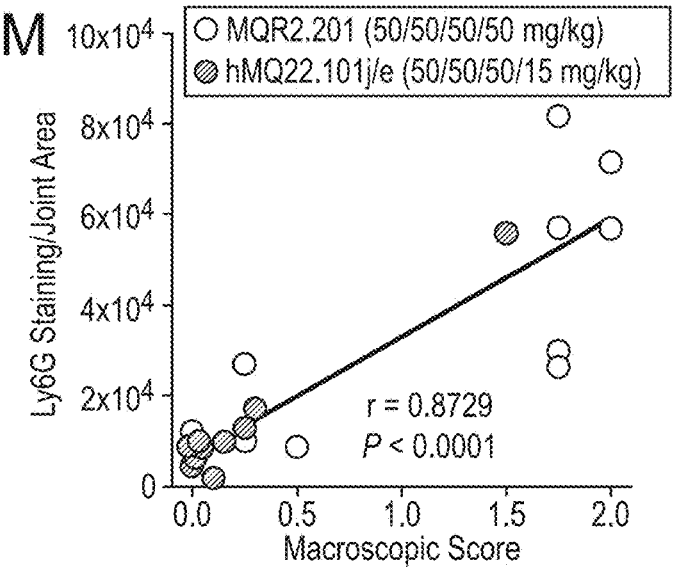

```
                          SEQUENCE LISTING

<160> NUMBER OF SEQ ID NOS: 58

<210> SEQ ID NO 1
<211> LENGTH: 8
<212> TYPE: PRT
<213> ORGANISM: Artificial sequence
<220> FEATURE:
<223> OTHER INFORMATION: CDR1 of msVH22.101 and hVH22.101(HC)x

<400> SEQUENCE: 1

Gly Tyr Thr Phe Thr Asn Tyr Gly
1               5

<210> SEQ ID NO 2
<211> LENGTH: 8
<212> TYPE: PRT
<213> ORGANISM: Artificial sequence
<220> FEATURE:
<223> OTHER INFORMATION: CDR2 of msVH22.101 and hVH22.101(HC)x

<400> SEQUENCE: 2

Ile Asn Thr Tyr Ser Gly Glu Ala
1               5

<210> SEQ ID NO 3
<211> LENGTH: 15
<212> TYPE: PRT
<213> ORGANISM: Artificial sequence
<220> FEATURE:
<223> OTHER INFORMATION: CDR3 of msVH22.101 and hVH22.101(HC)x

<400> SEQUENCE: 3

Leu Arg Gly Tyr Thr Tyr Gln Ser Phe Asp Glu Gly Gly Asp Tyr
1               5                   10                  15

<210> SEQ ID NO 4
<211> LENGTH: 3
<212> TYPE: PRT
<213> ORGANISM: Artificial sequence
<220> FEATURE:
<223> OTHER INFORMATION: CDR2 of msVL22.101 and hVL22.101(LC)y

<400> SEQUENCE: 4

Leu Val Ser
1
```

<210> SEQ ID NO 5
<211> LENGTH: 9
<212> TYPE: PRT
<213> ORGANISM: Artificial sequence
<220> FEATURE:
<223> OTHER INFORMATION: CDR3 of msVL22.101 and hVL22.101(LC)y

<400> SEQUENCE: 5

Trp Gln Gly Thr His Phe Pro Tyr Thr
1               5

<210> SEQ ID NO 6
<211> LENGTH: 11
<212> TYPE: PRT
<213> ORGANISM: Homo sapiens

<400> SEQUENCE: 6

Gln Ser Leu Leu Asp Thr Asp Gly Lys Thr Tyr
1               5                   10

<210> SEQ ID NO 7
<211> LENGTH: 11
<212> TYPE: PRT
<213> ORGANISM: Homo sapiens

<400> SEQUENCE: 7

Gln Ser Leu Leu Asp Ser Asp Ala Lys Thr Tyr
1               5                   10

<210> SEQ ID NO 8
<211> LENGTH: 11
<212> TYPE: PRT
<213> ORGANISM: Homo sapiens

<400> SEQUENCE: 8

Gln Ser Leu Leu Asp Thr Asp Ala Lys Thr Tyr
1               5                   10

<210> SEQ ID NO 9
<211> LENGTH: 11
<212> TYPE: PRT
<213> ORGANISM: Homo sapiens

<400> SEQUENCE: 9

Gln Ser Leu Leu Asp Ala Asp Gly Lys Thr Tyr
1               5                   10

<210> SEQ ID NO 10
<211> LENGTH: 11
<212> TYPE: PRT
<213> ORGANISM: Homo sapiens

<400> SEQUENCE: 10

Gln Ser Leu Leu Asp Asn Asp Gly Lys Thr Tyr
1               5                   10

<210> SEQ ID NO 11
<211> LENGTH: 122
<212> TYPE: PRT
<213> ORGANISM: Artificial sequence
<220> FEATURE:
<223> OTHER INFORMATION: hVH22.101f -continued

<400> SEQUENCE: 11

Arg Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met His Trp Val Arg Gln Ala Pro Gly Gln Gly Leu Glu Trp Met
        35                  40                  45

Gly Trp Ile Asn Thr Tyr Ser Gly Glu Ala Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Leu Arg Gly Tyr Thr Tyr Gln Ser Phe Asp Glu Gly Gly Asp Tyr Trp
            100                 105                 110

Gly Gln Gly Thr Leu Val Thr Val Ser Ser
        115                 120

<210> SEQ ID NO 12
<211> LENGTH: 122
<212> TYPE: PRT
<213> ORGANISM: Homo sapiens

<400> SEQUENCE: 12

Arg Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met His Trp Val Arg Gln Ala Pro Gly Gln Gly Leu Glu Trp Met
        35                  40                  45

Gly Trp Ile Asn Thr Tyr Ser Gly Glu Ala Thr Tyr Val Asp Asp Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Leu Arg Gly Tyr Thr Tyr Gln Ser Phe Asp Glu Gly Gly Asp Tyr Trp
            100                 105                 110

Gly Gln Gly Thr Leu Val Thr Val Ser Ser
        115                 120

<210> SEQ ID NO 13
<211> LENGTH: 112
<212> TYPE: PRT
<213> ORGANISM: Homo sapiens

<400> SEQUENCE: 13

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Thr
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Tyr Thr Phe Gly Gln Gly Thr Lys Leu Glu Ile Lys
            100                 105                 110
```

<210> SEQ ID NO 14
<211> LENGTH: 112
<212> TYPE: PRT
<213> ORGANISM: Homo sapiens

<400> SEQUENCE: 14

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Leu Asp Ser
                 20                  25                  30

Asp Ala Lys Thr Tyr Leu Asn Trp Phe Gln Gln Arg Pro Gly Gln Ser
             35                  40                  45

Pro Arg Arg Leu Ile Tyr Leu Val Ser Lys Leu Asp Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Tyr Thr Phe Gly Gln Gly Thr Lys Leu Glu Ile Lys
            100                 105                 110
```

<210> SEQ ID NO 15
<211> LENGTH: 112
<212> TYPE: PRT
<213> ORGANISM: Homo sapiens

<400> SEQUENCE: 15

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Leu Asp Thr
                 20                  25                  30

Asp Ala Lys Thr Tyr Leu Asn Trp Phe Gln Gln Arg Pro Gly Gln Ser
             35                  40                  45

Pro Arg Arg Leu Ile Tyr Leu Val Ser Lys Leu Asp Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Tyr Thr Phe Gly Gln Gly Thr Lys Leu Glu Ile Lys
            100                 105                 110
```

<210> SEQ ID NO 16
<211> LENGTH: 112
<212> TYPE: PRT
<213> ORGANISM: Homo sapiens

<400> SEQUENCE: 16

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ala
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
            100                 105                 110

<210> SEQ ID NO 17
<211> LENGTH: 112
<212> TYPE: PRT
<213> ORGANISM: Homo sapiens

<400> SEQUENCE: 17

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Asn
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
            100                 105                 110

<210> SEQ ID NO 18
<211> LENGTH: 12
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa = citrulline

<400> SEQUENCE: 18

Ser Gly Xaa Gly Lys Gln Gly Gly Lys Ala Arg Ala
1               5                   10

<210> SEQ ID NO 19
<211> LENGTH: 23
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa = citrulline

```
<400> SEQUENCE: 19

Ser Gly Xaa Gly Lys Gly Gly Lys Gly Leu Gly Lys Gly Gly Ala Lys
1               5                   10                  15

Arg His Arg Lys Val Leu Arg
            20

<210> SEQ ID NO 20
<211> LENGTH: 12
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa = citrulline

<400> SEQUENCE: 20

Ser Gly Xaa Gly Lys Gly Gly Lys Gly Leu Gly Lys
1               5                   10

<210> SEQ ID NO 21
<211> LENGTH: 12
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa = citrulline

<400> SEQUENCE: 21

Gln Phe Pro Val Gly Xaa Val His Arg Leu Leu Arg
1               5                   10

<210> SEQ ID NO 22
<211> LENGTH: 12
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa = citrulline

<400> SEQUENCE: 22

Val His Arg Leu Leu Xaa Lys Gly Asn Tyr Ser Glu
1               5                   10

<210> SEQ ID NO 23
<211> LENGTH: 329
<212> TYPE: PRT
<213> ORGANISM: Homo sapiens

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 24
<211> LENGTH: 107
<212> TYPE: PRT
<213> ORGANISM: Homo sapiens

<400> SEQUENCE: 24

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 25
<211> LENGTH: 122
<212> TYPE: PRT
<213> ORGANISM: Mus musculus

<400> SEQUENCE: 25

Arg Ile Gln Leu Val Gln Ser Gly Pro Glu Leu Lys Lys Pro Gly Glu
1               5                   10                  15

Ala Val Lys Ile Ser Cys Lys Ala Ser Gly Tyr Thr Phe Thr Asn Tyr
            20                  25                  30

Gly Met His Trp Met Lys Gln Thr Pro Gly Lys Asp Phe Arg Trp Met
        35                  40                  45

Gly Trp Ile Asn Thr Tyr Ser Gly Glu Ala Thr Tyr Val Asp Asp Phe
    50                  55                  60

Lys Gly Arg Phe Ala Phe Ser Leu Gly Thr Ser Ala Ser Thr Ala Tyr
65                  70                  75                  80

Leu Gln Ile Asn Asn Leu Lys Asn Asp Asp Thr Ala Thr Tyr Phe Cys
                85                  90                  95

Leu Arg Gly Tyr Thr Tyr Gln Ser Phe Asp Glu Gly Gly Asp Tyr Trp
            100                 105                 110

Gly Gln Gly Thr Ala Leu Thr Val Ser Ser
        115                 120

<210> SEQ ID NO 26
<211> LENGTH: 122
<212> TYPE: PRT
<213> ORGANISM: Homo sapiens

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met His Trp Val Arg Gln Ala Pro Gly Gln Gly Leu Glu Trp Met
        35                  40                  45

Gly Trp Ile Asn Thr Tyr Ser Gly Glu Ala Thr Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Leu Arg Gly Tyr Thr Tyr Gln Ser Phe Asp Glu Gly Gly Asp Tyr Trp
            100                 105                 110

Gly Gln Gly Thr Leu Val Thr Val Ser Ser
        115                 120

<210> SEQ ID NO 27
<211> LENGTH: 122
<212> TYPE: PRT
<213> ORGANISM: Homo sapiens

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Gly Met His Trp Val Arg Gln Ala Pro Gly Gln Gly Leu Glu Trp Met
        35                  40                  45

Gly Trp Ile Asn Thr Tyr Ser Gly Glu Ala Thr Tyr Ala Gln Lys Phe
    50                  55                  60

```
Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Leu Arg Gly Tyr Thr Tyr Gln Ser Phe Asp Glu Gly Gly Asp Tyr Trp
                100                 105                 110

Gly Gln Gly Thr Leu Val Thr Val Ser Ser
                115                 120

<210> SEQ ID NO 28
<211> LENGTH: 122
<212> TYPE: PRT
<213> ORGANISM: Homo sapiens

<400> SEQUENCE: 28

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
                20                  25                  30

Gly Met His Trp Val Arg Gln Ala Pro Gly Gln Gly Leu Glu Trp Met
            35                  40                  45

Gly Trp Ile Asn Thr Tyr Ser Gly Glu Ala Thr Tyr Val Asp Asp Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Leu Arg Gly Tyr Thr Tyr Gln Ser Phe Asp Glu Gly Gly Asp Tyr Trp
                100                 105                 110

Gly Gln Gly Thr Leu Val Thr Val Ser Ser
                115                 120

<210> SEQ ID NO 29
<211> LENGTH: 122
<212> TYPE: PRT
<213> ORGANISM: Homo sapiens

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Gly Met His Trp Val Arg Gln Ala Pro Gly Gln Gly Leu Glu Trp Met
            35                  40                  45

Gly Trp Ile Asn Thr Tyr Ser Gly Glu Ala Thr Tyr Val Asp Asp Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Leu Arg Gly Tyr Thr Tyr Gln Ser Phe Asp Glu Gly Gly Asp Tyr Trp
                100                 105                 110

Gly Gln Gly Thr Leu Val Thr Val Ser Ser
                115                 120
```

```
<210> SEQ ID NO 30
<211> LENGTH: 112
<212> TYPE: PRT
<213> ORGANISM: Mus musculus

<400> SEQUENCE: 30

Asp Val Val Met Thr Gln Thr Pro Leu Thr Leu Ser Val Thr Thr Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Phe Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro Tyr Thr Phe Gly Gly Gly Thr Asn Leu Glu Ile Lys
            100                 105                 110

<210> SEQ ID NO 31
<211> LENGTH: 112
<212> TYPE: PRT
<213> ORGANISM: Homo sapiens

<400> SEQUENCE: 31

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
            100                 105                 110

<210> SEQ ID NO 32
<211> LENGTH: 112
<212> TYPE: PRT
<213> ORGANISM: Homo sapiens

<400> SEQUENCE: 32

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Trp Gln Gly
             85                  90                  95

Thr His Phe Pro Tyr Thr Phe Gly Gln Gly Thr Lys Leu Glu Ile Lys
            100                 105                 110

<210> SEQ ID NO 33
<211> LENGTH: 112
<212> TYPE: PRT
<213> ORGANISM: Homo sapiens

<400> SEQUENCE: 33

Asp Val Val Met Thr Gln Ser Pro Leu Ser Leu Pro Val Thr Leu Gly
1               5                  10                  15

Gln Pro Ala Ser Ile Ser Cys Arg Ser Ser Gln Ser Leu Val Ala Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
            100                 105                 110

<210> SEQ ID NO 34
<211> LENGTH: 112
<212> TYPE: PRT
<213> ORGANISM: Homo sapiens

<400> SEQUENCE: 34

Asp Val Val Met Thr Gln Ser Pro Leu Ser Leu Pro Val Thr Leu Gly
1               5                  10                  15

Gln Pro Ala Ser Ile Ser Cys Arg Ser Ser Gln Ser Leu Val Glu Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
            100                 105                 110

<210> SEQ ID NO 35
<211> LENGTH: 112
<212> TYPE: PRT
<213> ORGANISM: Homo sapiens

<400> SEQUENCE: 35

Asp Val Val Met Thr Gln Ser Pro Leu Ser Leu Pro Val Thr Leu Gly
1               5                  10                  15

Gln Pro Ala Ser Ile Ser Cys Arg Ser Ser Gln Ser Leu Val Ser Ser
            20                  25                  30

```
Asp Gly Lys Thr Tyr Leu Asn Trp Phe Gln Gln Arg Pro Gly Gln Ser
            35                  40                  45

Pro Arg Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Tyr Thr Phe Gly Gln Gly Thr Lys Leu Glu Ile Lys
            100                 105                 110

<210> SEQ ID NO 36
<211> LENGTH: 11
<212> TYPE: PRT
<213> ORGANISM: Artificial sequence
<220> FEATURE:
<223> OTHER INFORMATION: CDR1 of msVL22.101 and hVL22.101g

<400> SEQUENCE: 36

Gln Ser Leu Leu Asp Ser Asp Gly Lys Thr Tyr
1               5                   10

<210> SEQ ID NO 37
<211> LENGTH: 11
<212> TYPE: PRT
<213> ORGANISM: Homo sapiens

<400> SEQUENCE: 37

Gln Ser Leu Val Asp Ser Asp Gly Lys Thr Tyr
1               5                   10

<210> SEQ ID NO 38
<211> LENGTH: 11
<212> TYPE: PRT
<213> ORGANISM: Homo sapiens

<400> SEQUENCE: 38

Gln Ser Leu Val Ala Ser Asp Gly Lys Thr Tyr
1               5                   10

<210> SEQ ID NO 39
<211> LENGTH: 11
<212> TYPE: PRT
<213> ORGANISM: Homo sapiens

<400> SEQUENCE: 39

Gln Ser Leu Val Glu Ser Asp Gly Lys Thr Tyr
1               5                   10

<210> SEQ ID NO 40
<211> LENGTH: 11
<212> TYPE: PRT
<213> ORGANISM: Homo sapiens

<400> SEQUENCE: 40

Gln Ser Leu Val Ser Ser Asp Gly Lys Thr Tyr
1               5                   10

<210> SEQ ID NO 41
<211> LENGTH: 11
<212> TYPE: PRT
<213> ORGANISM: Homo sapiens
```

<400> SEQUENCE: 41

Gln Ser Leu Leu Glu Ser Asp Gly Lys Thr Tyr
1               5                   10

<210> SEQ ID NO 42
<211> LENGTH: 11
<212> TYPE: PRT
<213> ORGANISM: Homo sapiens

<400> SEQUENCE: 42

Gln Ser Leu Leu Asp Ser Glu Gly Lys Thr Tyr
1               5                   10

<210> SEQ ID NO 43
<211> LENGTH: 11
<212> TYPE: PRT
<213> ORGANISM: Homo sapiens

<400> SEQUENCE: 43

Gln Ser Leu Leu Asp Ser Ser Gly Lys Thr Tyr
1               5                   10

<210> SEQ ID NO 44
<211> LENGTH: 11
<212> TYPE: PRT
<213> ORGANISM: Homo sapiens

<400> SEQUENCE: 44

Gln Ser Leu Leu Glu Ser Glu Gly Lys Thr Tyr
1               5                   10

<210> SEQ ID NO 45
<211> LENGTH: 11
<212> TYPE: PRT
<213> ORGANISM: Homo sapiens

<400> SEQUENCE: 45

Gln Ser Leu Leu Glu Ser Ser Gly Lys Thr Tyr
1               5                   10

<210> SEQ ID NO 46
<211> LENGTH: 11
<212> TYPE: PRT
<213> ORGANISM: Homo sapiens

<400> SEQUENCE: 46

Gln Ser Leu Leu Glu Ser Asp Ala Lys Thr Tyr
1               5                   10

<210> SEQ ID NO 47
<211> LENGTH: 11
<212> TYPE: PRT
<213> ORGANISM: Homo sapiens

<400> SEQUENCE: 47

Gln Ser Leu Leu Asp Thr Glu Gly Lys Thr Tyr
1               5                   10

<210> SEQ ID NO 48
<211> LENGTH: 11
<212> TYPE: PRT
<213> ORGANISM: Homo sapiens

```
<400> SEQUENCE: 48

Gln Ser Leu Leu Asp Thr Ser Gly Lys Thr Tyr
1               5                   10

<210> SEQ ID NO 49
<211> LENGTH: 11
<212> TYPE: PRT
<213> ORGANISM: Homo sapiens

<400> SEQUENCE: 49

Gln Ser Leu Leu Asp Ser Ala Gly Lys Thr Tyr
1               5                   10

<210> SEQ ID NO 50
<211> LENGTH: 11
<212> TYPE: PRT
<213> ORGANISM: Homo sapiens

<400> SEQUENCE: 50

Gln Ser Leu Leu Glu Ser Ala Gly Lys Thr Tyr
1               5                   10

<210> SEQ ID NO 51
<211> LENGTH: 11
<212> TYPE: PRT
<213> ORGANISM: Homo sapiens

<400> SEQUENCE: 51

Gln Ser Leu Leu Asp Ala Glu Gly Lys Thr Tyr
1               5                   10

<210> SEQ ID NO 52
<211> LENGTH: 11
<212> TYPE: PRT
<213> ORGANISM: Homo sapiens

<400> SEQUENCE: 52

Gln Ser Leu Leu Asp Asn Glu Gly Lys Thr Tyr
1               5                   10

<210> SEQ ID NO 53
<211> LENGTH: 17
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa = citrulline

<400> SEQUENCE: 53

Glu Pro Thr Asp Ser Leu Asp Ala Xaa Gly His Arg Pro Val Asp Arg
1               5                   10                  15

Arg

<210> SEQ ID NO 54
<211> LENGTH: 15
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa = citrulline
<220> FEATURE:
<221> NAME/KEY: MISC_FEATURE
<222> LOCATION: (9)..(9)
<223> OTHER INFORMATION: Xaa = citrulline
```

```
<220> FEATURE:
<221> NAME/KEY: MISC_FEATURE
<222> LOCATION: (11)..(11)
<223> OTHER INFORMATION: Xaa = citrulline

<400> SEQUENCE: 54

Tyr Val Thr Xaa Ser Ser Ala Val Xaa Leu Xaa Ser Ser Val Pro
 1               5                  10                  15

<210> SEQ ID NO 55
<211> LENGTH: 7
<212> TYPE: PRT
<213> ORGANISM: Artificial sequence
<220> FEATURE:
<223> OTHER INFORMATION: Region around CDR2 of msVL22.101 and
      hVL22.101(LC)y

<400> SEQUENCE: 55

Leu Val Ser Lys Leu Asp Ser
 1               5

<210> SEQ ID NO 56
<211> LENGTH: 330
<212> TYPE: PRT
<213> ORGANISM: Homo sapiens

<400> SEQUENCE: 56

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305             310                 315                 320

Gln Lys Ser Leu Ser Leu Ser Pro Gly Lys
            325                 330

<210> SEQ ID NO 57
<211> LENGTH: 11
<212> TYPE: PRT
<213> ORGANISM: Artificial sequence
<220> FEATURE:
<223> OTHER INFORMATION: Consensus sequence for VL CDR1
<220> FEATURE:
<221> NAME/KEY: MISC_FEATURE
<222> LOCATION: (4)..(4)
<223> OTHER INFORMATION: Xaa = Val or Leu
<220> FEATURE:
<221> NAME/KEY: MISC_FEATURE
<222> LOCATION: (6)..(6)
<223> OTHER INFORMATION: Xaa = Thr, Ser, Ala or Asn
<220> FEATURE:
<221> NAME/KEY: MISC_FEATURE
<222> LOCATION: (8)..(8)
<223> OTHER INFORMATION: Xaa = Gly or Ala

<400> SEQUENCE: 57

Gln Ser Leu Xaa Asp Xaa Asp Xaa Lys Thr Tyr
1               5                   10

<210> SEQ ID NO 58
<211> LENGTH: 11
<212> TYPE: PRT
<213> ORGANISM: Artificial sequence
<220> FEATURE:
<223> OTHER INFORMATION: Consensus sequence for VL CDR1
<220> FEATURE:
<221> NAME/KEY: MISC_FEATURE
<222> LOCATION: (4)..(4)
<223> OTHER INFORMATION: Xaa = Val or Leu
<220> FEATURE:
<221> NAME/KEY: MISC_FEATURE
<222> LOCATION: (5)..(5)
<223> OTHER INFORMATION: Xaa = Asp or Glu
<220> FEATURE:
<221> NAME/KEY: MISC_FEATURE
<222> LOCATION: (6)..(6)
<223> OTHER INFORMATION: Xaa = Thr, Ser, Ala or Asn
<220> FEATURE:
<221> NAME/KEY: MISC_FEATURE
<222> LOCATION: (7)..(7)
<223> OTHER INFORMATION: Xaa = Asp, Glu, Ser or Ala
<220> FEATURE:
<221> NAME/KEY: MISC_FEATURE
<222> LOCATION: (8)..(8)
<223> OTHER INFORMATION: Xaa = Gly or Ala

<400> SEQUENCE: 58

Gln Ser Leu Xaa Xaa Xaa Xaa Xaa Lys Thr Tyr
1               5                   10
```

ANTIBODIES BINDING TO CITRULLINATED HISTONE 2A AND/OR 4

CROSS REFERENCE TO RELATED APPLICATIONS

This application is a continuation of U.S. application Ser. No. 17/269,509, filed Feb. 18, 2021, which is a national stage application under 35 U.S.C. § 371 of International Application No. PCT/EP2019/072302, filed internationally on Aug. 20, 2019, which claims priority to Great Britain Patent Application 1813597.0 filed Aug. 21, 2018 and Great Britain Patent Application 1900983.6 filed Jan. 24, 2019, the contents of which are incorporated herein by reference in their entirety.

INCORPORATION BY REFERENCE OF SEQUENCE LISTING

The present application is being filed along with a Sequence Listing in electronic format. The Sequence Listing is provided as a file entitled 251502012201SeqList.txt, created Nov. 18, 2021, which is 34,250 bytes in size. The information in the electronic format of the Sequence Listing is incorporated by reference in its entirety.

FIELD OF THE INVENTION

The invention provides antibodies or binding fragments thereof directed against citrulline-containing epitopes. The antibodies or binding fragments thereof of the invention can be used in therapy, for example in the treatment or prevention of Neutrophil Extracellular Trap (NET)-associated pathologies. The antibodies or binding fragments thereof of the invention can be used in the treatment or prevention of NET-associated pathologies such as systemic lupus erythematosus (SLE), lupus, sepsis, vasculitis, inflammatory arthritis, rheumatoid arthritis and osteoarthritis, psoriasis, Alzheimer's disease, autoimmune hepatitis, juvenile idiopathic arthritis, Sjögren's disease, Anti-phospholipid Syndrome, Bechet's disease, spondylitis, spondyloarthropathy, multiple system atrophy, Parkinson's disease, Lewy body dementia asthma, allergic rhinovirus exacerbated asthma, allergic asthma, cystic fibrosis, fibrosis and idiopathic pulmonary fibrosis, dry eye disease, uveitis, nongranulomatous uveitis, granulomatous uveitis, dermatitis, atopic dermatitis, COPD, bronchitis, or other NET-associated pathologies such as wound healing in diabetes, cancer, cancer metastasis, and transplant organ health in vivo or ex vivo. The invention also provides pharmaceutical compositions and methods for treating or preventing NET-associated pathologies such as SLE, lupus, sepsis, vasculitis, inflammatory arthritis, rheumatoid arthritis and osteoarthritis, psoriasis, Alzheimer's disease, autoimmune hepatitis, juvenile idiopathic arthritis, Sjögren's disease, Anti-phospholipid Syndrome, Bechet's disease, spondylitis, spondyloarthropathy, multiple system atrophy, Parkinson's disease, Lewy body dementia asthma, allergic rhinovirus exacerbated asthma, allergic asthma, cystic fibrosis, fibrosis and idiopathic pulmonary fibrosis, dry eye disease, uveitis, nongranulomatous uveitis, granulomatous uveitis, dermatitis, atopic dermatitis, COPD, bronchitis, or other NET-associated pathologies such as wound healing in diabetes, cancer, cancer metastasis, and transplant organ health in vivo or ex vivo.

BACKGROUND OF THE INVENTION

Inflammatory conditions, whether of a chronic or acute nature, represent a substantial problem in the healthcare industry. Briefly, chronic inflammation is considered to be inflammation of a prolonged duration (weeks or months) in which active inflammation, tissue destruction and attempts at healing are proceeding simultaneously. Although chronic inflammation can follow an acute inflammatory episode, it can also begin as an insidious process that progresses with time, for example, as a result of a persistent infection (e.g., tuberculosis, syphilis, fungal infection) that causes a delayed hypersensitivity reaction, prolonged exposure to endogenous (e.g., elevated plasma lipids) or exogenous (e.g., silica, asbestos, cigarette tar, surgical sutures) toxins, or autoimmune reactions against the body's own tissues (e.g., rheumatoid arthritis, systemic lupus erythematosus, vasculitis, multiple sclerosis, psoriasis).

One consequence of inflammation is the formation of Neutrophil Extracellular Traps (NETs). NETs are also known to cause inflammation. NETs are structures comprising DNA and histones that are produced by neutrophils as part of the host defense mechanism against pathogens. They can trap and kill various bacterial, fungal, viral and protozoal pathogens, and their release is one of the first lines of defense against pathogens. Following activation by microorganisms or cytokines, histones become hypercitrullinated and the neutrophil nucleus undergoes a process of chromatin decondensation that leads to the formation of NETs by NETosis, a form of neutrophil cell death.

NETs play a pathological role in a variety of diseases, for example by causing aberrant inflammation. Thus, NETs are involved in the pathology of a variety of inflammatory conditions, such as systemic lupus erythematosus (SLE), lupus, sepsis, vasculitis, inflammatory arthritis, rheumatoid arthritis and osteoarthritis, psoriasis, Alzheimer's disease, autoimmune hepatitis, juvenile idiopathic arthritis, Bechet's disease, spondylitis, spondyloarthropathy, multiple system atrophy, Parkinson's disease, Lewy body dementia asthma, allergic rhinovirus exacerbated asthma, cystic fibrosis and idiopathic pulmonary fibrosis.

For example, NETs can cause autoantigen exposure to the extracellular space and the subsequent production of pathological autoantibodies by the subject. Furthermore, NETs and NET remnants harbor toxic histones, which induce vascular damage and subsequent organ damage and failure. Thus, in such diseases, interfering with NET formation, and inducing clearance of NETs and NET remnants from circulation and tissues, would have therapeutic benefits.

Neutrophils are also increasingly being recognized as an important element in tumour progression. They have been shown to exert important effects at nearly every stage of tumour progression with a number of studies demonstrating that their presence is critical to tumour development. Studies have also implicated NETs as facilitators of tumour progression and metastasis. It has also been shown that neutrophils, through the generation of NETs, provide a scaffold and a stimulus for platelet adhesion, thrombus formation and coagulation in tumours.

In addition, NETs have been implicated in reducing organ health after transplant. NETs contribute to primary graft dysfunction, contributing to early mortality after lung transplantation. It has been shown that NETs play a pathogenic role in solid organ transplantation.

Thus, identifying therapeutic agents that could block NET formation, clear NETs, and/or prevent NETosis would have clinical benefit in inflammatory diseases such as inflammatory arthritis, rheumatoid arthritis and osteoarthritis, and other NET-associated pathologies such as systemic lupus erythematosus (SLE), lupus, sepsis, vasculitis, psoriasis, Alzheimer's disease, autoimmune hepatitis, juvenile idiopathic arthritis, Sjögren's disease, Anti-phospholipid Syndrome, Bechet's disease, spondylitis, spondyloarthropathy, multiple system atrophy, Parkinson's disease, Lewy body dementia asthma, allergic rhinovirus exacerbated asthma, allergic asthma, cystic fibrosis, fibrosis and idiopathic pulmonary fibrosis, dry eye disease, uveitis, nongranulomatous uveitis, granulomatous uveitis, dermatitis, atopic dermatitis, COPD, bronchitis, wound healing in diabetes, cancer, cancer metastasis, and transplant organ health in vivo or ex vivo.

There remains a need for compounds for the treatment or prevention of NET-associated pathologies.

Antibodies that bind to citrullinated epitopes on deiminated human histone 2A and histone 4 are described in WO2009147201, WO2011070172 and WO2016092082.

SUMMARY OF THE INVENTION

The present inventors have created improved antibodies that bind to citrullinated epitopes on the amino terminus of histones 2A and/or histone 4. These antibodies can be used to treat diseases or pathologies associated with citrullination, such as NET-associated pathologies and inflammatory conditions.

The present inventors have created antibodies that show improved properties over the therapeutic antibodies disclosed in WO2009147201, WO2011070172 and WO2016092082. The inventors discovered, by accelerated stability testing and Mass Spectrometry analyses, that isomerization of certain amino acid residues in the Complementarity-Determining Region 1 (CDR1) of the light chain of the antibodies disclosed in WO2009147201, WO2011070172 and WO2016092082 resulted in a reduction of the binding affinity of the antibodies for the tested histone-derived peptides over time. The inventors then conducted a thorough analysis of CDR1 light chain mutants to solve the isomerization problem, whilst attempting to retain the binding properties of the antibody. Several attempts resulted in antibodies with reduced binding affinity for the target peptides.

Finally, the inventors were successful in identifying a group of mutations in CDR1 of the light chain that removed the isomerization issue, whilst maintaining the binding properties of the original antibody. Surprisingly, the mutant antibodies showed improved properties over the original antibodies both in vitro and in vivo.

Therefore, the present invention provides:
An antibody or binding fragment thereof that specifically binds to a citrullinated epitope on deiminated human histone 2A and/or histone 4, wherein the antibody or binding fragment thereof comprises:
a) CDR1 of the light chain variable domain (VL), wherein the CDR comprises or consists of the amino acid sequence QSL-$X_1$-D-$X_2$-D-$X_3$-KTY, wherein $X_1$ is V or L, $X_2$ is T, S, A or N and $X_3$ is G or A (SEQ ID NO:57), provided that the amino acid sequence is not QSLLDSDGKTY (SEQ ID NO: 36) or QSLVDSDGKTY (SEQ ID NO: 37); and
b) at least one CDR selected from SEQ ID NOs: 1 to 5.

The invention also provides:
An antibody or binding fragment thereof that specifically binds to a citrullinated epitope on deiminated human histone 2A and/or histone 4, wherein the antibody or binding fragment thereof comprises the CDRs of:
a) the CDR1 of SEQ ID NOs: 13, 14, 15, 16 or 17; and
b) the heavy chain variable domain amino acid sequence of SEQ ID NO: 11 or 12.

The invention also provides:
A polynucleotide encoding the antibody or binding fragment thereof as defined herein, a cloning or expression vector comprising said polynucleotide, or a host cell comprising said cloning or expression vector.

The invention also provides:
A process for the production of an antibody or binding fragment thereof that specifically binds to a citrullinated epitope on deiminated human histone 2A and/or histone 4, comprising culturing the host cell as defined herein and isolating the antibody or binding fragment thereof from said cell.

The invention also provides:
A pharmaceutical composition comprising the antibody or binding fragment thereof according as defined herein and at least one pharmaceutically acceptable diluent or carrier.

The invention also provides:
The antibody or binding fragment thereof as defined herein, or the pharmaceutical composition as defined herein, for use in therapy.

The invention also provides:
The antibody or binding fragment thereof as defined herein, or the pharmaceutical composition as defined herein, for use in a method of treating or preventing a NET-associated pathology.

The invention also provides:
A method of treating a patient comprising administering a therapeutically effective amount of an antibody or binding fragment thereof as defined herein or the pharmaceutical composition as defined herein, to said patient.

BRIEF DESCRIPTION OF THE SEQUENCE LISTING

Antibody Nomenclature

CDR=complementarity-determining region.
VH=heavy chain variable domain.
VL=light chain variable domain.
CH=heavy chain constant domain.
CL=light chain constant domain.
msVH22.101=mouse VH of therapeutic antibody.
msVL22.101=mouse VL of therapeutic antibody.
hVH22.101x=humanized VH of therapeutic antibody, 'x' refers to the heavy chain.
hVL22.101y=humanized VL of therapeutic antibody, 'y' refers to the light chain.
hVH22.101(HC)x=optimized humanized VH of therapeutic antibody, '(HC)x' refers to the heavy chain.
hVL22.101(LC)y=optimized humanized VL of therapeutic antibody, '(LC)y' refers to the light chain.
hMQ22.101x/y=humanized therapeutic antibody, 'x' refers to the heavy chain, 'y' refers to the light chain.
hMQ22.101(HC)x/(LC)y=optimized humanized therapeutic antibody of the invention, '(HC)x' refers to the heavy chain, '(LC)y' refers to the light chain.

| SEQ ID NO | Protein | Name |
|---|---|---|
| 1 | protein | CDR1 of msVH22.101 and hVH22.101(HC)x |
| 2 | protein | CDR2 of msVH22.101 and hVH22.101(HC)x |
| 3 | protein | CDR3 of msVH22.101 and hVH22.101(HC)x |
| 4 | protein | CDR2 of msVL22.101 and hVL22.101(LC)y |

-continued

| SEQ ID NO | Protein | Name |
|---|---|---|
| 5 | protein | CDR3 of msVL22.101 and hVL22.101(LC)y |
| 6 | protein | CDR1 of hVL22.101LC17 |
| 7 | protein | CDR1 of hVL22.101LC21 |
| 8 | protein | CDR1 of hVL22.101LC27 |
| 9 | protein | CDR1 of hVL22.101LC41 |
| 10 | protein | CDR1 of hVL22.101LC42 |
| 11 | protein | hVH22.101f |
| 12 | protein | hVH22.101HC9 |
| 13 | protein | hVL22.101LC17 |
| 14 | protein | hVL22.101LC21 |
| 15 | protein | hVL22.101LC27 |
| 16 | protein | hVL22.101LC41 |
| 17 | protein | hVL22.101LC42 |
| 18 | protein | SEQ ID NO 1 from WO2016092082-Example 1, histone 2A |
| 19 | protein | SEQ ID NO 2 from WO2016092082, histone 4 |
| 20 | protein | Shortened SEQ ID NO 2 from WO2016092082-Example 7, histone 4 |
| 21 | protein | Peptide no 4 (human histone 2A) (SEQ ID NO 24 from WO2011070172) |
| 22 | protein | Peptide no 6 (human histone 2A) (SEQ ID NO 26 from WO2011070172) |
| 23 | protein | Human heavy chain constant domain of IgG1 |
| 24 | protein | Human kappa chain constant domain |
| 25 | protein | msVH22.101 |
| 26 | protein | hVH22.101j |
| 27 | protein | hVH22.101HC7 |
| 28 | protein | hVH22.101HC8 |
| 29 | protein | hVH22.101HC10 |
| 30 | protein | msVL22.101 |
| 31 | protein | hVL22.101e |
| 32 | protein | hVL22.101g |
| 33 | protein | hVL22.101h |
| 34 | protein | hVL22.101i |
| 35 | protein | hVL22.101j |
| 36 | protein | CDR1 of msVL22.101 and hVL22.101g |
| 37 | protein | CDR1 of hVL22.101e |
| 38 | protein | CDR1 of hVL22.101h |
| 39 | protein | CDR1 of hVL22.101i |
| 40 | protein | CDR1 of hVL22.101j |
| 41 | protein | CDR1 of hVL22.101LC16 |
| 42 | protein | CDR1 of hVL22.101LC19 |
| 43 | protein | CDR1 of hVL22.101LC20 |
| 44 | protein | CDR1 of hVL22.101LC22 |
| 45 | protein | CDR1 of hVL22.101LC23 |
| 46 | protein | CDR1 of hVL22.101LC24 |
| 47 | protein | CDR1 of hVL22.101LC25 |
| 48 | protein | CDR1 of hVL22.101LC26 |
| 49 | protein | CDR1 of hVL22.101LC37 |
| 50 | protein | CDR1 of hVL22.101LC38 |
| 51 | protein | CDR1 of hVL22.101LC39 |
| 52 | protein | CDR1 of hVL22.101LC40 |
| 53 | protein | msFibβ XG (SEQ ID NO 37 from WO2011070172) |
| 54 | protein | msVim XS/XL (SEQ ID NO 38 from WO2011070172) |
| 55 | Protein | Region around CDR2 of msVL22.101 and hVL22.101(LC)y |
| 56 | Protein | Heavy chain constant domain of hCH22.101f |

BRIEF DESCRIPTION OF THE FIGURES

FIG. 1: Accelerated stability testing of hMQ22.101j/e and hMQ22.101f/g 0.75 ml Aliquot (glass tubes) containing hMQ22.101j/e (12.5 mg/ml) or hMQ22.101f/g (3.31 mg/ml) in 25 mM Tris-HCl, pH 8.0 were stored at 37° C. each for 8 weeks. Each week several 10 µl and 20 µl samples were withdrawn from each glass tube under aseptic conditions and stored at −80° C. until further analysis (ELISA and mass spectrometry). hMQ22.101j/e samples from week 0, 2, 4, 6 and 8, and hMQ22.101f/g samples from week 0, 3 and 6 were subjected to an in house-validated CMC ELISA in which binding to a histone-derived peptide (SEQ ID NO: 18) was assessed.

The antibody binding affinity from the week 0 accelerated stability sample was set at 100%, and all other binding affinity values of the accelerated stability samples (week 2, 3, 4, 6 and 8) were recalculated as a percentage of week 0 (100%) and plotted as a bar graph.

Figures 2A, 2B, 2C:
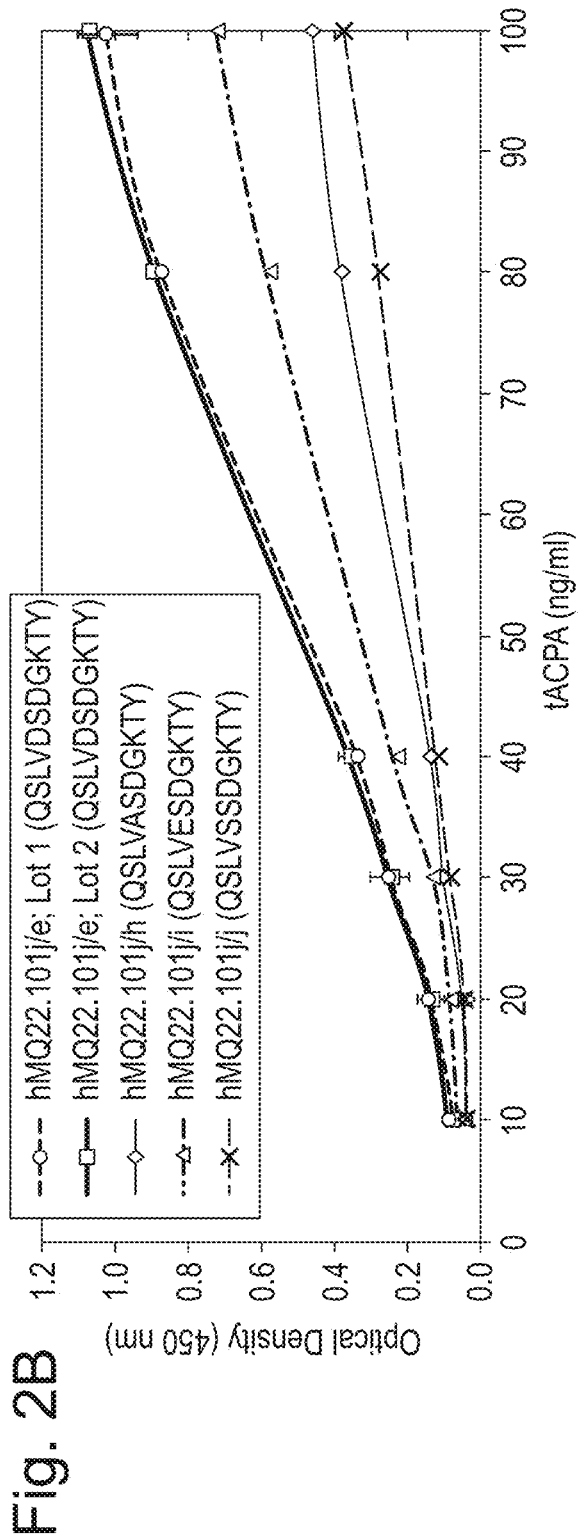

FIGS. 2A-2C: Mass spectrometry analysis of hMQ22.101x/y antibodies a) FIG. 2A: Mass spectrometry (MS) analysis of accelerated stability samples from antibody hMQ22.101j/e.

0.75 ml Aliquot (glass tubes) containing hMQ22.101j/e (12.5 mg/ml) were stored at 37° C. each for 8 weeks. Each week a sample was withdrawn from each glass tube under aseptic conditions and stored at −80° C. until MS analysis.

The MS analysis was performed as described in Example 2. The table shows the relative aspartate (D) isomerization levels within the CDR1 and near the CDR2 of hVL22.101e.

b) FIG. 2B: Antigen binding assay with humanized antibodies, which contain an aspartate-mutated CDR1 of hVL22.101y.

Generated CDR1 aspartate-mutated antibodies hMQ22.101j/h, hMQ22.101j/i and hMQ22.101j/j were compared to the aspartate-containing antibody hMQ22.101j/e using an in house-validated CMC ELISA as described in Example 1. The graph shows the optical density results of the three hVL22.101y CDR1 mutants (CDR1 of hVL22.101h=mutation of DS site to AS; CDR1 of hVL22.101i=mutation of DS site to ES; CDR1 of hVL22.101j=mutation of DS site to SS).

c) FIG. 2C: MS analysis of accelerated stability samples from antibody hMQ22.101j/i. The MS analysis was performed as described in Example 2. The table shows the relative aspartate (D) isomerization levels within the CDR1 and near the CDR2 of hVL22.101i.

FIGS. 3A-3B: Generation and affinity analysis of hMQ22.101 isomerization mutants a) FIG. 3A: Table shows seventeen CDR1-mutated domains of hVL22.101(LC)y, which have been created as well as the un-mutated CDR1 of hVL22.101e and hVL22.101g.

b) FIG. 3A: Graph showing dissociation rates ($k_{dis}$×E-07 (1/s)) of isomerization mutants to citrullinated H2A-derived peptide (SEQ ID NO: 18) and H4-derived peptide (SEQ ID NO: 20) as measured with the Octet® RED96 (biomolecule detection system) instrument. A lower dissociation rate indicates higher affinity of the antibody for the antigen.

FIG. 4: Accelerated stability testing of hMQ22.101 isomerization mutants 0.4 ml Aliquots (glass tubes) containing the indicated mutated antibodies (ranging from 2.06-4.29 mg/ml) were stored at 37° C. each for 6 weeks. Each week a sample was withdrawn from each glass tube under aseptic conditions and stored at −80° C. until further analysis. Samples from week 0, 3 and 6 were subjected to an in house-validated CMC ELISA in which binding to citrullinated H2A-derived peptide (SEQ ID NO: 18) was assessed.

The recalculated antibody binding affinity from the week 0 accelerated stability sample was set at 100%, and all other binding affinity values of the accelerated stability samples were recalculated as a percentage of week 0 (100%) and plotted as a bar graph.

Preferred heavy chains used in the accelerated stability tests were hVH22.101f and hVH22.101HC9. Nine combinations of heavy chains and the CDR1-mutated light chains were tested. hMQ22.101f/LC41, hMQ22.101f/LC42, hMQ22.101HC9/LC21, hMQ22.101HC9/LC27 and hMQ22.101HC9/LC42 showed the greatest stability after 6 weeks.

FIG. 5: Mass spectrometry analysis of hMQ22.101 isomerization mutants 0.4 ml Aliquots (glass tubes) containing the indicated mutated antibodies (ranging from 2.06-4.29 mg/ml) were stored at 37° C. each for 6 weeks. Each week a sample was withdrawn from each glass tube under aseptic conditions and stored at −80° C. until further analysis. Mass spectrometry (MS) analysis of VL CDR1-mutated hMQ22.101 antibodies (isomerization mutants) was performed as described in Example 2, with the difference that accelerated stability samples from week 0 and 6 were used and compared to isomerization levels of hMQ22.101j/e. The table shows the relative aspartate (D) isomerization levels within the CDR1 of hVL22.101(LC)y. MS analysis of hMQ22.101 isomerization mutants indicate that hMQ22.101f/LC41 showed the least isomerization over time (0.5%) and thus was the most preferred candidate. Other preferred candidates were hMQ22.101f/LC42 and hMQ22.101HC9/LC42.

FIG. 6: Aggregation and degradation assays of preferred hMQ22.101 isomerization mutants 0.4 ml Aliquots (glass tubes) containing the indicated mutated antibodies (ranging from 2.06-4.29 mg/ml) were stored at 37° C. each for 6 weeks. Each week a sample was withdrawn from each glass tube under aseptic conditions and stored at −80° C. until further analysis. Stability samples from week 0 and 6 were used from the hMQ22.101f/LC41, hMQ22.101f/LC42 and hMQ22.101HC9/LC42 isomerization mutants for aggregation and degradation analysis as described in Example 10. Measurements were carried out on an Agilent™ 1200 system in combination with an Agilent Zorbax® GF-250 gel filtration column. Proteins have been detected using 240 nm UV-light. Main antibody peak was detected at approximately 4.25 minutes. Shoulders before and after the main peak were quantified and are a measure of the percentage aggregation and degradation levels, respectively. hMQ22.101f/LC41, hMQ22.101f/LC42 and hMQ22.101HC9/LC42 showed acceptable aggregation and degradation profiles, indicating that they are acceptable for further development.

FIG. 7: NETosis inhibition experiments using preferred isomerization mutants hMQ22.101f/LC41 and hMQ22.101f/LC42

Neutrophils from healthy volunteers (donor 154 and 155) were stimulated during 4 hours with calcium ionophore A23187. The effect of neutrophil extracellular trap (NET)-reducing antibodies was tested by adding antibodies at a concentration of 25 µg/ml or assay buffer 15 min prior to adding A23187 to the cells. After 4 hours of incubation at 37° C. and 5% $CO_2$, cells were washed and extracellular DNA subsequently digested with S7 nuclease. NET fragments were harvested from the wells and quantified by measuring the MPO activity in the sample by adding 50 µl 3,3',5,5'-Tetramethylbenzidine (TMB) substrate to 50 µl harvested NETs. After an incubation of 10 min at RT 50 µl $H_2SO_4$ was added and optical density measured at 450 nm. Background signals coming from neutrophils, which have not been subjected to A23187 treatment, were subtracted and signals from A23187+non-related antibody-treated neutrophils were set at 100%. Signals from all other treated groups were set as percentage of the non-related antibody treatment.

Figure 8:
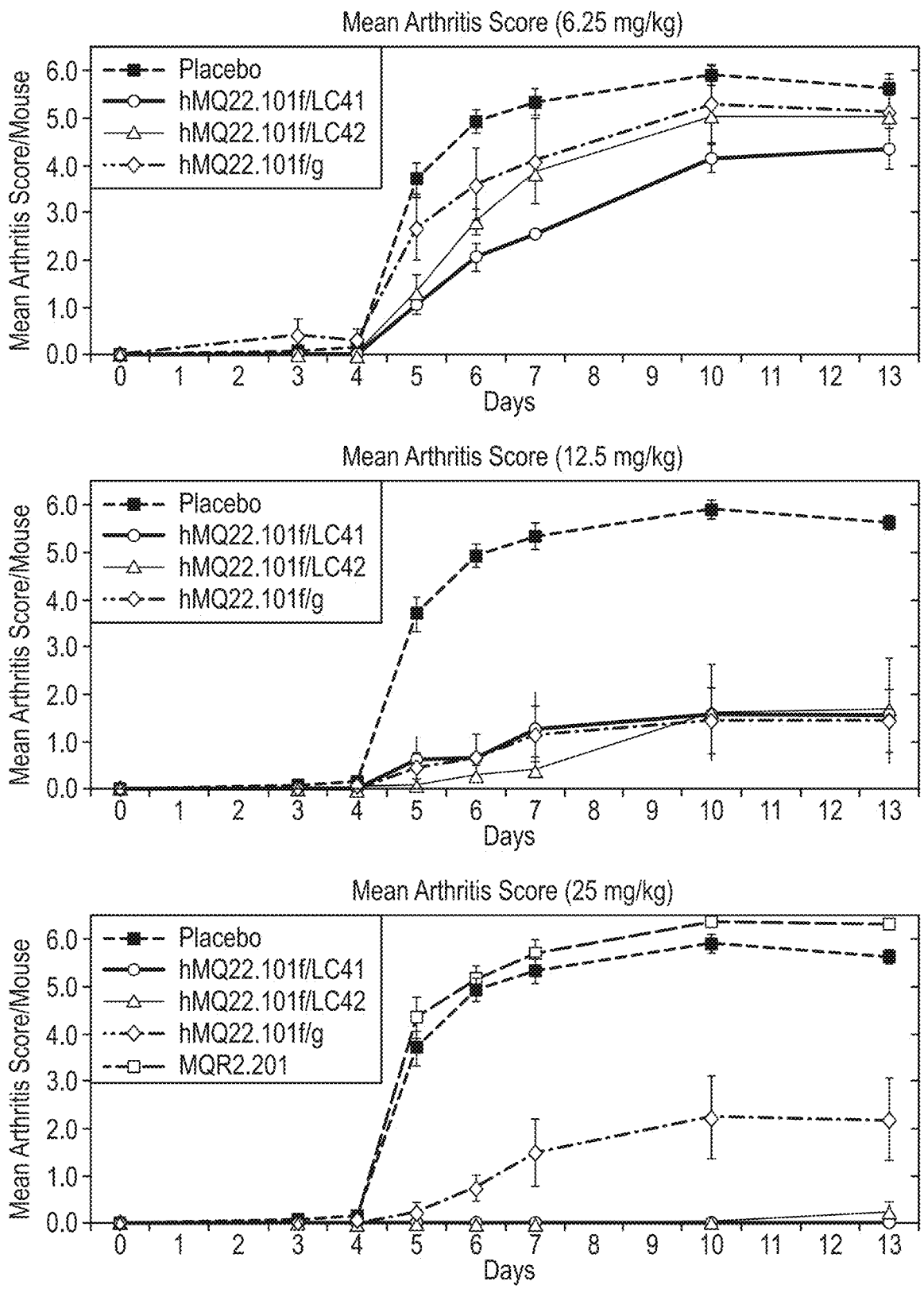

FIG. 8: hMQ22.101f/LC41, hMQ22.101f/LC42 and hMQ22.101f/g dose response in a mouse CAIA model Lead-optimized candidate antibodies prevent the onset of inflammation. A collagen antibody induced arthritis (CAIA) model was used to test the dose response efficacy of hMQ22.101f/LC41, hMQ22.101f/LC42 or hMQ22.101f/g. Groups of 5 mice were treated on day 0 through i.p. injection with 2.8 mg anti-collagen-II antibodies. LPS (25 µg/mouse) was injected i.p. on day 3, simultaneously with hMQ22.101f/LC41, hMQ22.101f/LC42 or hMQ22.101f/g; each at 6.25, 12.5 and 25 mg/kg, non-related isotype-matched control antibody (MQR2.201 at 25 mg/kg) or without antibody (placebo). The degree of swelling in the paws was scored for 2 weeks and depicted in the graphs as "Mean Arthritis Score/mouse".

Figure 9A:
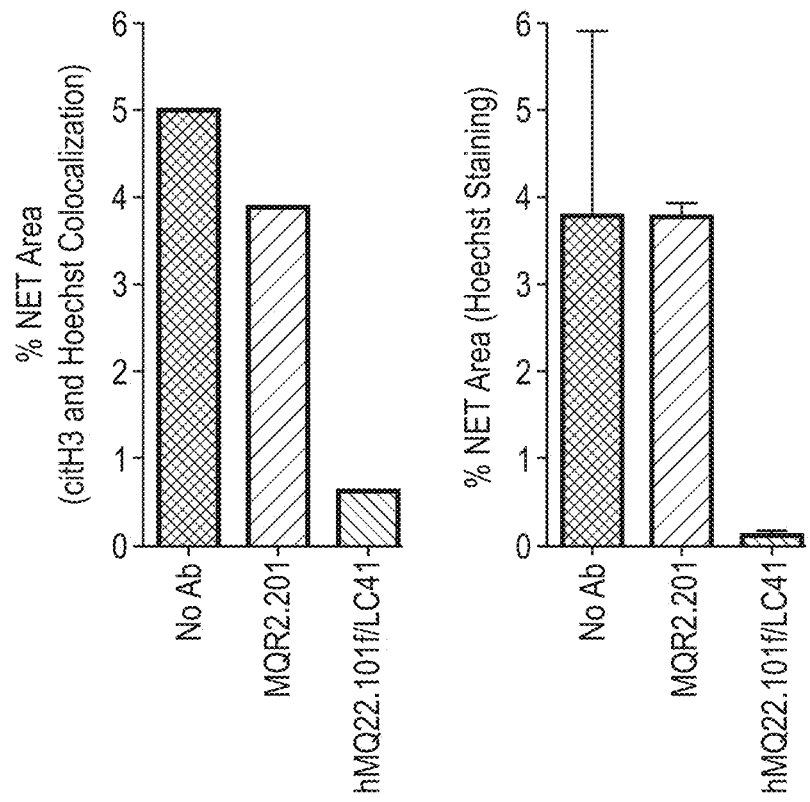
Figure 9B:
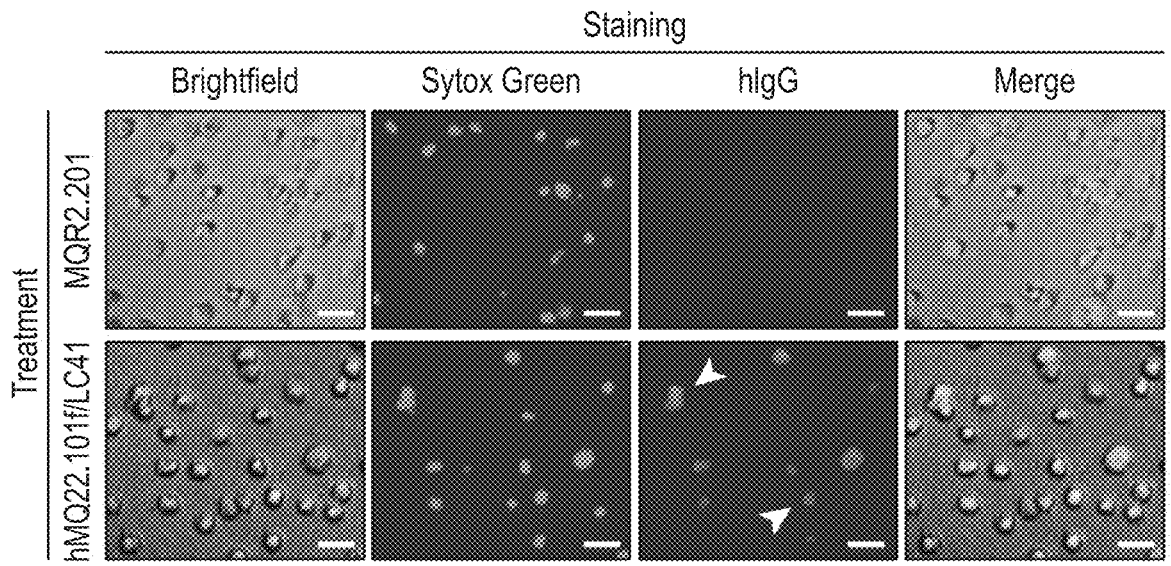

FIGS. 9A-9B: in vitro NET inhibition and binding of NETs by hMQ22.101f/LC41 Bone marrow-derived mouse neutrophils were stimulated with A23187 to induce NET release in vitro. NET release was inhibited by hMQ22.101f/LC41, but not with MQR2.201 (FIG. 9A; Left bar graph, quantification of Hoechst (DNA) and citrullinated Histone 3 (citH3) colocalization, and right bar graph, quantification of only Hoechst). In addition, hMQ22.101f/LC41 binds to expelled NETs (yellow arrow) as well as pre-NETs (white arrow), which could be the first step towards NET clearance by macrophages (FIG. 9B). Sytox™ Green (nucleic acid stain) is used to detect DNA, including NETs and pre-NETs, and anti-hIgG is used to detect NET- and pre-NET-bound hMQ22.101f/LC4. Scale bars: 25 µm.

Figure 10A:
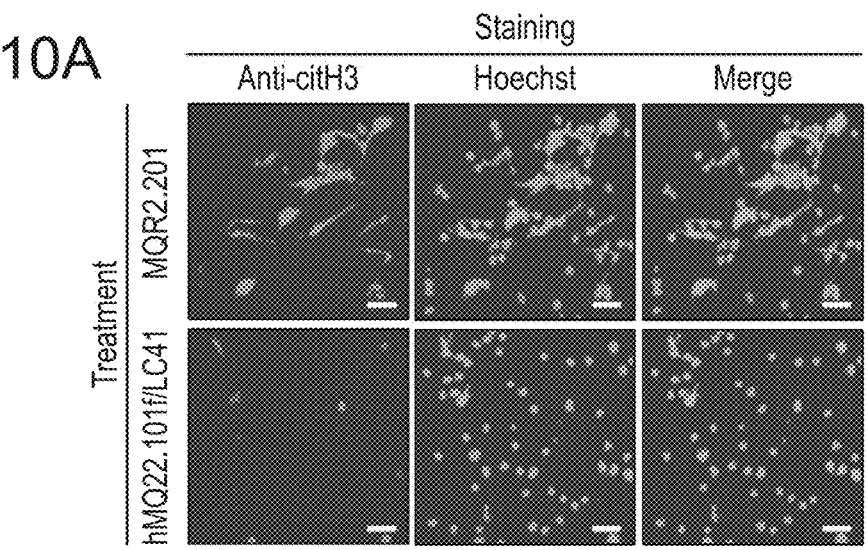
Figure 10B:
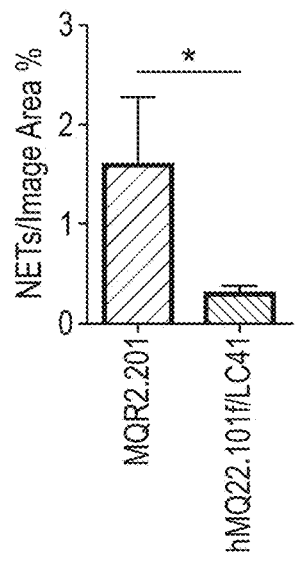
Figure 10C:
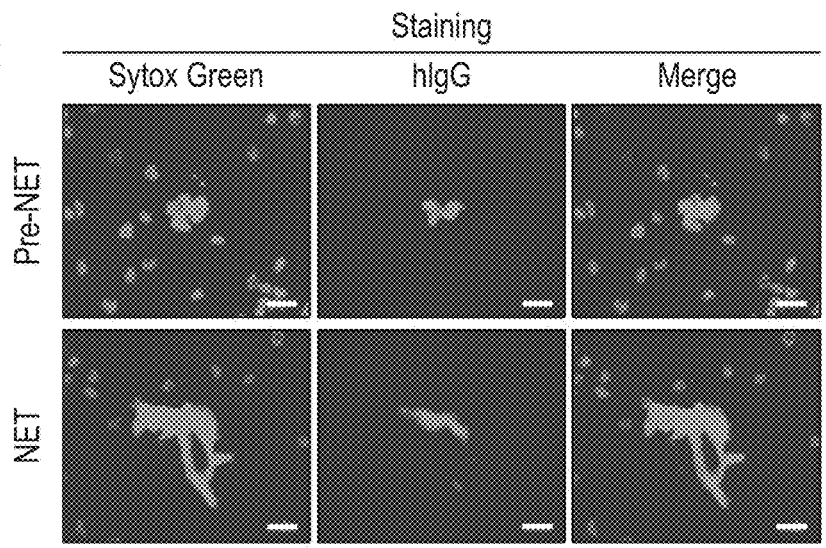

FIGS. 10A-10C: in vivo NET inhibition and binding of NETs by hMQ22.101f/LC41

A pristane-induced peritoneal cell influx mouse model was used in order to induce NET formation in vivo. 50 mg/kg MQR2.201 or hMQ22.101f/LC41 was administered immediately after injection of 500 µl pristane oil, followed by a second injection of 50 mg/kg MQR2.201 or hMQ22.101f/LC41 12 hours later. After 24 hours, cells were harvested. Inhibition of in vivo NET release was observed when mice were treated with hMQ22.101f/LC41, but not with MQR2.201.

(FIG. 10A) Representative pictures. (FIG. 10B) NET quantification by Hoechst (DNA) and citrullinated Histone 3 (citH3) colocalized. (FIG. 10C) Binding of hMQ22.101f/LC41 to NETs as well as pre-NETs, which could be the first step towards NET clearance by macrophages. Sytox™ Green (nucleic acid stain) is used to detect DNA, including NETs and pre-NETs, and anti-hIgG is used to detect NET- and pre-NET-bound hMQ22.101f/LC4.

Scale bars: 50 µm (FIG. 10A) or 25 µm (FIG. 10C).

Figure 11:
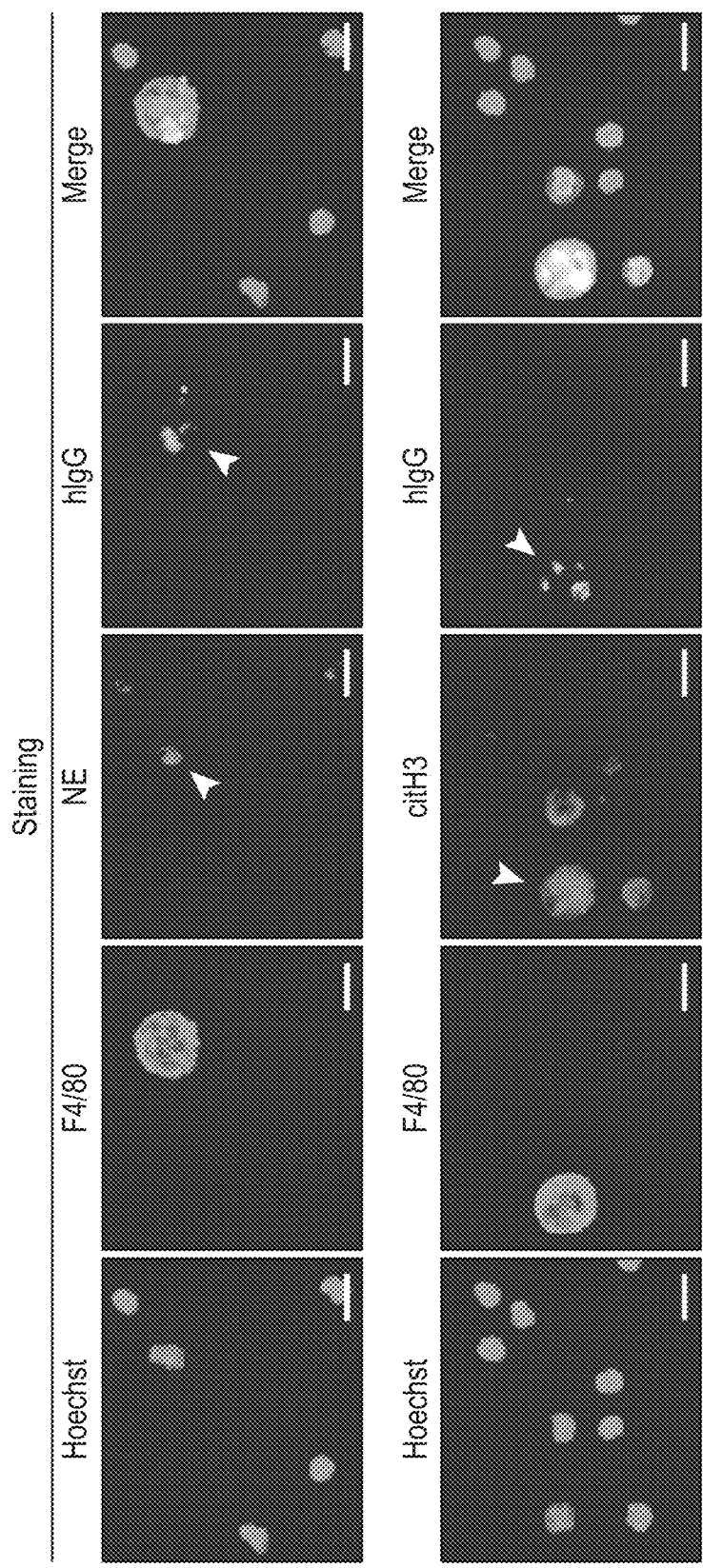

FIG. 11: hMQ22.101f/LC41-enriched NETs are phagocytosed by mouse macrophages in vivo A pristane-induced peritoneal cell influx mouse model was used in order to induce NET formation in vivo. 50 mg/kg MQR2.201 or hMQ22.101f/LC41 was administered immediately after injection of 500 µl pristane oil, followed by a second injection of 50 mg/kg MQR2.201 or hMQ22.101f/LC41 12 hours later. After 24 hours, cells were harvested and stained with Hoechst (DNA: blue), the macrophage marker anti-F4/80 (magenta), anti-NE (green), anti-citH3 (yellow), and anti-hIgG (cyan). NET particles containing NE (blue arrow), citH3 (red arrow) and hMQ22.101f/LC41 (white arrow) are present in macrophages (F4/80). Scale bars: 10 µm.

FIGS. 12A-12M: hMQ22.101j/e prevents NET-mediated tissue damage and disease progression in chronic CIA mice.

Figure 12A:
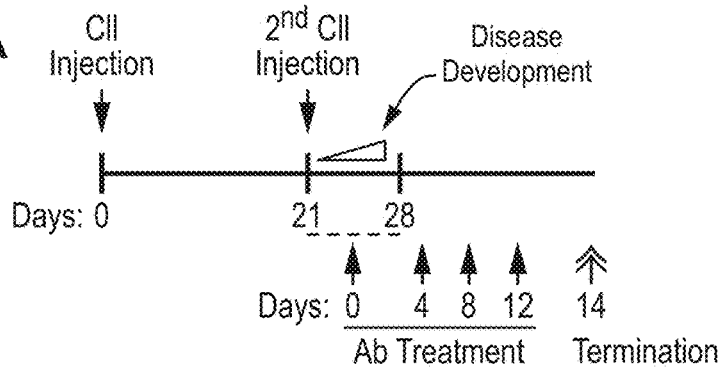

(FIG. 12A) A schematic overview of the CIA mouse model of RA. To induce chronic arthritis, mice were injected twice (day 0 and 21) with CII. Therapeutic treatment started after onset of the disease (between day 21-28) when the MAS were ≥0.75 and. Treatment includes four injections (4 day interval) with tapered dosing regimens of MQR2.201 (50/50/50/50 mg/kg) or hMQ22.101j/e (30/30/30/10, 50/50/50/15 or 50/10/10/10 mg/kg). Mice were terminated 14 days after the start of treatment. (FIG. 12B) The mean arthritis score (MAS) of CIA mice was evaluated for 14 days (n=10 mice per group; MQR2.201 was used to calculate statistical differences). (FIG. 12C) Bone damage of right and left hind knees and ankles were analyzed with X-ray at day 14 after the first antibody injection (n=10). Histological analysis, using H&E and SO staining, of joints from right and left ankles determined inflammatory cell influx (FIG. 12D), bone erosion (FIG. 12E), cartilage erosion (FIG. 12F), cartilage PG depletion (FIG. 12G), and chondrocyte death (FIG. 12H) at day 14 after the first antibody injection (n=16-20 mice ankles). (FIG. 12I) Representative immunofluorescence and H&E images of NET release in joints of right hind paws demonstrating citrullinated histone 3 (citH3; red), DAPI (blue), the neutrophil marker Ly6G (green), and myeloperoxidase (MPO; yellow). DAPI was used as a nuclear and extracellular DNA stain. Scale bars: 100 µm. Quantification of Ly6G (FIG. 12J) and NETs (colocalization of citH3 and MPO) (FIG. 12K) in the tibiotarsal joint, the proximal intertarsal joint, the distal intertarsal joint, and the tarsometatarsal joint of the right hind paws of mice (n=10). (FIG. 12L) Significant correlation of macroscopic score (paw swelling) and NETs per joint. (FIG. 12M) Significant correlation of macroscopic score (paw swelling) and neutrophils (Ly6G) per joint. Results depicted as means±SEM. *P<0.05, P<0.01, *P<0.001, ****P<0.0001 using two-way ANOVA with Dunnett's multiple comparisons test (FIG. 12B), unpaired two-tailed Student's t test (FIG. 12C), two-tailed Mann-Whitney statistical test (FIG. 12D to FIG. 12H, FIG. 12J, and FIG. 12K), or Spearman r test (FIG. 12L and FIG. 12M).

Figure 13:
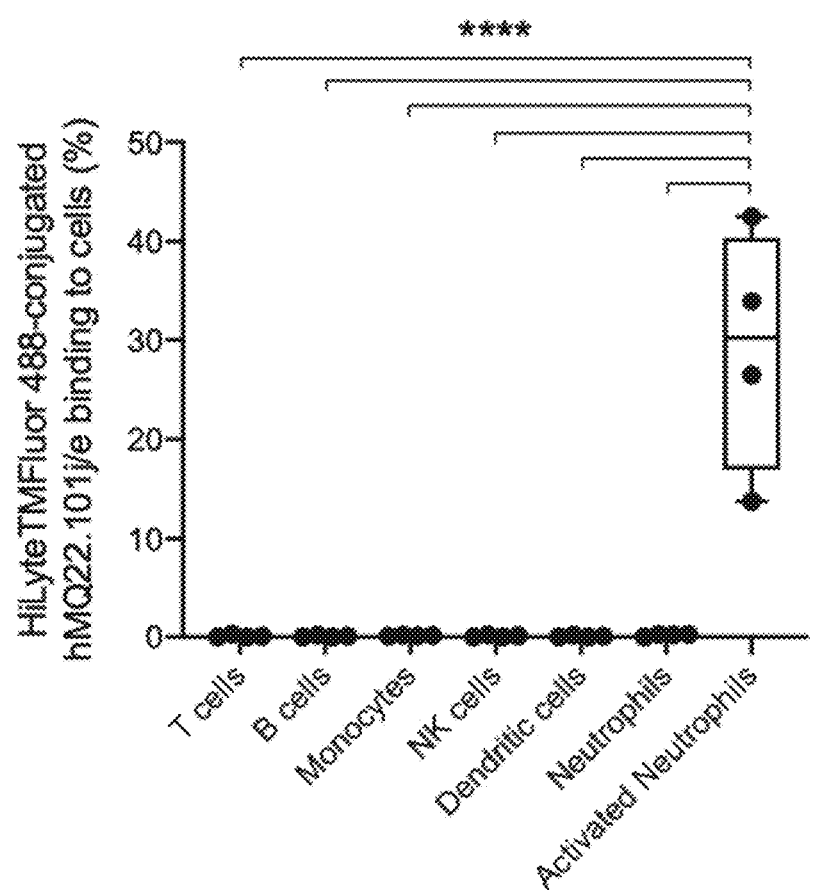

FIG. 13: hMQ22.101j/e does not bind to healthy leukocytes

PBMCs and neutrophils were isolated from blood of healthy volunteers. CD45 was used to distinguish leukocytes from erythrocytes and platelets and CD3, CD11c, CD14, CD20, CD56 and CD66b were used to mark T cells, DCs, monocytes, B cells, NK cells, and neutrophils, respectively. No binding of HiLyte™ Fluor 488 (dye)-conjugated hMQ22.101j/e was determined to healthy quiescent T cells, B cells, monocytes, NK cells, DCs and neutrophils. Activated neutrophil (5 µM A23187 for 45 min) were used as a positive control and show increased HiLyte™ Fluor 488 (dye)-conjugated hMQ22.101j/e binding. ****P<0.001 using ordinary one-way ANOVA with Dunnett's multiple comparisons test.

DETAILED DESCRIPTION OF THE INVENTION

It is to be understood that different applications of the disclosed invention may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural references unless the content clearly dictates otherwise. Thus, for example, reference to "an antibody" includes "antibodies", and the like.

All publications, patents and patent applications cited herein, whether supra or infra, are hereby incorporated by reference in their entirety.

The present invention relates to antibodies or binding fragments thereof that specifically bind to a citrullinated epitope on deiminated human histone 2A and/or histone 4. Deimination of human histone 2A and 4 can be carried out by enzymes such as peptidylarginine deiminase (PAD), for example PAD2 and PAD4. The antibodies of the invention may also specifically bind to a citrullinated epitope on human histone 3. The antibodies of the invention may specifically bind to a citrullinated epitope on human histone 2A and/or histone 4 and/or histone 3. The invention also relates to uses for such antibodies or binding fragment thereof, such as therapeutic uses.

The present invention relates to antibodies or binding fragments thereof that specifically bind to a citrullinated epitope on deiminated human histone 2A and/or histone 4 for use in the treatment or prevention of NET-associated pathologies. The antibodies or binding fragments thereof of the invention can be used in the treatment or prevention of NET-associated pathologies such as SLE, lupus, sepsis, vasculitis, inflammatory arthritis, rheumatoid arthritis and osteoarthritis, psoriasis, Alzheimer's disease, autoimmune hepatitis, juvenile idiopathic arthritis, Sjögren's disease, Anti-phospholipid Syndrome, Bechet's disease, spondylitis, spondyloarthropathy, multiple system atrophy, Parkinson's disease, Lewy body dementia asthma, allergic rhinovirus exacerbated asthma, allergic asthma, cystic fibrosis, fibrosis and idiopathic pulmonary fibrosis, dry eye disease, uveitis, nongranulomatous uveitis, granulomatous uveitis, dermatitis, atopic dermatitis, COPD, bronchitis, or other NET-associated pathologies such as wound healing in diabetes, cancer, cancer metastasis, and transplant organ health in vivo or ex vivo.

Targets of Antibody or Binding Fragments Thereof of the Invention

Citrulline is an amino acid that is not incorporated into proteins during normal translation, however, it may be generated by post-translational modification of an arginine residue by enzymes such as PAD; (EC 3.5.3.15). In mammals (humans, mice and rats), five PAD isotypes (PAD1-PAD6; 'PAD4' and 'PAD5' are used for the same isotype), each encoded by a distinct gene, have been identified thus far.

Citrullination of histone 2A and/or histone 4 is associated with the formation of NETs. The downstream pathological effects of NET formation can be numerous. For example, there can be autoantigen exposure to the extracellular space and the subsequent production of pathological autoantibodies by the subject. NET-derived histones can be toxic to the vascular wall and organs leading to vascular damage and organ failure. NETs can lead to the formation of autoantigen/autoantibody immune complexes, which enhance further inflammation, in for example the kidney of SLE patients. NETs are also involved in metastasis in cancer progression.

The antibodies or binding fragments thereof according to the invention specifically bind to a citrullinated epitope on deiminated human histone 2A and/or histone 4. The antibodies of the invention may also specifically bind to a citrullinated epitope on deiminated human histone H$_3$. In a specific embodiment, the antibodies or binding fragments thereof according to the invention specifically bind to a citrullinated epitope on deiminated human histone 2A and/or histone 4, wherein the epitope comprises a peptide selected from the group consisting of SEQ ID NOs: 18, 19, 20, 21 and 22. The antibodies or binding fragments thereof may also bind to epitopes comprising the peptides of SEQ ID NO: 53 or 54.

Antibodies or Binding Fragments Thereof

The term "antibodies", "antibody" or "binding fragment thereof" as used herein refers to a structure, preferably a protein or polypeptide structure, capable of specific binding to a target molecule often referred to as "antigen".

The antibody molecule as employed herein refers to an antibody or binding fragment thereof. The term 'antibody' as used herein generally relates to intact (whole) antibodies i.e. comprising the elements of two heavy chains and two light chains. The antibody may comprise further additional binding domains for example as per the molecule DVD-Ig as disclosed in WO 2007/024715, or the so-called (FabFv)$_2$Fc described in WO2011/030107. Thus 'antibody' as employed herein includes mono-, bi-, tri- or tetra-valent full-length antibodies.

Binding fragments of antibodies include single chain antibodies (i.e. a full-length heavy chain and light chain); Fab, modified Fab, Fab', modified Fab', F(ab')2, Fv, Fab-Fv, Fab-dsFv, single domain antibodies (e.g. VH or VL or VHH), scFv, mono-, bi-, tri- or tetra-valent antibodies, Bis-scFv, diabodies, tribodies, triabodies, tetrabodies and epitope-binding fragments of any of the above (see for example Holliger P and Hudson P J, 2005, Nat. Biotechnol., 23: 1126-1136; Adair J R and Lawson A D G, 2005, Drug Design Reviews—Online, 2, 209-217). The methods for creating and manufacturing these antibody fragments are well known in the art (see for example Verma R et al., 1998, J. Immunol. Methods, 216, 165-181). The Fab-Fv format was first disclosed in WO2009/040562 and the disulfide-stabilized versions thereof, the Fab-dsFv was first disclosed in WO2010/035012. Other antibody fragments for use in the present invention include Fab and Fab' fragments. Multivalent antibodies may comprise multiple specificities e.g. bispecific or may be monospecific.

An antibody or binding fragment thereof may be selected from the group consisting of single chain antibodies, single chain variable fragments (scFvs), variable fragments (Fvs), fragment antigen-binding regions (Fabs), recombinant antibodies, monoclonal antibodies, fusion proteins comprising the antigen-binding domain of a native antibody or an aptamer, single-domain antibodies (sdAbs), also known as VHH antibodies, nanobodies (Camelid-derived single-domain antibodies), shark IgNAR-derived single-domain antibody fragments called VNAR, diabodies, triabodies, Anticalins, aptamers (DNA or RNA) and active components or fragments thereof.

IgG1 (e.g. IgG1/kappa) antibodies having an IgG1 heavy chain and a light chain may advantageously be used in the invention. However, other human antibody isotypes are also encompassed by the invention, including IgG2, IgG3, IgG4, IgM, IgA1, IgA2, IgAsec, IgD and IgE in combination with a kappa or lambda light chain. Also, all animal-derived antibodies of various isotypes can be used in the invention. The antibodies can be full-size antibodies or antigen-binding fragments of antibodies, including Fab, F(ab')2, single-chain Fv fragments, or single-domain VHH, VH or VL single domains.

The term: "specifically binds to citrulline" or "specifically binds to a citrullinated epitope" in this context means that the antibody or binding fragment thereof binds to a structure such as a peptide containing a citrulline residue whereas the antibody or binding fragment thereof binds less strongly or preferably not at all with the same structure containing an arginine residue instead of the citrulline residue. The term peptide should be interpreted as a structure that is capable of presenting the citrulline residue in the correct context for immunoreactivity with the antibodies or binding fragments thereof as described herein, preferably in the same context as it appears in the human or animal body, preferably in the context of a native polypeptide.

The antibodies or binding fragments thereof of the invention specifically bind to a citrullinated epitope on deiminated human histone 2A and/or histone 4. The binding of antibodies or binding fragments thereof to a citrullinated epitope on deiminated human histone 2A and/or histone 4 blocks NET formation. Citrullination of histones is associated with the formation of NETs.

Blocking of NET formation can be total or partial. For example, the antibody or binding fragment thereof of the invention may reduce NET formation from 10 to 50%, at least 50% or at least 70%, 80%, 90%, 95% or 99%. NET blocking can be measured by any suitable means, for example by measuring NETosis in vitro (Kraaij T et al., 2016, Autoimmun. Rev. 15, 577-584).

The terms "binding activity" and "binding affinity" are intended to refer to the tendency of an antibody molecule to bind or not to bind to a target. Binding affinity may be quantified by determining the dissociation constant (Kd) for an antibody and its target. Similarly, the specificity of binding of an antibody to its target may be defined in terms of the comparative dissociation constants (Kd) of the antibody for its target as compared to the dissociation constant with respect to the antibody and another, non-target molecule.

Typically, the Kd for the antibody with respect to the target will be 2-fold, preferably 5-fold, more preferably 10-fold less than the Kd with respect to the other, non-target molecule such as unrelated material or accompanying material in the environment. More preferably, the Kd will be 50-fold less, even more preferably 100-fold less, and yet more preferably 200-fold less.

The value of this dissociation constant can be determined directly by well-known methods, and can be computed even for complex mixtures by methods such as those, for example, set forth in Caceci M S and Cacheris W P (1984, Byte, 9, 340-362). For example, the Kd may be established using a double-filter nitrocellulose filter binding assay such as that disclosed by Wong I and Lohman T M (1993, Proc. Natl. Acad. Sci. USA, 90, 5428-5432) or for example, by using Octet® surface plasmon resonance.

One method for the evaluation of binding affinity for deiminated human histone 2A and/or histone 4 is by ELISA. Other standard assays to evaluate the binding ability of ligands such as antibodies towards targets are known in the art, including for example, Western blots, RIAs, and flow cytometry analysis. The binding kinetics (e.g. binding affinity) of the antibody also can be assessed by standard assays known in the art, such as surface plasmon resonance, for example by Biacore™ system analysis.

Preferably the antibody of the invention has a binding affinity for deiminated human histone 2A and/or histone 4 of 1 nM or less. Preferably the antibody of the invention has a binding affinity for deiminated human histone 2A and/or histone 4, and/or deiminated human histone $H_3$ of 0.5 nM or less, 0.1 nM or less, 50 pM or less, 10 pM or less, 5 pM or less, 2 pM or less or 1 pM or less.

The antibody or binding fragment thereof may also be a fusion protein comprising the antigen-binding domain of a native antibody or an aptamer, such as an aptamer in the form of DNA or RNA.

Preferably the antibody or binding fragment thereof of the invention is a monoclonal antibody. Monoclonal antibodies are immunoglobulin molecules that are identical to each other and have a single binding specificity and affinity for a particular epitope. Monoclonal antibodies (mAbs) of the present invention can be produced by a variety of techniques, including conventional monoclonal antibody methodology, for example those disclosed in "Monoclonal Antibodies: a manual of techniques" (Zola H, 1987, CRC Press) and in "Monoclonal Hybridoma Antibodies: techniques and applications" (Hurrell J G R, 1982 CRC Press).

The antibody or binding fragment thereof of the invention comprises a binding domain. A binding domain will generally comprise 6 CDRs (3 in case of VHH), three from a heavy chain and three from a light chain. In one embodiment the CDRs are in a framework and together form a variable region or domain. Thus in one embodiment an antibody or binding fragment comprises a binding domain specific for the antigen comprising a light chain variable region or domain and a heavy chain variable region or domain.

The residues in antibody variable domains are conventionally numbered according to IMGT (http://www.imgt.org). This system is set forth in Lefranc M P (1997, J, Immunol. Today, 18, 509). This numbering system is used in the present specification except where otherwise indicated.

The IMGT residue designations do not always correspond directly with the linear numbering of the amino acid residues. The actual linear amino acid sequence may contain fewer or additional amino acids than in the strict IMGT numbering corresponding to a shortening of, or insertion into, a structural component, whether framework or CDR, of the basic variable domain structure. The correct IMGT numbering of residues may be determined for a given antibody by alignment of residues of homology in the sequence of the antibody with a "standard" IMGT numbered sequence.

The CDRs of the heavy chain variable domain are located at residues 27-38 (CDR1 of VH), residues 56-65 (CDR2 of VH) and residues 105-117 (CDR3 of VH) according to the IMGT numbering system.

The CDRs of the light chain variable domain are located at residues 27-38 (CDR1 of VL), residues 56-65 (CDR2 of VL) and residues 105-117 (CDR3 of VL) according to the IMGT numbering system.

The antibodies or binding fragments thereof of the present invention are disclosed herein by the primary amino acid sequence of their CDR regions. The antibodies or binding fragments thereof of the present invention are disclosed herein by the primary amino acid sequence of their heavy and light chains.

The present invention is based on the discovery that a modified CDR1 of the VL of an antibody or binding fragment thereof that specifically binds to a citrullinated epitope on deiminated human histone 2A and/or histone 4 provides improved properties to the antibody or binding fragment thereof over an antibody or binding fragment thereof comprising an unmodified version of CDR1 of the VL. The unmodified CDR1 of the VL of the antibody used to derive the invention comprises or consists of the amino acid sequences QSLLDSDGKTY (SEQ ID NO: 36) or QSLVDSDGKTY (SEQ ID NO: 37).

The modified CDR1 of the VL chain of the antibody or binding fragment thereof of the invention comprises or consists of the amino acid sequence QSL-$X_1$-D-$X_2$-D-$X_3$-KTY, wherein $X_1$ is V or L, $X_2$ is T, S, A or N and $X_3$ is G or A (SEQ ID NO:57), provided that the amino acid sequence is not QSLLDSDGKTY (SEQ ID NO: 36) or QSLVDSDGKTY (SEQ ID NO: 37). The modified CDR1 of the VL chain of the antibody or binding fragment thereof of the invention shows reduced isomerization, in comparison with the unmodified CDR1 of SEQ ID NO: 36 or 37, but maintains the binding properties of the unmodified CDR1.

The amino acid sequences of the CDRs for the VH of a particular antibody or binding fragment thereof of the invention are shown in SEQ ID NOs: 1, 2 and 3. The CDRs 2 and 3 for the VL are shown in SEQ ID NOs: 4 and 5.

The amino acid sequences of the VH and VL of a particular antibody or binding fragment thereof of the invention are given in SEQ ID NOs: 11 and 13. The CDRs for the VH are shown in SEQ ID NOs: 1, 2 and 3. The CDRs for the VL are shown in SEQ ID NOs: 6, 4 and 5.

The amino acid sequences of the VH and VL of another antibody or binding fragment thereof of the invention are given in SEQ ID NOs: 11 and 14. The CDRs for the VH are shown in SEQ ID NOs: 1, 2 and 3. The CDRs for the VL are shown in SEQ ID NOs: 7, 4 and 5.

The amino acid sequences of the VH and VL of another antibody or binding fragment thereof of the invention are given in SEQ ID NOs: 11 and 15. The CDRs for the VH are shown in SEQ ID NOs: 1, 2 and 3. The CDRs for the VL are shown in SEQ ID NOs: 8, 4 and 5.

The amino acid sequences of the VH and VL of another antibody or binding fragment thereof of the invention are given in SEQ ID NOs: 11 and 16. The CDRs for the VH are shown in SEQ ID NOs: 1, 2 and 3. The CDRs for the VL are shown in SEQ ID NOs: 9, 4 and 5.

The amino acid sequences of the VH and VL of another antibody or binding fragment thereof of the invention are given in SEQ ID NOs: 11 and 17. The CDRs for the VH are shown in SEQ ID NOs: 1, 2 and 3. The CDRs for the VL are shown in SEQ ID NOs: 10, 4 and 5.

The amino acid sequences of the VH and VL of another antibody or binding fragment thereof of the invention are given in SEQ ID NOs: 12 and 13. The CDRs for the VH are shown in SEQ ID NOs: 1, 2 and 3. The CDRs for the VL are shown in SEQ ID NOs: 6, 4 and 5.

The amino acid sequences of the VH and VL of another antibody or binding fragment thereof of the invention are given in SEQ ID NOs: 12 and 14. The CDRs for the VH are shown in SEQ ID NOs: 1, 2 and 3. The CDRs for the VL are shown in SEQ ID NOs: 7, 4 and 5.

The amino acid sequences of the VH and VL of another antibody or binding fragment thereof of the invention are given in SEQ ID NOs: 12 and 15. The CDRs for the VH are shown in SEQ ID NOs: 1, 2 and 3. The CDRs for the VL chain are shown in SEQ ID NOs: 8, 4 and 5.

The amino acid sequences of the VH and VL of another antibody or binding fragment thereof of the invention are given in SEQ ID NOs: 12 and 16. The CDRs for the VH are shown in SEQ ID NOs: 1, 2 and 3. The CDRs for the VL are shown in SEQ ID NOs: 9, 4 and 5.

The amino acid sequences of the VH and VL of another antibody or binding fragment thereof of the invention are given in SEQ ID NOs: 12 and 17. The CDRs for the VH are shown in SEQ ID NOs: 1, 2 and 3. The CDRs for the VL are shown in SEQ ID NOs: 10, 4 and 5.

In an embodiment of the present invention, the antibody of the invention comprises the heavy chain variable domain amino acid sequence of SEQ ID NO: 11, the light chain variable domain amino acid sequence of SEQ ID NO: 16, a heavy chain constant region amino acid sequence comprising SEQ ID NO: 23 or 56, and the light chain constant region amino acid sequence of SEQ ID NO: 24.

In an embodiment of the present invention, the antibody of the invention comprises the heavy chain variable domain amino acid sequence of SEQ ID NO: 11, the light chain variable domain amino acid sequence of SEQ ID NO: 16, the heavy chain constant region amino acid sequence of SEQ ID NO: 23 or 56, and the light chain constant region amino acid sequence of SEQ ID NO: 24.

An antibody or binding fragment thereof of the invention may comprise one or more of the CDR sequences of any one of the specific antibodies as described above, except that the CDR1 of the VL is always present as either comprising or consisting of the amino acid sequence QSL-$X_1$-D-$X_2$-D-$X_3$-KTY, wherein $X_1$ is V or L, $X_2$ is T, S, A or N and $X_3$ is G or A (SEQ ID NO:57), provided that the amino acid sequence is not QSLLDSDGKTY (SEQ ID NO: 36) or QSLVDSDGKTY (SEQ ID NO: 37), or either comprises or consists of SEQ ID NOs: 6, 7, 8, 9 or 10.

An antibody or binding fragment thereof of the invention may comprise one or more VH CDR sequences and alternatively or additionally one or more VL CDR sequences of said specific antibody, in addition to VL CDR1. An antibody or binding fragment thereof of the invention may comprise one, two or all three of the VH CDR sequences of a specific antibody or binding fragment thereof as described above and alternatively or additionally one, two or all three of the VL chain CDR sequences of said specific antibody or binding fragment thereof, including VL CDR1. An antibody or binding fragment thereof of the invention may comprises all six CDR sequences of a specific antibody or binding fragment as described above. By way of example, an antibody of the invention may comprise one of SEQ ID NO: 6, 7, 8, 9 or 10 and one or more of SEQ ID NOs: 1, 2, 3, 4 and 5.

In an embodiment of the invention, the modified CDR1 of the VL chain of the antibody or binding fragment thereof of the invention comprises or consists of the amino acid sequence QSL-$Z_1$-$Z_2$-$Z_3$-$Z_4$-$Z_5$-KTY, wherein $Z_1$ is V or L, $Z_2$ is D or E, $Z_3$ is T, S, A or N, $Z_4$ is D, E, S or A and $Z_5$ is G or A (SEQ ID NO:58), provided that the amino acid sequence is not QSLLDSDGKTY (SEQ ID NO: 36) or QSLVDSDGKTY (SEQ ID NO: 37). The modified CDR1 of the VL chain of the antibody or binding fragment thereof of the invention shows reduced isomerization, in comparison with the unmodified CDR1 of SEQ ID NO: 36 or 37, but maintains the binding properties of the unmodified CDR1. The modified CDR1 of the VL chain of the antibody or binding fragment thereof of the invention may comprise or consist of SEQ ID NO: 6, 7, 8, 9, 10, 41, 42, 43, 44, 45, 46, 47, 48, 49, 50, 51 or 52. In an embodiment of the invention, the antibody of the invention may comprise one of SEQ ID NO: 6, 7, 8, 9, 10, 41, 42, 43, 44, 45, 46, 47, 48, 49, 50, 51 or 52, and one or more of SEQ ID NOs: 1, 2, 3, 4 and 5. In an embodiment of the invention, the antibody of the invention comprises one of SEQ ID NO: 6, 7, 8, 9, 10, 41, 42, 43, 44, 45, 46, 47, 48, 49, 50, 51 or 52, and all of SEQ ID NOs: 1, 2, 3, 4 and 5.

An antibody or binding fragment thereof of the invention may alternatively comprise a variant of one of these heavy chain variable domains or CDR sequences in CDR2 or 3 of the VL. For example, a variant may be a substitution, deletion or addition variant of any of the above amino acid sequences.

A variant antibody may comprise 1, 2, 3, 4, 5, up to 10, up to 20, up to 30 or more amino acid substitutions and/or deletions from the specific sequences and fragments discussed above, whilst maintaining the activity of the antibodies described herein. "Deletion" variants may comprise the deletion of, for example, 1, 2, 3, 4 or 5 individual amino acids or of one or more small groups of amino acids such as 2, 3, 4 or 5 amino acids. "Small groups of amino acids" can be defined as being sequential, or in close proximity but not sequential, to each other. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid, another aliphatic amino acid, another tiny amino acid, another small amino acid or another large amino acid. Some properties of the 20 main amino acids, which can be used to select suitable substituents, are as follows:

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

Preferred "derivatives" or "variants" include those in which instead of the naturally occurring amino acid the amino acid, which appears in the sequence, is a structural analog thereof. Amino acids used in the sequences may also be derivatized or modified, e.g. labelled, providing the function of the antibody is not significantly adversely affected.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Preferably variant antibodies according to the invention have an amino acid sequence which has more than 60%, or more than 70%, e.g. 75 or 80%, preferably more than 85%, e.g. more than 90%, 95%, 96%, 97%, 98% or 99% amino acid identity to the VL and/or VH, or a fragment thereof, of an antibody disclosed herein. This level of amino acid identity may be seen across the full-length of the relevant SEQ ID NO sequence or over a part of the sequence, such as across 20, 30, 50, 75, 100, 150, 200 or more amino acids, depending on the size of the full-length polypeptide.

Preferably the variant antibodies comprise one or more of the CDR sequences as described herein.

In connection with amino acid sequences, "sequence identity" refers to sequences, which have the stated value when assessed using ClustalW (Thompson J D et al., 1994, Nucleic Acid Res., 22, 4673-4680) with the following parameters:

Pairwise alignment parameters—Method: slow/accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: G, P, S, N, D, Q, E, K, R. Sequence identity at a particular residue is intended to include identical residues, which have simply been derivatized.

The present invention thus provides antibodies having specific VH and VL amino acid sequences and variants and fragments thereof, which maintain the function or activity of these VHs and VLs.

Accordingly, the present invention encompasses antibodies or binding fragments thereof comprising variants of the VH that retain the ability of specifically binding a citrullinated epitope on human deiminated human histone 2A and/or histone 4. A variant of the heavy chain may have at least 70%, at least 80%, at least 85%, at least 90%, at least 95%, at least 96%, at least 97%, at least 98% or at least 99% amino acid sequence identity to the unmodified VH. The variant of the VH may comprise a fragment of at least 7 amino acids of hVH22.101f or hVH22.101HC9 (SEQ ID NO: 11 and 12, respectively), wherein the antibody or binding fragment thereof retains the ability of being specifically reactive with a citrullinated epitope on deiminated human histone 2A and/or histone 4; or a variant of hVH22.101f or hVH22.101HC9 (SEQ ID NO: 11 and 12, respectively) having at least 70% amino acid sequence identity to a sequence of hVH22.101f or hVH22.101HC9 (SEQ ID NO: 11 and 12, respectively), wherein the antibody or binding fragment thereof retains the ability of being specifically reactive with a citrullinated epitope on deiminated human histone 2A and/or histone 4.

Polynucleotides, Vectors and Host Cells

The present invention also encompasses polynucleotides, vectors and expression vectors encoding the antibody or binding fragments thereof described herein.

The invention also relates to polynucleotides that encode antibodies of the invention. Thus, a polynucleotide of the invention may encode any antibody or fragment as described herein. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, genomic DNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule, which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence. In one embodiment, a polynucleotide of the invention comprises a sequence, which encodes a VH or VL amino acid sequence as described above. The polynucleotide may encode the VH or VL sequence of a specific antibody or binding fragment thereof as disclosed herein.

An antibody or binding fragment thereof of the invention may thus be produced from or delivered in the form of a polynucleotide, which encodes, and is capable of expressing it. Where the antibody comprises two or more chains, a polynucleotide of the invention may encode one or more antibody chains. For example, a polynucleotide of the invention may encode an antibody light chain, an antibody heavy chain or both. Two polynucleotides may be provided, one of which encodes an antibody light chain and the other of which encodes the corresponding antibody heavy chain. Such a polynucleotide or pair of polynucleotides may be expressed together such that an antibody of the invention is generated.

Polynucleotides of the invention can be synthesized according to methods well known in the art, as described by way of example in Sambrook J et al. (1989, Molecular cloning: a laboratory manual; Cold Spring Harbor: New York: Cold Spring Harbor Laboratory Press).

The nucleic acid molecules of the present invention may be provided in the form of an expression cassette, which includes control sequences operably linked to the inserted sequence, thus allowing for expression of the antibody of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector, which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals, which may be necessary, and which are positioned in the correct orientation, in order to allow for expression of a peptide of the invention. Other suitable vectors would be apparent to persons skilled in the art. By way of further example in this regard we refer to Sambrook J et al. (1989, Molecular cloning: a laboratory manual; Cold Spring Harbor: New York: Cold Spring Harbor Laboratory Press).

A person skilled in the art may use the sequences described herein to clone or generate cDNA or genomic sequences for instance such as described in the below examples. Cloning of these sequences in an appropriate eukaryotic expression vector, like pcDNA3 (Invitrogen), or derivates thereof, and subsequent transfection of mammalian cells (like CHO cells) with combinations of the appropriate light and heavy chain-containing vectors will result in the expression and secretion of the antibodies described herein.

The skilled person may also make analogues of the antibodies or binding fragments thereof as described herein by using the specific binding domains of the antibody sequences and express them in a different context, such as a polypeptide, such as a fusion protein. This is well known in the art.

The invention also includes cells that have been modified to express an antibody of the invention. Such cells include transient, or preferably stable higher eukaryotic cell lines, such as mammalian cells or insect cells, lower eukaryotic cells, such as yeast or prokaryotic cells, such as bacterial cells. Particular examples of cells, which may be modified by insertion of vectors or expression cassettes encoding for an antibody of the invention, include mammalian HEK293, CHO, HeLa, NS0 and COS cells. Preferably the cell line selected will be one which is not only stable, but also allows for mature glycosylation.

Such cell lines of the invention may be cultured using routine methods to produce an antibody or binding fragment thereof of the invention, or may be used therapeutically or prophylactically to deliver antibodies or binding fragments thereof of the invention to a subject. Alternatively, polynucleotides, expression cassettes or vectors of the invention may be administered to a cell from a subject ex vivo and the cell then returned to the body of the subject.

The present invention also encompasses a process for the production of an antibody or binding fragment thereof that specifically binds to a citrullinated epitope on deiminated human histone 2A and/or histone 4, comprising culturing a host cell as described herein and isolating the antibody or binding fragment thereof from said cell.

Pharmaceutical Compositions

The invention encompasses pharmaceutical compositions comprising the antibodies or binding fragments thereof of the invention. The invention encompasses pharmaceutical compositions comprising the antibodies or binding fragments thereof of the invention and a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral, e.g. intravenous, intraocular, intramuscular, subcutaneous, intradermal or intraperitoneal administration (e.g. by injection or infusion). In certain embodiments, a pharmaceutically acceptable carrier comprises at least one carrier selected from the group consisting of a co-solvent solution, liposomes, micelles, liquid crystals, nanocrystals, nanoparticles, emulsions, microparticles, microspheres, nanospheres, nanocapsules, polymers or polymeric carriers, surfactants, suspending agents, complexing agents such as cyclodextrins or adsorbing molecules such as albumin, surface active particles, and chelating agents. In further embodiments, a polysaccharide comprises hyaluronic acid and derivatives thereof, dextran and derivatives thereof, cellulose and derivatives thereof (e.g. methylcellulose, hydroxy-propylcellulose, hydroxy-propylmethylcellulose, carboxymethylcellulose, cellulose acetate phthalate, cellulose acetate succinate, cellulose acetate butyrate, hydroxypropylmethylcellulose phthalate), chitosan and derivative thereof, [beta]-glucan, arabinoxylans, carrageenans, pectin, glycogen, fucoidan, chondrotin, dermatan, heparan, heparin, pentosan, keratan, alginate, cyclodextrins, and salts and derivatives, including esters and sulfates, thereof.

Preferred pharmaceutically acceptable carriers comprise aqueous carriers or diluents. Examples of suitable aqueous carriers that may be employed in the pharmaceutical compositions of the invention include water, buffered water and saline.

Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols, such as mannitol, sorbitol, or sodium chloride in the composition.

A pharmaceutical composition of the invention also may include a pharmaceutically acceptable anti-oxidant. These compositions may also contain adjuvants, such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents, which delay absorption such as aluminium monostearate and gelatin.

Therapeutic compositions typically must be sterile and stable under the conditions of manufacture and storage. The pharmaceutical composition can be formulated as a solution, microemulsion, liposome, or other ordered structure suitable to high drug concentration.

Sterile injectable solutions can be prepared by incorporating the active agent (e.g. antibody) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

Pharmaceutical compositions of the invention may comprise additional active ingredients as well as an antibody of the invention. As mentioned above, compositions of the invention may comprise one or more antibodies of the invention. They may also comprise additional therapeutic or prophylactic active agents.

Depending on the route of administration, the antibody or binding fragment thereof may be coated in a material to protect the antibody from the action of acids and other natural conditions that may inactivate or denature the antibody.

In a preferred embodiment, the pharmaceutical composition according to the invention is in a form selected from the group consisting of an aqueous solution, a gel, a hydrogel, a film, a paste, a cream, a spray, an ointment, or a wrap.

In further embodiments, the pharmaceutical compositions described herein can be administered by a route such as intravenous, subcutaneous, intraocular, intramuscular, intraarticular, intradermal, intraperitoneal, spinal or by other parenteral routes of administration, for example by injection or infusion. Administration may be rectal, oral, ocular, topical, epidermal or by the mucosal route. Administration may be local, including peritumoral, juxtatumoral, intratumoral, to the resection margin of tumors, intralesional, perilesional, by intra cavity infusion, intravesicle administration, or by inhalation. In a preferred embodiment, the pharmaceutical composition is administered intravenously or subcutaneously.

Also within the scope of the present invention are kits comprising antibodies or other compositions of the invention and instructions for use. The kit may further contain one or more additional reagents, such as an additional therapeutic or prophylactic agent as discussed herein.

Therapeutic Uses of the Antibodies and Binding Fragments Thereof of the Invention The antibodies or binding fragments thereof in accordance with the present invention maybe used in therapy. In therapeutic applications, antibodies or compositions are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". Effective amounts for a given purpose will depend on the severity of the disease or injury as well as the weight and general state of the subject. As used herein, the term "subject" includes any human.

In particular embodiments, the antibody or binding fragment thereof of the invention may be linked (directly or indirectly) to another moiety. The other moiety may be a therapeutic agent such as a drug. The other moiety may be a detectable label. The other moiety may be a binding moiety, such as an antibody or a polypeptide binding domain specific for a therapeutic target. The antibody or binding fragment thereof of the invention may be a bispecific antibody.

The therapeutic agent or a detectable label may be directly attached, for example by chemical conjugation, to an antibody or binding fragment thereof of the invention. Methods of conjugating agents or labels to an antibody are known in the art. For example, carbodiimide conjugation (Bauminger S and Wilchek M, 1980, Methods Enzymol., 70, 151-159) may be used to conjugate a variety of agents, including doxorubicin, to antibodies or peptides. The water-soluble carbodiimide, 1-ethyl-3-(3-dimethylaminopropyl) carbodiimide (EDC) is particularly useful for conjugating a functional moiety to a binding moiety.

Other methods for conjugating a moiety to antibodies can also be used. For example, sodium periodate oxidation followed by reductive alkylation of appropriate reactants can be used, as can glutaraldehyde cross-linking. However, it is recognized that, regardless of which method of producing a conjugate of the invention is selected, a determination must be made that the antibody maintains its targeting ability and that the functional moiety maintains its relevant function.

The therapeutic agent linked to the antibody may comprise a polypeptide or a polynucleotide encoding a polypeptide which is of therapeutic benefit. Examples of such polypeptides include anti-proliferative or anti-inflammatory cytokines.

The antibody may be linked to a detectable label. By "detectable label" it is meant that the antibody is linked to a moiety which, when located at the target site following administration of the antibody into a patient, may be detected, typically non-invasively from outside the body and the site of the target located. Thus, the antibody may be useful in imaging and diagnosis.

Typically, the label is or comprises a radioactive atom which is useful in imaging. Suitable radioactive atoms include 99mTc and 123I for scintigraphic studies. Other labels include, for example, spin labels for magnetic resonance imaging (MRI) such as 123I again, 131I, 111In, 19F, 13C, 15N, 17O, gadolinium, manganese or iron. Clearly, the sufficient amount of the appropriate atomic isotopes must be linked to the antibody in order for the molecule to be readily detectable.

The radio- or other labels may be incorporated in known ways. For example, the antibody, or fragment thereof, may be biosynthesized or may be synthesized by chemical amino acid synthesis using suitable amino acid precursors involving, for example, fluorine-19 in place of hydrogen. Labels such as 99mTc, 123I, 186Rh, 188Rh and 111In can, for example, be attached via cysteine residues in polypeptides. Yttrium-90 can be attached via a lysine residue. Preferably, the detectable label comprises a radioactive atom, such as, for example technetium-99m or iodine-123. Alternatively, the detectable label may be selected from the group comprising: iodine-123; iodine-131; indium-111; fluorine-19; carbon-13; nitrogen-15; oxygen-17; gadolinium; manganese; iron.

In one embodiment, an antibody of the invention is able to bind selectively to a directly or indirectly cytotoxic moiety or to a detectable label. Thus, in this embodiment, the antibody is linked to a moiety which selectively binds to a further compound or component which is cytotoxic or readily detectable.

An antibody or binding fragment of the present invention, or a composition comprising said antibody or fragment, may be administered via one or more routes of administration using one or more of a variety of methods known in the art. As will be appreciated by the skilled artisan, the route and/or mode of administration will vary depending upon the desired results. Preferred routes of administration for antibodies or compositions of the invention include intravenous, subcutaneous, intraocular, intramuscular, intradermal, intraperitoneal, spinal or other parenteral routes of administration, for example by injection or infusion. The phrase "parenteral administration" as used herein means modes of administration other than enteral and topical administration, usually by injection. Administration may be rectal, oral, ocular, topical, epidermal or by the mucosal route. Administration may be local, including peritumoral, juxtatumoral, intratumoral, to the resection margin of tumors, intralesional, perilesional, by intra cavity infusion, intravesicle administration, or by inhalation. In a preferred embodiment, the pharmaceutical composition is administered intravenously or subcutaneously.

A suitable dosage of an antibody or binding fragment thereof of the invention may be determined by a skilled medical practitioner. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular antibody employed, the route of administration, the time of administration, the rate of excretion of the antibody, the duration of the treatment, other drugs, compounds and/or materials used in combination with the particular compositions employed, the age, sex, weight, condition, general health and prior medical history of the patient being treated, and like factors well known in the medical arts.

A suitable dose of an antibody or binding fragment thereof of the invention may be, for example, in the range of from about 0.1 µg/kg to about 100 mg/kg body weight of the patient to be treated. For example, a suitable dosage may be from about 1 µg/kg to about 50 mg/kg body weight per week, from about 100 µg/kg to about 25 mg/kg body weight per week or from about 10 µg/kg to about 12.5 mg/kg body weight per week.

A suitable dosage may be from about 1 µg/kg to about 50 mg/kg body weight per day, from about 100 µg/kg to about 25 mg/kg body weight per day or from about 10 µg/kg to about 12.5 mg/kg body weight per day.

Dosage regimens may be adjusted to provide the optimum desired response (e.g. a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Antibodies may be administered in a single dose or in multiple doses. The multiple doses may be administered via the same or different routes and to the same or different locations. Alternatively, antibodies can be administered as a sustained release formulation, in which case less frequent administration is required. Dosage and frequency may vary depending on the half-life of the antibody in the patient and the duration of treatment that is desired. The dosage and frequency of administration can also vary depending on whether the treatment is prophylactic or therapeutic. In prophylactic applications, a relatively low dosage may be administered at relatively infrequent intervals over a long period of time. In therapeutic applications, a relatively high dosage may be administered, for example until the patient shows partial or complete amelioration of symptoms of disease.

Combined administration of two or more agents may be achieved in a number of different ways. In one embodiment, the antibody or binding fragment thereof and the other agent may be administered together in a single composition. In another embodiment, the antibody and the other agent may be administered in separate compositions as part of a combined therapy. For example, the antibody or binding fragment thereof may be administered before, after or concurrently with the other agent.

Diseases to be Treated

The antibodies or binding fragments thereof of the present invention, or the pharmaceutical compositions as defined herein, are particularly suited for use in the treatment or prevention of pathologies associated with citrullination, such as NET-associated pathologies and inflammatory conditions.

The present invention also encompasses a method of treating a patient comprising administering a therapeutically effective amount of an antibody or binding fragment thereof as defined herein or the pharmaceutical composition as defined herein to a patient, optionally to treat or prevent pathologies associated with citrullination, such as NET-associated pathologies and inflammatory conditions.

The present invention also encompasses an antibody or binding fragment thereof as defined herein or the pharmaceutical composition as defined herein for use in the manufacture of a medicament for the prevention or treatment of pathologies associated with citrullination, such as NET-associated pathologies and inflammatory conditions.

The present invention also encompasses a pharmaceutical composition comprising the antibody or binding fragment thereof of the present invention for treating or preventing pathologies associated with citrullination, such as NET-associated pathologies and inflammatory conditions.

A pathology associated with citrullination can be defined as any disease or condition where citrullination is associated with the pathological state of the disease or condition. Whether or not citrullination plays a role in the pathogenesis of the disease, may be easily determined by a skilled person using routine tests available in the art. For example, these diseases may be characterized by the presence of an abnormal level of citrullinated proteins in affected or disease-related tissue. Such may be accomplished by an immunological test such as a Western blot or an ELISA wherein the affected tissue is used as an antigen and citrullination of that antigen may be detected with the aid of an anti-citrulline antibody as described herein. Alternatively, a person skilled in the art can use Proteomics applications such as mass spectrometry analysis to compare the level and type of citrullination in a diseased versus healthy tissue from affected patients.

NET-associated pathologies can be considered as pathologies associated with citrullination. NET-associated pathologies can be defined as a disease or condition where the formation of NETs and NETosis is associated with the pathological state of the disease or condition. Whether or not NET formation and NETosis plays a role in the pathogenesis of the disease may be easily determined by a skilled person using routine tests available in the art. For example, these diseases may be characterized by the presence of NETs in relevant tissues.

The invention therefore relates to antibodies or binding fragments thereof for use in the treatment or prevention of NET-associated pathologies.

The invention therefore relates to a method of treating a patient in need thereof with a therapeutically effective amount of the antibody or binding fragments thereof of the present invention, wherein the patient is suffering from a NET-associated pathology.

Examples of NET-associated pathologies include inflammatory conditions or diseases, ocular inflammatory diseases, autoimmune diseases, cancer, and organ-health after transplant.

"Inflammatory Conditions" or Inflammatory diseases" refers to any of a number of conditions or diseases, which are characterized by vascular changes: edema and infiltration of neutrophils (e.g., acute inflammatory reactions); infiltration of tissues by mononuclear cells; tissue destruction by inflammatory cells, connective tissue cells and their cellular products; and attempts at repair by connective tissue replacement (e.g., chronic inflammatory reactions). Such diseases are for instance inflammatory arthritis, including rheumatoid arthritis and osteoarthritis, SLE, lupus, sepsis, vasculitis, multiple sclerosis, psoriatic arthritis, psoriasis, Alzheimer's disease, autoimmune hepatitis, juvenile idiopathic arthritis, spondyloarthropathy, multiple system atrophy, Parkinson's disease, Lewy body dementia, idiopathic pulmonary fibrosis, dry eye disease, uveitis, nongranulomatous uveitis, granulomatous uveitis, dermatitis, atopic dermatitis, and lung diseases such as COPD and bronchitis. Nongranulomatous uveitis can be associated with neutrophil dominant inflammation, granulomatous uveitis can be associated with macrophage dominant inflammation.

NETs play a role in autoimmune diseases pathology, including RA, SLE and vasculitis. The pathway by which the therapeutic antibody or binding fragment thereof improves the disease is likely via the inhibition of NETosis, the clearance of NET remnants, including toxic histones, and other auto-antigens from tissue and circulation the clearance of NET remnants and toxic histones from tissue and circulation. For many of several autoimmune diseases it has been shown that the pathology improves in PAD knockout models or in wild-type animals treated with a PAD inhibitor, meaning that there is a strong correlation with the amount of NETs and disease severity.

Thus, inflammatory conditions or diseases and autoimmune diseases can be treated by the antibodies and binding fragments thereof the present invention.

In a preferred embodiment, the diseases to be treated are NET-associated pathologies such as SLE, lupus, sepsis, vasculitis, inflammatory arthritis, rheumatoid arthritis and osteoarthritis, psoriasis, Alzheimer's disease, autoimmune hepatitis, juvenile idiopathic arthritis, Sjögren's disease, Anti-phospholipid Syndrome, Bechet's disease, spondylitis, spondyloarthropathy, multiple system atrophy, Parkinson's disease, Lewy body dementia asthma, allergic rhinovirus exacerbated asthma, allergic asthma, cystic fibrosis, fibrosis and idiopathic pulmonary fibrosis, dry eye disease, uveitis, nongranulomatous uveitis, granulomatous uveitis, dermatitis, atopic dermatitis, COPD, bronchitis, or other NET-associated pathologies such as wound healing in diabetes, cancer, cancer metastasis, and transplant organ health in vivo or ex vivo.

In a preferred embodiment, the diseases to be treated are inflammatory conditions such as SLE, lupus, sepsis, vasculitis, inflammatory arthritis, rheumatoid arthritis and osteoarthritis, psoriasis, Alzheimer's disease, autoimmune hepatitis, juvenile idiopathic arthritis, Sjögren's disease, Anti-phospholipid Syndrome, Bechet's disease, spondylitis, spondyloarthropathy, multiple system atrophy, Parkinson's disease, Lewy body dementia asthma, allergic rhinovirus exacerbated asthma, allergic asthma, cystic fibrosis, fibrosis, idiopathic pulmonary fibrosis, dry eye disease, uveitis, nongranulomatous uveitis, granulomatous uveitis, dermatitis, atopic dermatitis, COPD, bronchitis.

Further Embodiments

The invention is further described by the following embodiments:
1. An antibody or binding fragment thereof that specifically binds to a citrullinated epitope on deiminated human histone 2A and/or histone 4, wherein the antibody or binding fragment thereof comprises:
a) CDR1 of VL, wherein the CDR comprises or consists of the amino acid sequence QSL-$X_1$-D-$X_2$-D-$X_3$-KTY, wherein $X_1$ is V or L, $X_2$ is T, S, A or N and $X_3$ is G or A (SEQ ID NO:57), provided that the amino acid sequence is not QSLLDSDGKTY (SEQ ID NO: 36) or QSLVDSDGKTY (SEQ ID NO: 37); and
b) at least one CDR selected from SEQ ID NOs: 1 to 5.
2. The antibody or binding fragment thereof according to 1, wherein the antibody or binding fragment thereof comprises:
a) CDR1 of VL, wherein the CDR comprises or consists of the amino acid sequence QSL-$X_1$-D-$X_2$-D-$X_3$-KTY, wherein $X_1$ is V or L, $X_2$ is T, S, A or N and $X_3$ is G or A (SEQ ID NO:57), provided that the amino acid sequence is not QSLLDSDGKTY (SEQ ID NO: 36) or QSLVDSDGKTY (SEQ ID NO: 37); and
b) the CDRs of SEQ ID NO: 3 and SEQ ID NO: 5.
3. The antibody or binding fragment thereof according to 2, wherein the antibody or binding fragment thereof comprises:
a) one of the CDRs of SEQ ID NOs: 6, 7, 8, 9 and 10; and
b) the CDRs of SEQ ID NO: 3 and SEQ ID NO: 5.
4. The antibody or binding fragment thereof according to 2, wherein the antibody or binding fragment thereof comprises:
a) CDR1 of VL, wherein the CDR comprises or consists of the amino acid sequence QSL-$X_1$-D-$X_2$-D-$X_3$-KTY, wherein $X_1$ is V or L, $X_2$ is T, S, A or N and $X_3$ is G or A (SEQ ID NO:57), provided that the amino acid sequence is not QSLLDSDGKTY (SEQ ID NO: 36) or QSLVDSDGKTY (SEQ ID NO: 37); and
b) the CDRs of SEQ ID NOs: 1 to 5.
5. The antibody or binding fragment thereof according to any of the preceding embodiments, wherein the antibody or binding fragment thereof comprises:
a) one of the CDRs of SEQ ID NOs: 6, 7, 8, 9 and 10;
b) the CDRs of SEQ ID NOs: 1 to 5.

6. The antibody or binding fragment thereof according to 1 or 2, wherein the antibody or binding fragment thereof comprises:
a) CDR1 of VL, wherein the CDR comprises or consists of the amino acid sequence QSL-$X_1$-D-$X_2$-D-$X_3$-KTY, wherein $X_1$ is V or L, $X_2$ is T, S, A or N and $X_3$ is G or A (SEQ ID NO:57), provided that the amino acid sequence is not QSLLDSDGKTY (SEQ ID NO: 36) or QSLVDSDGKTY (SEQ ID NO: 37);
b) at least one of the CDRs of SEQ ID NO: 4 and 5; and
c)
  i) the heavy chain variable domain amino acid sequence of SEQ ID NO: 11 or 12;
  or
  ii) a fragment of at least 7 amino acids of (i), wherein the antibody or binding fragment thereof retains the ability of being specifically reactive with a citrullinated epitope on deiminated human histone 2A and/or histone 4; or
  iii) a variant of (i) having at least 70% amino acid sequence identity to a sequence of (i), wherein the antibody or binding fragment thereof retains the ability of being specifically reactive with a citrullinated epitope on deiminated human histone 2A and/or histone 4.
7. The antibody or binding fragment thereof according to 6, wherein the antibody or binding fragment thereof comprises:
a) CDR1 of VL, wherein the CDR comprises or consists of the amino acid sequence QSL-$X_1$-D-$X_2$-D-$X_3$-KTY, wherein $X_1$ is V or L, $X_2$ is T, S, A or N and $X_3$ is G or A (SEQ ID NO:57), provided that the amino acid sequence is not QSLLDSDGKTY (SEQ ID NO: 36) or QSLVDSDGKTY (SEQ ID NO: 37);
b) at least one of the CDRs of SEQ ID NO: 4 and 5; and
c) the heavy chain variable domain amino acid sequence of SEQ ID NO: 11 or 12.
8. The antibody or binding fragment thereof according to 7, wherein the antibody or binding fragment thereof comprises:
a) CDR1 of VL, wherein the CDR comprises or consists of the amino acid sequence QSL-$X_1$-D-$X_2$-D-$X_3$-KTY, wherein $X_1$ is V or L, $X_2$ is T, S, A or N and $X_3$ is G or A (SEQ ID NO:57), provided that the amino acid sequence is not QSLLDSDGKTY (SEQ ID NO: 36) or QSLVDSDGKTY (SEQ ID NO: 37);
b) the CDRs of SEQ ID NO: 4 and 5; and
c) the heavy chain variable domain amino acid sequence of SEQ ID NO: 11 or 12.
9. The antibody or binding fragment thereof according to 8, wherein the antibody or binding fragment thereof comprises:
a) one of the CDRs of SEQ ID NOs: 6, 7, 8, 9 and 10;
b) the CDRs of SEQ ID NO: 4 and 5; and
c) the heavy chain variable domain amino acid sequence of SEQ ID NO: 11 or 12.
10. The antibody or binding fragment thereof according to any one of the preceding embodiments, wherein the antibody or binding fragment thereof comprises:
a) the heavy chain variable domain amino acid sequence of SEQ ID NO: 11 and the light chain variable domain amino acid sequence of SEQ ID NO: 13;
b) the heavy chain variable domain amino acid sequence of SEQ ID NO: 11 and the light chain variable domain amino acid sequence of SEQ ID NO: 14;
c) the heavy chain variable domain amino acid sequence of SEQ ID NO: 11 and the light chain variable domain amino acid sequence of SEQ ID NO: 15;

d) the heavy chain variable domain amino acid sequence of SEQ ID NO: 11 and the light chain variable domain amino acid sequence of SEQ ID NO: 16;
e) the heavy chain variable domain amino acid sequence of SEQ ID NO: 11 and the light chain variable domain amino acid sequence of SEQ ID NO: 17;
f) the heavy chain variable domain amino acid sequence of SEQ ID NO: 12 and the light chain variable domain amino acid sequence of SEQ ID NO: 13;
g) the heavy chain variable domain amino acid sequence of SEQ ID NO: 12 and the light chain variable domain amino acid sequence of SEQ ID NO: 14;
h) the heavy chain variable domain amino acid sequence of SEQ ID NO: 12 and the light chain variable domain amino acid sequence of SEQ ID NO: 15;
i) the heavy chain variable domain amino acid sequence of SEQ ID NO: 12 and the light chain variable domain amino acid sequence of SEQ ID NO: 16; or
j) the heavy chain variable domain amino acid sequence of SEQ ID NO: 12 and the light chain variable domain amino acid sequence of SEQ ID NO: 17.

11. An antibody or binding fragment thereof that specifically binds to a citrullinated epitope on deiminated human histone 2A and/or histone 4, wherein the antibody or binding fragment thereof comprises the CDRs of:
a) the CDR1 of SEQ ID NOs: 13, 14, 15, 16 or 17; and
b) the heavy chain variable domain amino acid sequence of SEQ ID NO: 11 or 12.

12. The antibody or binding fragment thereof according to any one of the preceding embodiments, that specifically binds to a peptide selected from the group consisting of SEQ ID NOs: 18, 19, 20, 21 and 22, and binds deiminated human histone 2A and/or histone 4.

13. The antibody or binding fragment thereof according to any one of the preceding embodiments, that specifically binds to a citrullinated epitope on deiminated human histone 2A and/or histone 4, with an affinity of at least 1 nM or less.

14. The antibody or binding fragment thereof according to any one of the preceding embodiments, selected from the group consisting of recombinant antibodies, single chain antibodies, single chain variable fragments (scFv), variable fragments (Fv), fragment antigen-binding regions (Fab), single-domain antibodies (sdAb), VHH antibodies, nanobodies, camelids-derived single-domain antibodies, shark IgNAR-derived single-domain antibody fragments (VNAR), diabodies, triabodies, Anticalins and aptamers.

15. The antibody or binding fragment thereof according to any one of 1 to 13, wherein the antibody is preferably a full-length antibody.

16. The antibody or binding fragment thereof according to 15, which comprises an Fc region, such as an IgG1, IgG2, IgG3 or IgG4 region.

17. The antibody or binding fragment thereof according to 16, wherein the heavy chain constant region comprises SEQ ID NO: 23 and/or the light chain constant region comprises SEQ ID NO: 24.

18. The antibody or binding fragment thereof according to any one of the preceding embodiments conjugated to an additional moiety.

19. A polynucleotide encoding the antibody or binding fragment thereof according to any one of 1 to 17, a cloning or expression vector comprising said polynucleotide, or a host cell comprising said cloning or expression vector.

20. A process for the production of an antibody or binding fragment thereof that specifically binds to a citrullinated epitope on deiminated human histone 2A and/or histone 4, comprising culturing the host cell of 19 and isolating the antibody or binding fragment thereof from said cell.

21. A pharmaceutical composition comprising the antibody or binding fragment thereof according to any one of 1 to 18 and at least one pharmaceutically acceptable diluent or carrier.

22. The pharmaceutical composition according to 21, additionally comprising other active ingredients.

23. The antibody or binding fragment thereof according to any one of 1 to 18, or the pharmaceutical composition according to 21 or 22, for use in therapy.

24. The antibody or binding fragment thereof according to any one of 1 to 18, or the pharmaceutical composition according to 21 or 22, for use in a method of treating or preventing a NET-associated pathology.

25. The antibody, binding fragment thereof or pharmaceutical composition for use according to 24, wherein the NET-associated pathology is systemic lupus erythematosus (SLE), lupus, sepsis, vasculitis, inflammatory arthritis, rheumatoid arthritis and osteoarthritis, psoriasis, Alzheimer's disease, autoimmune hepatitis, juvenile idiopathic arthritis, Sjögren's disease, Anti-phospholipid Syndrome, Bechet's disease, spondylitis, spondyloarthropathy, multiple system atrophy, Parkinson's disease, Lewy body dementia asthma, allergic rhinovirus exacerbated asthma, allergic asthma, cystic fibrosis, fibrosis and idiopathic pulmonary fibrosis, dry eye disease, uveitis, nongranulomatous uveitis, granulomatous uveitis, dermatitis, atopic dermatitis, COPD, bronchitis, or other NET-associated pathologies such as wound healing in diabetes, cancer, cancer metastasis, and transplant organ health in vivo or ex vivo.

26. The antibody, binding fragment thereof or pharmaceutical composition for use according to any one of 23 to 25, wherein the antibody, binding fragment thereof or pharmaceutical composition is administered by parenteral routes of administration such as intravenous, subcutaneous, intraocular, intramuscular, intradermal, intraperitoneal, spinal routes or by injection or infusion; or by other routes such as rectal, oral, ocular, topical, epidermal, mucosal, local, peritumoral, juxtatumoral, intratumoral, to the resection margin of tumors, intralesional, perilesional, by intra cavity infusion, intravesicle administration, or by inhalation.

27. A method of treating a patient comprising administering a therapeutically effective amount of an antibody or binding fragment thereof as defined in any one of 1 to 18, or the pharmaceutical composition according to 21 or 22, to said patient.

28. The method according to 27, wherein the treatment is of a NET-associated pathology.

The present invention is further illustrated by the following examples which should not be construed as further limiting. The contents of all figures and all references, patents and published patent applications cited throughout this application are expressly incorporated herein by reference.

EXAMPLES

Example 1: Accelerated Stability Testing of hMQ22.101j/e and hMQ22.101f/g 0.75 ml Aliquot (glass tubes) containing hMQ22.101j/e (12.5 mg/ml) or hMQ22.101f/g (3.31 mg/ml) in 25 mM Tris-HCl, pH 8.0 were stored at 37° C. each for 8 weeks. Each week several 10 µl and 20 µl samples were withdrawn from each glass tube under aseptic conditions and stored at −80° C. until further analysis (ELISA and mass spectrometry).

hMQ22.101j/e samples from week 0, 2, 4, 6 and 8, and hMQ22.101f/g samples from week 0, 3 and 6 were subjected to an in house-validated CMC ELISA. 96-well ELISA plates were coated with NeutrAvidin™ (0.1 µg/well) by overnight incubation at 4° C. Wells were washed 5 times with PBS-Tween® (polysorbate) 20 (PBS-T) and blocked by a 2 hour incubation with PBS-T+1% Bovine serum albumin (BSA) at room temperature (RT). After 5 more washes with PBS-T, wells were incubated for 1 hour at RT with a histone-derived peptide (SEQ ID NO 18: SGXGKQGGKARA), containing a citrulline (X) at position 3 and a C-terminal biotin (40 ng/well) in PBS-T+0.2% BSA. After another 5 washes with PBS-T, a calibration curve made from a reference lot of hMQ22.101j/e or hMQ22.101f/g by adding to the wells starting at 1350 ng/well and further diluted at a 1:1 ratio until reaching a concentration of 0.66 ng/ml in PBS-T+0.2% BSA. Spiked quality control (QC) samples made from the same reference lot hMQ22.101j/e or hMQ22.101f/g at higher (HQC, 250 ng/ml), middle (MQC, 50 ng/ml), lower (LQC 3.75 ng/ml) and lower limit quality control (LLQC, 1.25 ng/ml) were diluted in PBS-T+0.2% BSA and added to the plate as well. These QC samples were used in order to validate the ELISA results.

Finally, accelerated stability samples that had been incubated for 0, 2, 3, 4, 6 and 8 weeks at 37° C. were added to the same plate at a concentration of 40 ng/ml in PBS-T+ 0.2% BSA and incubated for 2 hours at RT. Wells were washed 5 times with PBS-T and incubated with rabbit anti-human-HRP antibody (1:12.000 in PBS-T+0.2% BSA) for 1 hour at RT followed by 3 washes with PBS-T and 3 washes with PBS. Wells were incubated 10 min with TMB substrate before stopping the reaction with 2 M $H_2SO_4$ after which the optical density was measured at wavelength of 450 nm. A sigmoidal calibration curve was plotted and fitted using the values from the serial diluted reference antibody. Concentrations of the QC samples and accelerated stability samples were recalculated using the equation from the sigmoidal fitted curve. The recalculated antibody concentration from the week 0 accelerated stability sample was set at 100%, and all other accelerated stability recalculated concentrations (week 2, 3, 4, 6 and 8) were calculated as a percentage of week 0 (100%) and plotted in a bar graph (FIG. 1, top panel, for hMQ22.101j/e, FIG. 1, bottom panel, for hMQ22.101f/g).

The accelerated stability testing showed that binding affinity of hMQ22.101j/e and hMQ22.101f/g for the histone-derived citrulline-containing peptide decreased over time.

Example 2: Mass Spectrometry Analysis of hMQ22.101j/e Accelerated Stability Samples The cause of the reduction in binding affinity of the hMQ22.101j/e antibody over time was investigated. hMQ22.101j/e has several potential aspartate isomerization sites in or near the VL CDR regions (CDR1 and CDR2). The aim of this Example was to determine the sensitivity of the aspartate residues towards isomerization by liquid chromatography (LC)-mass spectrometry (MS)-based peptide mapping.

Prior to digestion, 50 µg of each accelerated stability sample (week 0, 4 and 8) was subjected to desalting, reduction with dithiothreitol and alkylation using iodoacetamide. Following reduction and alkylation, the samples were digested for 18 hours at 37° C. using sequencing grade modified trypsin (Promega) in an enzyme/protein ratio of 1/50 (w/w). Digests were stored at −20° C. until LC-MS analysis. Trypsin is a serine protease that specifically cleaves at the C-terminus of either arginine or lysine. Analysis of tryptic digests was performed using reversed-phase liquid chromatography (RPLC) in combination with UV and mass spectrometric detection (RPLC-UV-MS). Data were acquired using an Agilent Technologies™ 1290 UHPLC system hyphenated to an Agilent Technologies™ 6540 Q-TOF equipped with a Jetstream electrospray ionization (ESI) source. Samples were separated on a RPLC column (AdvanceBio™ Peptide Map C18 columns, 250 mm L, 2.1 mm ID, 2.7 µm dp, Agilent Technologies) using water, trifluoroacetic acid and acetonitrile as mobile phase constituents prior to UV 214 nm and MS(/MS) detection. An amount of approximately 4.5 µg was loaded onto the column. The MS system was operated in the extended dynamic range mode (2 GHz) with a resolution of 20,000 for mass 922.009798 and at high mass accuracy (typically <10 ppm) without utilizing reference masses. Two spectra were acquired per second and the acquisition range was 100-3000 amu in MS and MS/MS mode. MS/MS data were acquired in the data-dependent mode. Collision energy was optimized for peptide fragmentation. All MS measurements were performed in the positive ionization mode.

Measured signals were matched onto the sequence using the BioConfirm™ algorithm incorporated in the Agilent MassHunter™ software. Mass tolerance for matching experimental data onto the sequence was set at 20 ppm. Enzyme specified was trypsin (C-terminal cleavage at lysine or arginine) and 0-2 missed cleavages were allowed. Peak areas from extracted ion chromatograms obtained at 20 ppm mass accuracy were used for quantifying modifications. Given the near complete sequence coverage, all candidate aspartate isomerization sites in the hCDR regions were covered. Manual integration of these peptides was performed. When present, the peptide containing isoaspartate elutes just before the peptide containing aspartate. Relative isomerization levels were then calculated in each case.

The relative aspartate (D) isomerization levels of VL CDR1 of hMQ22.101j/e increased over time (FIG. 2A). The isomerization sites tested in CDR1 and CDR2 of the VL are set out in FIG. 2A. The isomerization of VL CDR1 was considered the cause of the loss of binding affinity of the antibody over time.

Example 3: Producing Three VL CDR1 Aspartate-Mutated hMQ22.101 Antibodies

It was then investigated whether deletion of the non-germline isomerization site in CDR1 of VL prevented isomerization. DNA of three hVL22.101y domains, including a single aspartate mutation in CDR1 at amino acid position 31 (L:Asp31) each, were synthesized by GeneArt®. L:Asp31 was mutated into an Alanine, Glutamine or Serine based on amino acid similarities such as 1) size, 2) polarity and 3) charge. These aspartate-mutated VL domains were cloned into a mammalian expression vector encoding a full-length human light chain. Subsequently, these light chain constructs (hVL22.101h, hVL22.101i and hVL22.101j) all in combination with a full-length human heavy chain construct (hVH22.101j) were used to transiently transfect HEK293 cells for the production of hMQ22.101j/h, hMQ22.101j/i and hMQ22.101j/j, respectively. Full-size antibodies were purified from culture supernatants using MabSelect SuRe™ (resin) affinity columns and subsequently buffer exchanged to 25 mM Tris-HCl, pH 8.0 by using desalting columns, both on an Akta-FPLC™ chromatography system. Next, antibodies were polished with ion exchange spin columns to remove host cell proteins and residual Protein A-derived resin, followed by an endotoxin removal step by using high-capacity endotoxin removal resin. Finally, antibodies were concentrated with a MicroSep™ Advance Centrifugal Device (10K MWCO).

Example 4: Antigen Binding Assay with VL CDR1 Aspartate-Mutated hMQ22.101 Antibodies Generated VL CDR1 aspartate-mutated antibodies hMQ22.101j/h, hMQ22.101j/i and hMQ22.101j/j were compared to the aspartate-containing antibody hMQ22.101j/e using an in house validated CMC ELISA as described in Example 1. Here a hMQ22.101j/e reference lot was used for the calibration curve at 5, 10, 20, 30, 40, 60, 80 and 100 ng/ml and separate spiked QC samples at 10, 20, 60 and 80 ng/ml. hMQ22.101j/h, hMQ22.101j/i, hMQ22.101j/j and hMQ22.101j/e were tested at 10, 20, 30, 40, 80 and 100 ng/ml, and dose response curves plotted in a graph (FIG. 2B).

FIG. 2B shows the optical density results of the three VL CDR1 mutants (CDR1 of hVL22.101h=mutation of DS site to AS; CDR1 of hVL22.101i=mutation of DS site to ES; CDR1 of hVL22.101j=mutation of DS site to SS). The most improved optical density results were achieved by the hMQ22.101j/i antibody.

Example 5: Accelerated Stability Test Followed by Mass Spectrometry Analysis of VL CDR1 Aspartate-Mutated hMQ22.101j/i 0.75 ml Aliquot (glass tubes) containing hMQ22.101j/i (12.5 mg/ml) in 25 mM Tris-HCl, pH 8.0 were stored at 37° C. each for 4 weeks. Each week several 10 µl and 20 µl samples were withdrawn from each glass tube under aseptic conditions and stored at −80° C. until further analysis (mass spectrometry).

The mass spectrometry analysis was performed identically to the methods described in Example 2, with the difference that accelerated stability samples from week 0 and 4 were used only. Percentages of isomerization for hMQ22.101j/i were compared to those from isomerization containing antibody hMQ22.101j/e (FIG. 2C).

Mass spectrometry data for the hMQ22.101j/i antibody (FIG. 2C) showed that isomerization in the CDR1 of VL still increased a little over time, however, deletion of the non-germline DS isomerization site in CDR1 of the VL did largely solve the isomerization problem.

However, hMQ22.101j/i had less affinity for the target (SEQ ID NO: 18) compared to hMQ22.101j/e, thus it was not a suitable therapeutic antibody candidate.

Example 6: Producing Other hMQ22.101 Isomerization Mutants

A comprehensive mutation analysis of the isomerization sites in CDR1 of VL was then carried out, to investigate whether it was possible to remove isomerization of CDR1 whilst keeping affinity of the mutated antibody for its target. Seventeen mutated CDR1 domains of hVL22.101 were created. These seventeen VL CDR1-mutated sequences, and the sequences of un-mutated CDR1 of hVL22.101e and hVL22.101g are set out in FIG. 3A.

DNA of seventeen mutated VL CDR1 domains of hVL22.101 and four VH domain variants of hVH22.101 were synthesized by GeneArt®. All mutated VL and VH domains were cloned into mammalian expression vectors encoding full-length human light and heavy chains, respectively. The seventeen mutant light chains (hVL22.101LC16, hVL22.101LC17, hVL22.101LC19, hVL22.101LC20, hVL22.101LC21, hVL22.101LC22, hVL22.101LC23, hVL22.101LC24, hVL22.101LC25, hVL22.101LC26, hVL22.101LC27, hVL22.101LC37, hVL22.101LC38, hVL22.101LC39, hVL22.101LC40, hVL22.101LC41 and hVL22.101LC42) were combined with the non-variant heavy chain hVH22.101j or with the four variant heavy chains (hVH22.101HC7, hVH22.101HC8, hVH22.101HC9, hVH22.101HC10). Thus, all possible combinations of light chain (hVL22.101e, hVL22.101LC16, hVL22.101LC17, hVL22.101LC19, hVL22.101LC20, hVL22.101LC21, hVL22.101LC22, hVL22.101LC23, hVL22.101LC24, hVL22.101LC25, hVL22.101LC26, hVL22.101LC27, hVL22.101LC37, hVL22.101LC38, hVL22.101LC39, hVL22.101LC40, hVL22.101LC41 and hVL22.101LC42) and heavy chain (hVH22.101j, hVH22.101HC7, hVH22.101HC8, hVH22.101HC9, hVH22.101HC10) constructs were used to transiently transfect HEK293 cells for the production of full-size antibodies (isomerization mutants). Antibodies were purified, desalted, polished, and concentrated as described in Example 3.

Example 7: Dissociation Rate Analysis of hMQ22.101 Isomerization Mutants

Off-rate screening of the isomerization-mutated antibodies was performed on an Octet® RED96 (biomolecule detection system) instrument (Pall ForteBio). All measurements were performed at 30° C. Streptavidin (SA) biosensors were first washed for 50 sec with PBS. 1 ug/ml N-terminal histone 2A (SEQ ID NO: 18) and histone 4 (SEQ ID NO: 20) peptides, containing both a citrulline at position 3 and a biotin at the C-terminus, were immobilized on SA biosensors for 200 sec, washed with PBS for 50 sec and excess reactive streptavidin molecules blocked with EZ-Link™ biocytin for 200 sec. After two additional 50 sec wash steps in PBS, antibodies at a concentration of 72 nM diluted in PBS were allowed to bind to the biosensors for 200 sec. Sensors were subsequently placed in PBS for 4000 sec in order to measure their dissociation rates.

Background signals generated with non-coated biosensors, which have been exposed to the various antibodies as well as signals from coated biosensors that have not been exposed to the various antibodies, have been subtracted before dissociation curves for each antibody were plotted. Both histone 2A and histone 4 dissociation rates constants ($k_{dis}\times$E-07 (l/s)) for each antibody were calculated applying a 1:1 interaction model (fitting local, full) using ForteBio data analysis software 8.1.

The results are shown in FIG. 3B. Lower numbers indicate slower off-rate, which means slower release of the antigen. 1×E-07 l/s is the minimum value, which is detected by Octet, meaning almost no off-rate measurable.

Several hMQ22.101 isomerization mutants showed a dissociation rate of 1×E-07 l/s. Preferred heavy chains: hVH22.101j and hVH22.101HC9. Preferred light chains: hVL22.101LC17, hVL22.101LC21, hVL22.101LC27, hVL22.101LC41 and hVL22.101LC42.

Example 8: Accelerated Stability Testing of the 9 Best hMQ22.101 Isomerization Mutants 0.4 ml Aliquot (glass tubes) from the following selected mutated antibodies (range of 2.06-4.29 mg/ml) in 25 mM Tris-HCl, pH 8.0 were stored at 37° C. each for 6 weeks.

hMQ22.101f/LC17
hMQ22.101f/LC27
hMQ22.101f/LC41
hMQ22.101f/LC42
hMQ22.101HC9/LC17
hMQ22.101HC9/LC21
hMQ22.101HC9/LC27
hMQ22.101HC9/LC41
hMQ22.101HC9/LC42

Each week several 10 µl and 20 µl samples were withdrawn from each glass tube under aseptic conditions and stored at −80° C. until further analysis (ELISA and MS analysis). Antibody samples from week 0, 3, and 6 were subjected to an in house-validated CMC ELISA as described in Example 1, with the difference that only the hMQ22.101f/g reference lot was used for the calibration curve and the HQC, MQC, LQC and LLQC spiked QC samples.

The results are shown in FIG. 4. The 5 best performing isomerization mutants (hMQ22.101f/LC41, hMQ22.101f/LC42, hMQ22.101HC9/LC21, hMQ22.101HC9/LC27, hMQ22.101HC9/LC42, boxed) were used to assess isomerization at week 0 and 6 via MS analysis.

Example 9: Mass Spectrometry Analysis of the 5 Best hMQ22.101 Isomerization Mutants The 37° C. accelerated stability samples from the 5 antibodies, which performed best in the accelerated stability test (Example 5), were further analyzed for their isomerization levels in CDR1 of VL by MS analysis.

hMQ22.101f/LC41
hMQ22.101f/LC42
hMQ22.101HC9/LC21
hMQ22.101HC9/LC27
hMQ22.101HC9/LC42

The MS analysis was performed identically to the methods described in Example 2, with the difference that accelerated stability samples from week 0 and 6 were used only. Percentages of isomerization were compared to those from antibody hMQ22.101j/e (FIG. 5). hMQ22.101f/LC41 showed almost no isomerization (0.5%) over time and was considered the preferred candidate. Second best antibodies were hMQ22.101f/LC42 and hMQ22.101HC9/LC42. The preferred second best antibody was hMQ22.101f/LC42, as HC chain f is more human than HC9, and the difference in isomerization between week 0 and 6 is smaller (1.9% versus 2.6%).

Example 10: Aggregation and Degradation Analysis of the 3 Best Performing hMQ22.101 Isomerization Mutants The 37° C. accelerated stability samples from the 3 antibodies, which showed less isomerization in their CDR1 of VL (Example 6), were further analyzed regarding their aggregation and degradation levels.

hMQ22.101f/LC41
hMQ22.101f/LC42
hMQ22.101HC9/LC42

Measurements were carried out on an Agilent™ 1200 system, equipped with G1311A quaternary pump, G1322A degasser, G1329A autosampler, G1330B thermostat, G1316A column oven and G1314B VWD detector (Agilent Technologies) in combination with an Agilent Zorbax® GF-250 (gel filtration column), 4 µm, 9.4×250 mm column. 10 µl Antibody was injected and run for 10 min at a flow rate of 2 ml/min, using a mobile phase consisting of 200 mM $NaH_2PO_4$ in $H_2O$, pH 7.0. Proteins have been detected using 240 nm UV-light. Main antibody peak was detected at approximately 4.25 min. Shoulders before and after the main peak were quantified and are a measure of aggregation and degradation levels, respectively. The results are shown in FIG. 6.

hMQ22.101f/LC41, hMQ22.101f/LC42 and hMQ22.101HC9/LC42 showed acceptable aggregation and degradation profiles, indicated that they are acceptable for further development.

Example 11: Fragmentation Analysis of the Best Performing hMQ22.101 Isomerization Mutants Analysis of the intact mAb samples was performed using reversed-phase liquid chromatography (RP-HPLC) in combination with UV and mass spectrometric (MS) detection (RP-HPLC-UV-MS). Data were acquired using an Agilent Technologies™ 1290 UHPLC system hyphenated to an Agilent Technologies™ 6540 Q-TOF equipped with a Jetstream electrospray ionization (ESI) source. Samples were separated on a RPLC column (Zorbax® 300 SB-C8 (gel filtration column), 100 mm L, 2.1 mm ID, 1.8 µm dp, Agilent Technologies) using 0.1% TFA in water as mobile phase A and 0.1% TFA in acetonitrile as mobile phase B. A gradient from 15% B to 80% B was applied over 65 minutes. Approximately 5 µg was loaded onto the column. The MS system was operated in the high-resolution mode (4 GHz) with a fragmentor voltage of 350 V and a Quad AMU setting of 300. One spectrum was acquired per second with an acquisition range of 300-3200 amu in positive MS mode. The raw spectra were deconvoluted using a maximum entropy algorithm incorporated in Agilent Technologies MassHunter™ software with BioConfirm™ add-on. The measured MW was compared to the theoretical MW determined by the full sequence, taking potential C-terminal lysine truncation and N-glycosylation into account.

Using RP-HPLC-UV-MS analysis an increase in fragmentation was observed for both hMQ22.101f/LC41 and hMQ22.101j/e samples incubated for 6 weeks at 37° C. if compared to unstressed samples. The amount of fragmentation was similar to fragmentation profiles observed for other therapeutic antibodies used for clinical studies and is acceptable.

Example 12: Human Neutrophil Extracellular Trap Assay

Whole blood was collected in sodium heparin tubes (Beckton Dickinson) from 2 different healthy donors. 30 ml Blood per donor was mixed with 15 ml 6% dextran in 0.9% NaCl and incubated for 60 min at RT. After incubation two clear layers were visible, a bottom layer containing most of the erythrocytes and a top layer containing the neutrophils. The top layer was collected and spun down 10 min at 300 g at RT. The pellet was resuspended in 25 ml PBS and neutrophils were isolated by density gradient centrifugation with Ficoll-Paque® Plus (GE Healthcare) followed by a 10 min erythrocyte lysis step at RT. Cells were counted using a Guava® EasyCyte™ flow cytometer. 900.000 Neutrophils per well were seeded into 24-well tissue culture plates (Greiner bio-one) in neutrophil extracellular trap (NET) assay buffer (RPMI 1640 medium containing GlutaMAX™ (Life Technologies)) supplemented with 1% heat-inactivated fetal bovine serum and 1 mM $CaCl_2$. Neutrophils were stimulated during 4 hours with calcium ionophore A23187 (Molecular Probes). The effect of NET-reducing antibodies was tested by adding one of the following antibodies at a concentration of 25 µg/ml (hMQ22.101f/g, hMQ22.101f/LC41, hMQ22.101f/LC42, and isotype control antibody MQR2.201) or assay buffer 15 min prior to A23187 to the cells. After 4 hours of incubation at 37° C. and 5% $CO_2$, cells were washed very delicately twice using NET assay buffer. Extracellular DNA was subsequently digested with S7 nuclease (7.5U/0.5 ml) for 15 min at 37° C., after which 10 µl 500 mM EDTA was added to stop further digestion. NETs were harvested from the wells and spun down for 5 min at 20 g in order to get rid of intact cells. The amount of NETs were quantified by measuring the MPO activity in the sample by adding 50 µl 3,3',5,5'-Tetramethylbenzidine (TMB) substrate to 50 µl harvested NETs. After an incubation of 10 min at RT 50 µl $H_2SO_4$ was added and optical density measured at 450 nm. Background signals coming from neutrophils, which have not been subjected to A23187 treatment, were subtracted and signals from A23187+MQR2.201-treated neutrophils were set at 100%. Signals from all other antibody-treated groups were compared to the A23187+MQR2.201-treated group (FIG. 7).

Surprisingly, development candidate hMQ22.101f/LC41 outperforms hMQ22.101f/LC42 and hMQ22.101f/g at a concentration of 25 µg/ml (n=2). Not only did the isomerization mutant antibody maintain the properties of the non-mutated antibody, but also improved upon them.

Example 13: Experimental Mouse Model for Inflammation

The goal of the study was to test a dose response range with the designated development candidate hMQ22.101f/LC41 or hMQ22.101f/LC42 (wherein isomerization issues were removed), in comparison with an earlier candidate hMQ22.101f/g and isotype-matched control antibody MQR2.201 in the Collagen Antibody Induced Arthritis (CAIA) mouse model. Paw and ankle swelling were quantified.

The commercially available CAIA mouse model from ModiQuest Research B.V. (cat no: MQ18.101) was used according to manufacturer's specifications to induce arthritis in mice. For that purpose, 2.8 mg anti-collagen-II antibody mix was injected i.p. in DBA/J1 mice. Three days later, mice received another i.p. injection containing 25 µg LPS to synchronize the inflammation between mice. Simultaneous with LPS, mice received tACPAs hMQ22.101f/g, hMQ22.101f/LC41, or hMQ22.101f/LC42 (6.25, 12.5, and 25 mg/kg), non-related isotype-matched control antibody MQR2.201 (25 mg/kg), or placebo (physiological salt solution of 0.9% NaCl). Typically, inflammation in the front and hind paws became visible as from 2 days after LPS injection (i.e. day 5). The degree of swelling in the paws was macroscopically scored from day 0, for a time period of 13 days. The maximum degree of swelling score is 8 (divided over 4 paws). For scoring system see table below.

| | |
|---|---|
| 1-2 Swollen toes | 0.25 |
| 3-4 Swollen toes | 0.50 |
| Slightly swollen footpad or ankle | 0.50-0.75 |
| Swollen footpad or ankle +/− toes | 1.00 |
| Swollen toes + slightly swollen footpad | 1.25 |
| Swollen toes + swollen footpad | 1.5 |
| Swollen footpad + swollen ankle | 2.00 |

The results are shown in FIG. 8. Mice that were treated with a therapeutic antibody showed a significantly reduced inflammation in their paws in a dose-dependent manner, as compared to mice treated with control antibody or physiological salt solution. Both optimized lead antibodies hMQ22.101f/LC41 and hMQ22.101f/LC42 (wherein isomerization issues were removed) prevented inflammation even more than previous lead candidate hMQ22.101f/g, which is clearly shown at a 25 mg/kg dose (FIG. 8, top panel). No adverse effects were observed. At the lowest dose of 6.25 mg/kg (FIG. 8, bottom panel), hMQ22.101f/LC41 outperformed all other antibodies, with Student t-test p values on day 13 of p<0.001, p<0.05 and p=0.46 for hMQ22.101f/LC41, hMQ22.101f/LC42 and hMQ22.101f/g, respectively, compared to placebo-treated group.

Example 14: Further Characterization of Development Candidate hMQ22.101f/LC41 in a Mouse In Vitro NET Assay To further strengthen the notion that hMQ22.101f/LC41 is a potent inhibitor of NET formation, binding of hMQ22.101f/LC41 to mouse NETs and pre-NETs, as well as inhibition of mouse NET formation have been studied as set out below. Pre-NETs are defined as neutrophils with an amorphous decondensed nuclear structure containing citrullinated chromatin that still appears intracellularly, having a collapsed nuclear membrane.

The goal of this study was to test whether the designated development candidate hMQ22.101f/LC41 is able to inhibit mouse NET formation. Neutrophils were isolated from bone marrow of C57BL/6J mice by negative selection using the EasySep™ mouse neutrophil enrichment kit (Stemcell Technologies) according to the manufacturer's instruction. Purity of isolated neutrophils was checked by flow cytometry using an antibody to Ly6G (Biolegend) and was above 90%. Isolated bone marrow neutrophils were adjusted to a concentration of $2 \times 10^6$ cells/ml in HBSS containing calcium and magnesium. A total of 100 µl of cell suspension was added to each well of an 8-well chamber slide (Thermo Fisher Scientific). 25 µg/ml hMQ22.101f/LC41, MQR2.201 or no antibody were allowed to incubate with the cells for 15 min before adding 150 µl of HBSS containing 1 µg/ml A23187 or vehicle control to the cells. The chamber slide was incubated for 3h at 37° C. and 5% $CO_2$. Subsequently, 2% (v/v) paraformaldehyde (Merck) was added to each well and the preparations incubated for 12h at 4° C. Samples were blocked with 10% fetal calf serum (FCS; Biochrome) in PBS for 1 h at room temperature. Primary rabbit anti-citH3 antibody (Abcam, ab5103; 1:200), or TRITC-conjugated goat anti-human IgG (Jackson Immunoresearch, 109-025-003; 1:100) were added in 10% FCS in PBS for 12h at 4° C. Slides were washed three times with PBS, and secondary Cy5-conjugated goat anti-rabbit IgG antibody (Jackson ImmunoResearch, 111-175-144; 1:400) was added for 1.5h at room temperature in the dark. Slides were again washed three times with PBS Staining solution containing 2.5 µM Hoechst in PBS was added for 15 min at room temperature. After washing with PBS, samples were embedded in mounting medium (BIOZOL). Slides were analyzed on a BZ-X710 microscope (Keyence), and NETs and pre-NETs quantified by Fiji imaging software (FIG. 9A). Representative images showing hMQ22.101f/LC41 binding (hIgG; red) to NETs (yellow arrow) and pre-NETs (white arrow) are shown in FIG. 9B.

In vitro treatment of mouse bone marrow (BM)-derived neutrophils with hMQ22.101f/LC41 resulted in reduced A23187-induced NET extrusion compared to MQR2.201-treated mouse BM-derived neutrophils (FIG. 9A). In addition, hMQ22.101f/LC41 binds to expelled mouse NETs (FIG. 9B; yellow arrow) and pre-NETs (FIG. 9B; white arrow), which could be the first step towards NET clearance by macrophages.

Example 15: Further Characterization of Development Candidate hMQ22.101f/LC41 in a Mouse In Vivo NET/Macrophage Assay Using Pristane-Induced Peritonitis Mouse Model The ability of the development candidate hMQ22.101f/LC41 to inhibit NET formation in vivo was tested using a pristane-induced mouse model of peritoneal cell influx that has previously been described by Kienhöfer et al (JCI Insight 2017; 2(1): e92920).

In brief, 50 mg/kg MQR2.201 or hMQ22.101f/LC41 was administered immediately after injection of 500 µl pristane oil (Sigma-Aldrich), followed by a second injection of 50 mg/kg MQR2.201 or hMQ22.101f/LC41 12 hours later. After a total of 24 hours, inflammatory cells were isolated from the peritoneum, adjusted to $1\times10^6$ cells/ml and transferred to either flow chamber slides or cytospin slides for analysis via immune fluorescence microscopy. Slides were subsequently blocked with PBS+10% FCS and incubated with rabbit anti-citH3 (Abcam, ab5103; 1:200), rabbit anti-NE (Abcam, ab21595; 1:200), Alexa Fluor 488® (dye)-conjugated rat anti-mouse F4/80 (Biolegend, 123120; 1:200) or TRITC-conjugated goat anti-human IgG (Jackson Immunoresearch, 109-025-003; 1:100). Slides were washed three times with PBS and secondary Cy5-conjugated goat anti-rabbit IgG antibody (Jackson ImmunoResearch, 111-175-144; 1:400) was added for 1.5 h at room temperature in the dark. Slides were again washed three times with PBS. Staining solution containing 2.5 µM Hoechst in PBS was added for 15 min at room temperature. After washing with PBS, samples were embedded in mounting medium (BIOZOL). Slides were analyzed on a BZ-X710 microscope (Keyence) (FIG. 10A and FIG. 10C), and NETs and pre-NETs quantified by Fiji imaging software (FIG. 10B). FIG. 10C shows binding of hMQ22.101f/LC41 to NETs and pre-NETs. FIG. 11 shows uptake of hMQ22.101f/LC41-enriched NETs by macrophages.

Decreased NET filaments, containing DNA and citrullinated Histone 3 (citH3), are observed in peritoneal cells from hMQ22.101f/LC41-treated mice when compared to peritoneal cells from MQR2.201-treated mice (FIG. 10A). Quantification of NETs (colocalization of citH3 and DNA (Hoechst)) confirmed this observation (FIG. 10B). Colocalization of DNA and citH3 is a hallmark of NET formation. Furthermore, hMQ22.101f/LC41 binds to expelled mouse NETs as well as to mouse pre-NETs (FIG. 10C), which could be the first step towards NET clearance by macrophages. Indeed, F4/80-positive macrophages were observed among the cellular infiltrates, which contained phagocytosed hMQ22.101f/LC41 in combination with citH3 or neutrophil elastase (FIG. 11).

Example 16: CIA Mouse Model of RA

To investigate the efficacy of tACPA on NET-induced tissue damage, different tapered tACPA strategies were used in a chronic collagen-induced arthritis (CIA) mouse model of RA.

Figure 12B:
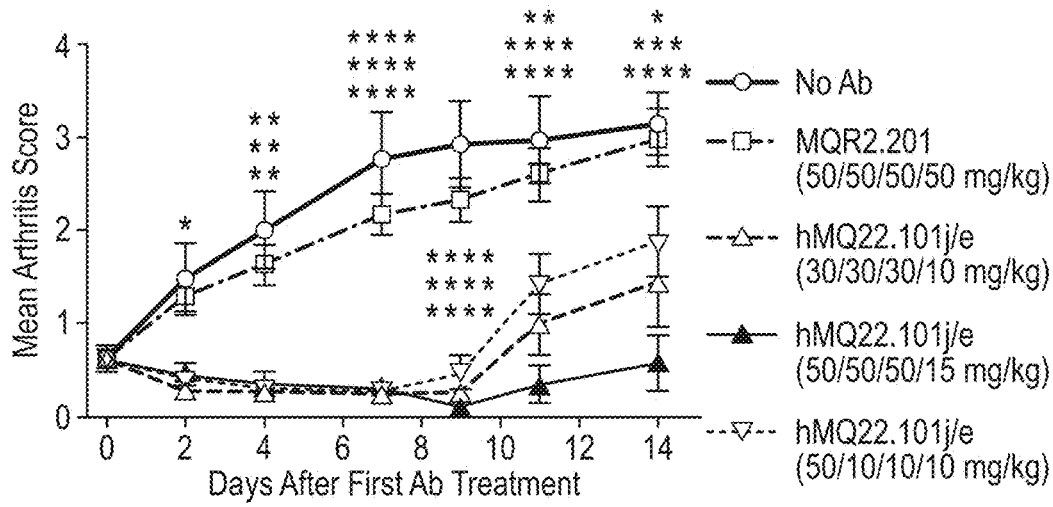

To induce chronic arthritis, bovine Collagen II was diluted to a concentration of 2 mg/ml in 0.05 M acetic acid and emulsified in equal volumes of Freund's complete adjuvant. On day 0, 10-12 weeks old male DBA/J1 mice were immunized intradermally at the tail base with 100 µg bovine CII. On day 21, mice received i.p. booster injections of 50 bovine CII dissolved in PBS and the onset of arthritis occurred a few days later (FIG. 12A). Mice were considered to have arthritis when significant changes of redness and/or swelling were noted in the digits or in other parts of the paws. Joint inflammation in each paw was scored as described above (CAIA mouse model of RA). Therapeutic treatment was started early after onset of disease (between day 21-28) when the mean arthritis score (MAS) were >0.75 on an arbitrary scale of 0-8 (0-2 per paw). Therapeutic administration with four repeated i.v. injections four days apart from each other with indicated doses of hMQ22.101j/e (50/10/10/10, 30/30/30/10, and 50/50/50/15 mg/kg) reduced the MAS at day 14 with 38%, 52%, and 81%, respectively, compared to 50/50/50/50 mg/kg MQR2.201 (FIG. 12B). Mice were terminated at day 14 after start of treatment. The ankle and knee joints were collected and stored in formalin for histological analysis.

It is noteworthy to mention that all hMQ22.101j/e treatments prevented disease development during the first 8 days, after which the MAS started to rise, possibly due to the development of anti-drug antibodies in these mice. Only treatment with 50/50/50/15 mg/kg hMQ22.101j/e completely stabilized the disease for a total of 14 days, not exceeding a MAS of 0.75.

Figure 12C:
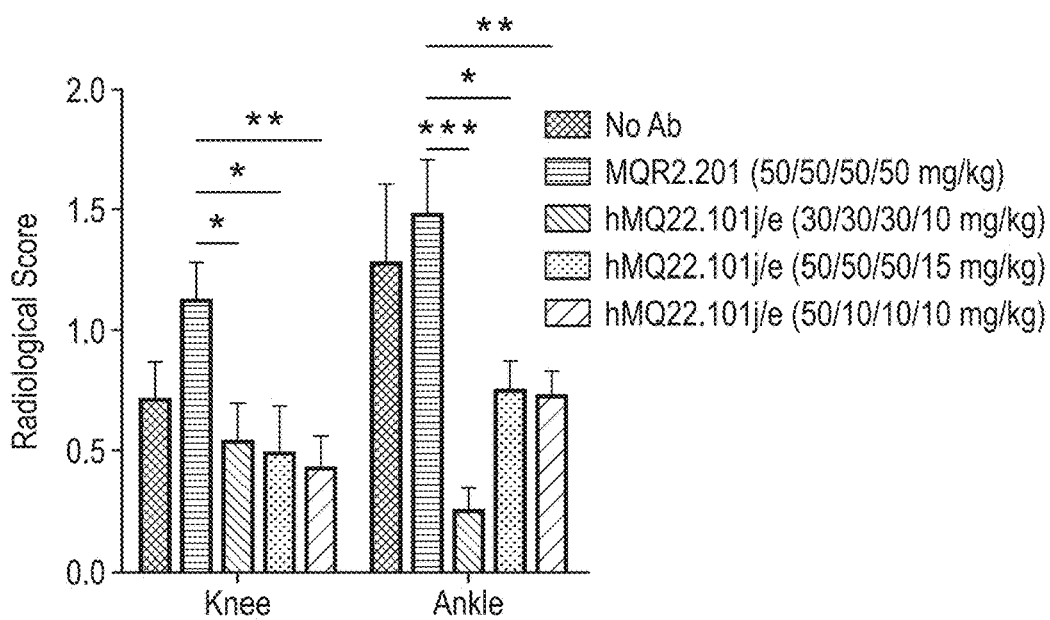

To further study the effect of tACPA on bone damage, X-ray analysis was performed of the knees and ankles of all hind paws from hMQ22.101j/e and MQR2.201 treatment regimens. In line with the observed MAS, all hMQ22.101j/e treatments suppressed bone damage in both ankles and knees (FIG. 12C). To obtain further insight in the protective effect of tACPA, histological analysis of ankle joints was performed, using H&E and safranin O (SO) staining Compared to MQR2.201-treated mice, hMQ22.101j/e inhibited inflammatory cell influx (FIG. 12D). Furthermore, compared to MQR2.201-treated mice, hMQ22.101j/e significantly reduced bone and cartilage erosion as well as cartilage proteoglycan depletion and chondrocyte death (FIG. 12E to FIG. 12H). These data indicate that tACPA strongly mitigates symptoms of arthritis including joint damage.

Figure 12I:
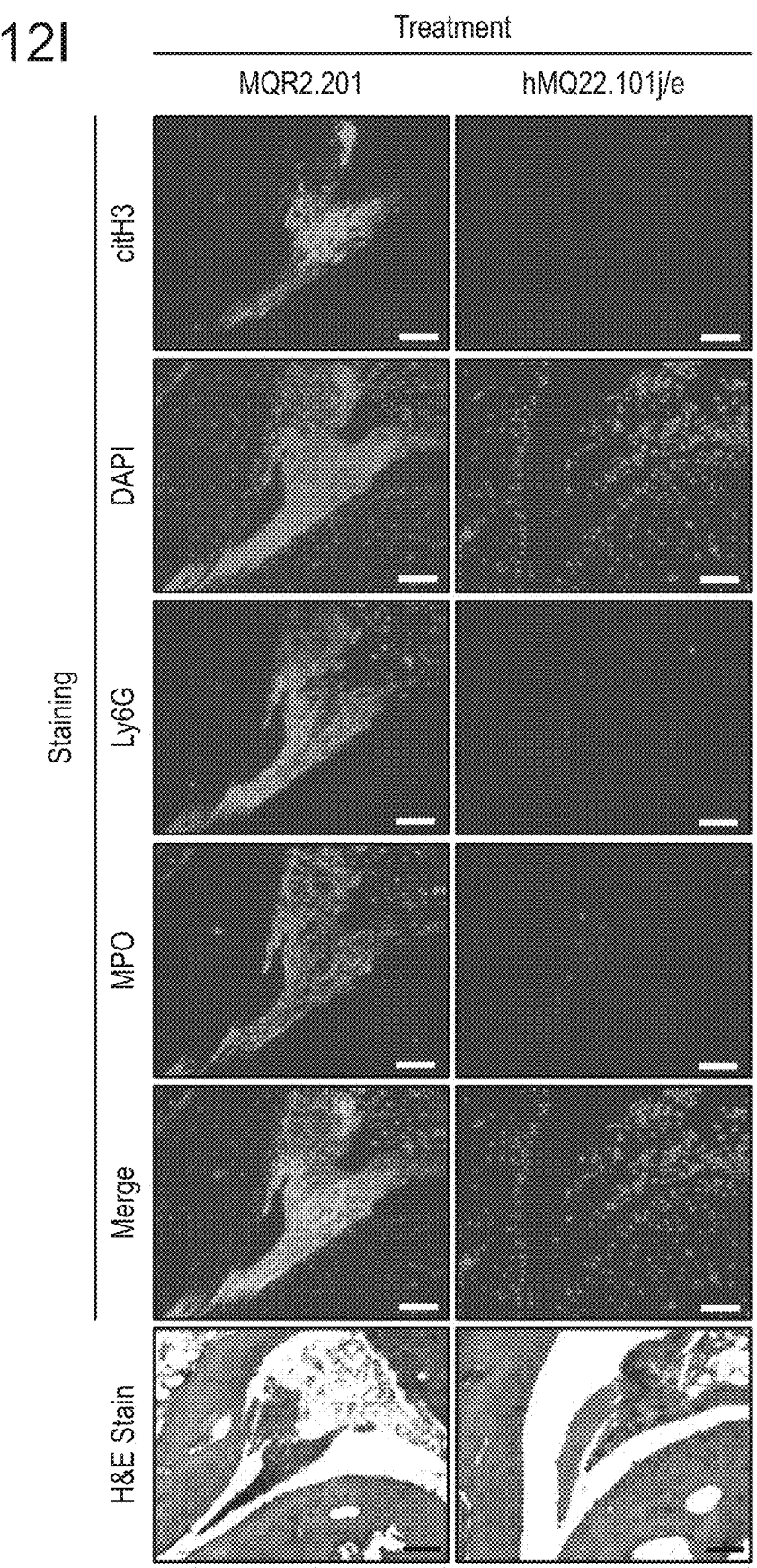

We then investigated the presence of neutrophils and NETs in the paws of CIA mice that received 50/50/50/15 mg/kg of hMQ22.101j/e or 50/50/50/50 mg/kg MQR2.201. The mouse neutrophil marker Ly6G, citrullinated histone 3 (citH3), and myeloperoxidase (MPO) were demonstrated in MQR2.201-treated animals, whereas these markers were near to absent in hMQ22.101j/e-treated mice (FIG. 12I). DAPI was used as a nuclear and extracellular DNA stain (FIG. 12I). Quantification of neutrophils (Ly6G) and NETs (colocalization of citH3 and MPO) was performed by the analysis of multiple joints of the right hind paw of each animal, including the tibiotarsal joint, the proximal intertarsal joint, the distal intertarsal joint, and the tarsometatarsal joint. Compared to MQR2.201-treated mice, a decreased amount of both neutrophils (FIG. 12J) and NETs (FIG. 12K) were observed in the joints of hMQ22.101j/e-treated mice.

We found that the amount of NETs in the joint was significantly correlated with macroscopical paw swelling (FIG. 12L; r=0.6120, P=0.0041). Likewise, a significant correlation was observed between paw swelling and the presence of neutrophils in the joint (FIG. 12M; r=0.8729, P<0.0001). Together, these data indicate that tACPA treatment results in eradication of NETs in inflamed tissue in vivo, thereby preventing severe bone and tissue destruction.

Example 17: hMQ22.101j/e does not Bind to Healthy Leukocytes

Blood from healthy volunteers (HVs), collected in lithium-heparin tubes, was obtained from the Sanquin blood bank in Nijmegen, The Netherlands. All blood donors gave informed consent. Ficoll® density gradient centrifugation was performed to separate peripheral blood mononuclear cells (PBMCs) and neutrophils. PBMCs were collected and washed three times with RPMI 1640 supplemented with 10% (v/v) heat-inactivated fetal calf serum (FCS) and 50 U/ml Penicillin-Streptomycin (referred as RPMI 10% hereafter) to remove platelets. Neutrophils/erythrocyte suspension was mixed with 6% (w/v) dextran in 0.9% NaCl and incubated for 25 min at room temperature. Subsequently, neutrophils were collected, exposed to ammonium-chloride-potassium (ACK) buffer for 10 min at room temperature for lysis of the leftover erythrocytes, and washed two times with RPMI 10%.

PBMCs and neutrophils were seeded in a 96-wells V-bottom plate at a density of $2 \times 10^5$ cells/well in FACS buffer. Cells were incubate with Human Trustain FcX™ (1:50 diluted in FACS buffer) for 20 min at room temperature to block Fc receptors. Subsequently, PBMCs were incubated for 45 min at room temperature with an antibody mix containing 6.25 µg/ml HiLyte™ Fluor 488 (dye)-conjugated hMQ22.101j/e, 0.17 µg/ml anti-CD3, 1 µg/ml anti-CD11c, 0.33 µg/ml anti-CD14, 0.17 µg/ml anti-CD20, 83 ng/ml anti-CD45, and 0.17 µg/ml anti-CD56, while neutrophils were incubated with an antibody mix that contains 6.25 µg/ml HiLyte™ Fluor 488 (dye)-conjugated hMQ22.101j/e, 83 ng/ml anti-CD45, and 83 ng/ml anti-CD66b. As a positive control for HiLyte™ Fluor 488 (dye)-conjugated hMQ22.101j/e binding, neutrophils were stimulated for 45 min with 5 µM A23187 prior to Fc receptor block. After antibody incubation, PBMCs and neutrophils were fixed with 4% formaldehyde for 15 min at room temperature, washed with FACS buffer, and analyzed with the Cyto-FLEX® Flow Cytometer.

HiLyte™ Fluor 488 (dye)-conjugated hMQ22.101j/e did not bind to healthy quiescent T cells, B cells, monocytes, natural killer (NK) cells dendritic cells (DCs) or neutrophils but did bind to activated neutrophils (FIG. 13). Comparable results are expected for the hMQ22.101f/LC41 antibody.

```
Sequence listing

SEQ ID NO: 1-CDR1 of msVH22.101 and hVH22.101(HC)x
GYTFTNYG

SEQ ID NO: 2-CDR2 of msVH22.101 and hVH22.101(HC)x
INTYSGEA

SEQ ID NO: 3-CDR3 of msVH22.101 and hVH22.101(HC)x
LRGYTYQSFDEGGDY

SEQ ID NO: 4-CDR2 of msVL22 101 and hVL22.101(LC)y
LVS

SEQ ID NO: 5-CDR3 of msVL22.101 and hVL22.101(LC)y
WQGTHFPYT

SEQ ID NO: 6-CDR1 of hVL22.101LC17
QSLLDTDGKTY

SEQ ID NO: 7-CDR1 of hVL22.101LC21
QSLLDSDAKTY

SEQ ID NO: 8-CDR1 of hVL22.101LC27
QSLLDTDAKTY

SEQ ID NO: 9-CDR1 of hVL22.101LC41
QSLLDADGKTY

SEQ ID NO: 10-CDR1 of hVL22.101LC42
QSLLDNDGKTY

SEQ ID NO: 11-hVH22.101f
RIQLVQSGAEVKKPGASVKVSCKASGYTFTNYGMHWVRQAPGQGLEWMGWINTYSGEATYAQKFQGRVTMTRDTSISTAYM
ELSRLRSDDTAVYYCLRGYTYQSFDEGGDYWGQGTLVTVSS

SEQ ID NO: 12-hVH22.101HC9
RIQLVQSGAEVKKPGASVKVSCKASGYTFTNYGMHWVRQAPGQGLEWMGWINTYSGEATYVDDFQGRVTMTRDTSISTAYM
ELSRLRSDDTAVYYCLRGYTYQSFDEGGDYWGQGTLVTVSS

SEQ ID NO: 13-hVL22.101LC17
DVVMTQSPLSLPVTLGQPASISCRSSQSLLDTDGKTYLNWFQQRPGQSPRRLIYLVSKLDSGVPDRFSGSGSGTDFTLKIS
RVEAEDVGVYYCWQGTHFPYTFGQGTKLEIK

SEQ ID NO: 14-hVL22.101LC21
DVVMTQSPLSLPVTLGQPASISCRSSQSLLDSDAKTYLNWFQQRPGQSPRRLIYLVSKLDSGVPDRFSGSGSGTDFTLKIS
RVEAEDVGVYYCWQGTHFPYTFGQGTKLEIK
```

| Sequence listing |
|---|

SEQ ID NO: 15-hVL22.101LC27
DVVMTQSPLSLPVTLGQPASISCRSSQSLLDTDAKTYLNWFQQRPGQSPRRLIYLVSKLDSGVPDRFSGSGSGTDFTLKIS
RVEAEDVGVYYCWQGTHFPYTFGQGTKLEIK

SEQ ID NO: 16-hVL22.101LC41
DVVMTQSPLSLPVTLGQPASISCRSSQSLLDADGKTYLNWFQQRPGQSPRRLIYLVSKLDSGVPDRFSGSGSGTDFTLKIS
RVEAEDVGVYYCWQGTHFPYTFGQGTKLEIK

SEQ ID NO: 17-hVL22.101LC42
DVVMTQSPLSLPVTLGQPASISCRSSQSLLDNDGKTYLNWFQQRPGQSPRRLIYLVSKLDSGVPDRFSGSGSGTDFTLKIS
RVEAEDVGVYYCWQGTHFPYTFGQGTKLEIK

SEQ ID NO: 18-SEQ ID NO 1 from WO2016092082 (used in Example 1/7) from histone 2A
SGXGKQGGKARA
Where X is citrulline SEQ ID NO: 19-SEQ ID NO 2 from WO2016092082, (used in Example 7) from histone 4
SGXGKGGKGLGKGGAKRHRKVLR
Where X is citrulline SEQ ID NO: 20-Shortened SEQ ID NO 2 from WO2016092082 (used in Example 7) from histone 4
SGXGKGGKGLGK
Where X is citrulline SEQ ID NO: 21-Peptide no 4 (human histone 2A) (SEQ ID NO 24 from WO2011070172)
QFPVGXVHRLLR
Where X is citrulline SEQ ID NO: 22-Peptide no 6 (human histone 2A) (SEQ ID NO 26 from WO2011070172)
VHRLLXKGNYSE
Where X is citrulline SEQ ID NO: 23-Human heavy chain constant domain of IgG1
ASTKGPSVFPLAPSSKSTSGGTAALGCLVKDYFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKTISKAKGQPREPQVYTLPPSRDELTK
NQVSLTCLVKGFYPSDIAVEWESNGQPENNYKTTPPVLDSDGSFFLYSKLTVDKSRWQQGNVFSCSVMHEALHNHYTQKSL
SLSPG SEQ ID NO: 24-Human kappa chain constant domain
RTVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC SEQ ID NO: 25-msVH22.101
RIQLVQSGPELKKPGEAVKISCKASGYTFTNYGMHWMKQTPGKDFRWMGWINTYSGEATYVDDFKGRFAFSLGTSASTAYL
QINNLKNDDTATYFCLRGYTYQSFDEGGDYWGQGTALTVSS SEQ ID NO: 26-hVH22.101j
QVQLVQSGAEVKKPGASVKVSCKASGYTFTNYGMHWVRQAPGQGLEWMGWINTYSGEATYAQKFQGRVTMTRDTSISTAYM
ELSRLRSDDTAVYYCLRGYTYQSFDEGGDYWGQGTLVTVSS SEQ ID NO: 27-hVH22.101HC7
QVQLVQSGAEVKKPGSSVKVSCKASGYTFTNYGMHWVRQAPGQGLEWMGWINTYSGEATYAQKFQGRVTITADESTSTAYM
ELSSLRSEDTAVYYCLRGYTYQSFDEGGDYWGQGTLVTVSS SEQ ID NO: 28-hVH22.101HC8
QVQLVQSGAEVKKPGSSVKVSCKASGYTFTNYGMHWVRQAPGQGLEWMGWINTYSGEATYVDDFQGRVTITADESTSTAYM
ELSSLRSEDTAVYYCLRGYTYQSFDEGGDYWGQGTLVTVSS SEQ ID NO: 29-hVH22.101HC10
QVQLVQSGAEVKKPGASVKVSCKASGYTFTNYGMHWVRQAPGQGLEWMGWINTYSGEATYVDDFQGRVTMTRDTSISTAYM
ELSRLRSDDTAVYYCLRGYTYQSFDEGGDYWGQGTLVTVSS SEQ ID NO: 30-msVL22.101
DVVMTQTPLTLSVTTGQPASISCKSSQSLLDSDGKTYLNWLFQRPGQSPKRLIYLVSKLDSGVPDRFTGSGSGTDFTLKIS
RVEAEDLGIYYCWQGTHFPYTFGGGTNLEIK SEQ ID NO: 31-hVL22.101e
DVVMTQSPLSLPVTLGQPASISCRSSQSLVDSDGKTYLNWFQQRPGQSPRRLIYLVSKLDSGVPDRFSGSGSGTDFTLKIS
RVEAEDVGVYYCWQGTHFPYTFGQGTKLEIK SEQ ID NO: 32-hVL22.101g
DVVMTQSPLSLPVTLGQPASISCRSSQSLLDSDGKTYLNWFQQRPGQSPRRLIYLVSKLDSGVPDRFSGSGSGTDFTLKIS
RVEAEDVGVYYCWQGTHFPYTFGQGTKLEIK

| Sequence listing |
| --- |

SEQ ID NO: 33-hVL22.101h
DVVMTQSPLSLPVTLGQPASISCRSSQSLVASDGKTYLNWFQQRPGQSPRRLIYLVSKLDSGVPDRFSGSGSGTDFTLKIS
RVEAEDVGVYYCWQGTHFPYTFGQGTKLEIK

SEQ ID NO: 34-hVL22.101i
DVVMTQSPLSLPVTLGQPASISCRSSQSLVESDGKTYLNWFQQRPGQSPRRLIYLVSKLDSGVPDRFSGSGSGTDFTLKIS
RVEAEDVGVYYCWQGTHFPYTFGQGTKLEIK

SEQ ID NO: 35-hVL22.101j
DVVMTQSPLSLPVTLGQPASISCRSSQSLVSSDGKTYLNWFQQRPGQSPRRLIYLVSKLDSGVPDRFSGSGSGTDFTLKIS
RVEAEDVGVYYCWQGTHFPYTFGQGTKLEIK

SEQ ID NO: 36-CDR1 of msVL22.101 and hVL22.101g
QSLLDSDGKTY

SEQ ID NO: 37-CDR1 of hVL22.101e
QSLVDSDGKTY

SEQ ID NO: 38-CDR1 of hVL22.101h
QSLVASDGKTY

SEQ ID NO: 39-CDR1 of hVL22.101i
QSLVESDGKTY

SEQ ID NO: 40-CDR1 of hVL22.101j
QSLVSSDGKTY

SEQ ID NO: 41-CDR1 of hVL22.101LC16
QSLLESDGKTY

SEQ ID NO: 42-CDR1 of hVL22.101LC19
QSLLDSEGKTY

SEQ ID NO: 43-CDR1 of hVL22.101LC20
QSLLDSSGKTY

SEQ ID NO: 44-CDR1 of hVL22.101LC22
QSLLESEGKTY

SEQ ID NO: 45-CDR1 of hVL22.101LC23
QSLLESSGKTY

SEQ ID NO: 46-CDR1 of hVL22.101LC24
QSLLESDAKTY

SEQ ID NO: 47-CDR1 of hVL22.101LC25
QSLLDTEGKTY

SEQ ID NO: 48-CDR1 of hVL22.101LC26
QSLLDTSGKTY

SEQ ID NO: 49-CDR1 of hVL22.101LC37
QSLLDSAGKTY

SEQ ID NO: 50-CDR1 of hVL22.101LC38
QSLLESAGKTY

SEQ ID NO: 51-CDR1 of hVL22.101LC39
QSLLDAEGKTY

SEQ ID NO: 52-CDR1 of hVL22.101LC40
QSLLDNEGKTY

SEQ ID NO: 53-msFibβ XG (SEQ ID NO 37 from WO2011070172)
EPTDSLDAXGHRPVDRR
Where X is citrulline SEQ ID NO: 54-msVim XS/XL (SEQ ID NO 38 from WO2011070172)
YVTXSSAVXLXSSVP
Where X is citrulline SEQ ID NO: 55-Region around CDR2 of msVL22.101 and hVL22.101(LC)y
LVSKLDS

| Sequence listing |
|---|
| SEQ ID NO: 56-Heavy chain constant domain of hCH22.101f<br>ASTKGPSVFPLAPSSKSTSGGTAALGCLVKDYFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAKGQPREPQVYTLPPSRDELTK<br>NQVSLTCLVKGFYPSDIAVEWESNGQPENNYKTTPPVLDSDGSFFLYSKLTVDKSRWQQGNVFSCSVMHEALHNHYTQKSL<br>SLSPGK<br><br>SEQ ID NO: 57-Consensus sequence for VL CDR1<br>QSL-$X_1$-D-$X_2$-D-$X_3$-KTY<br>where $X_1$ is V or L, $X_2$ is T, S, A or N and $X_3$ is G or A (SEQ ID NO: 57)<br><br>SEQ ID NO: 58-Consensus sequence for VL CDR1<br>QSL-$Z_1$-$Z_2$-$Z_3$-$Z_4$-$Z_5$-KTY<br>where $Z_1$ is V or L, $Z_2$ is D or E, $Z_3$ is T, S, A or N, $Z_4$ is D, E, S or A and<br>$Z_5$ is G or A (SEQ ID NO: 58) |

The invention claimed is:

1. An antibody or binding fragment thereof that specifically binds to a citrullinated epitope on deiminated human histone 2A and/or histone 4, wherein the antibody or binding fragment thereof comprises:

a) a VL CDR1 set forth in SEQ ID NO: 9 (QSLL-DADGKTY); and
b) a VH CDR1 set forth in SEQ ID NO: 1 (GYTFTNYG),
   a VH CDR2 set forth in SEQ ID NO: 2 (INTYSGEA),
   a VH CDR3 set forth in SEQ ID NO: 3 (LRGYTYQS FDEGGDY), a VL CDR2 set forth in SEQ ID NO: 4 (LVS) and a VL CDR3 set forth in SEQ ID NO: 5 (WQGTHFPYT).

2. The antibody or binding fragment thereof of claim 1, wherein the antibody or binding fragment thereof comprises:
 a) a VL CDR1 set forth in SEQ ID NO: 9;
 b) a VL CDR2 set forth in SEQ ID NO:4 and a VL CDR3 set forth in SEQ ID NO:5; and
 c) the heavy chain variable domain amino acid sequence set forth in SEQ ID NO: 11 or 12.

3. The antibody or binding fragment thereof of claim 1, wherein the antibody or binding fragment thereof comprises the heavy chain variable domain amino acid sequence set forth in SEQ ID NO: 11 and the light chain variable domain amino acid sequence set forth in SEQ ID NO: 16.

4. The antibody or binding fragment thereof of claim 1, wherein the antibody or binding fragment thereof comprises the heavy chain variable domain amino acid sequence set forth in SEQ ID NO: 12 and the light chain variable domain amino acid sequence set forth in SEQ ID NO: 16.

5. The antibody or binding fragment thereof of claim 1, that specifically binds to a citrullinated epitope on deiminated human histone 2A and/or histone 4, wherein the antibody or binding fragment thereof comprises:
 a) a VL CDR1 present in SEQ ID NO: 16; and
 b) the heavy chain variable domain amino acid sequence set forth in SEQ ID NO: 11 or 12.

6. The antibody or binding fragment thereof of claim 1, that specifically binds to a peptide selected from the group consisting of SEQ ID NOs: 18, 19, 20, 21 and 22, and binds deiminated human histone 2A and/or histone 4.

7. The antibody or binding fragment thereof of claim 1, that specifically binds to a citrullinated epitope on deiminated human histone 2A and/or histone 4 with an affinity of at least 1 nM or less.

8. The antibody or binding fragment thereof of claim 1, wherein the antibody or binding fragment thereof is selected from the group consisting of recombinant antibodies, single chain antibodies, single chain variable fragments (scFv), variable fragments (Fv), fragment antigen-binding regions (Fab), single-domain antibodies (sdAb), VHH antibodies, nanobodies, camelids-derived single-domain antibodies, shark IgNAR-derived single-domain antibody fragments (VNAR), diabodies, triabodies, Anticalins and aptamers.

9. The antibody or binding fragment thereof of claim 1, that is a full-length antibody.

10. The antibody or binding fragment thereof of claim 9, comprising an Fc region, such as an IgG1, IgG2, IgG3 or IgG4 region.

11. The antibody or binding fragment thereof of claim 1, comprising a heavy chain constant region comprising SEQ ID NO: 23 or 56, and/or a light chain constant region comprising SEQ ID NO: 24.

12. The antibody or binding fragment thereof of claim 11, wherein the antibody comprises the heavy chain variable domain amino acid sequence set forth in SEQ ID NO: 11, the light chain variable domain amino acid sequence set forth in SEQ ID NO: 16, the heavy chain constant region amino acid sequence set forth in SEQ ID NO: 23 or 56, and the light chain constant region amino acid sequence set forth in SEQ ID NO: 24.

13. The antibody or binding fragment thereof of claim 1, that is conjugated to an additional moiety.

14. A pharmaceutical composition comprising the antibody or binding fragment thereof of claim 1 and at least one pharmaceutically acceptable diluent or carrier.

15. The pharmaceutical composition of claim 14, further comprising another active ingredient.

* * * * *